United States Patent
Charton et al.

(10) Patent No.: US 10,323,016 B2
(45) Date of Patent: Jun. 18, 2019

(54) IMIDAZOL- OR 1,2,4-TRIAZOL-DERIVATIVES AND THEIR USE

(71) Applicants: UNIVERSITE DE LILLE 2 DROIT ET SANTE, Lille (FR); INSTITUT PASTEUR DE LILLE, Lille (FR); INSERM (INSTITUT NATIONAL DE LA SANTE ET DE LA RECHERCHE MEDICALE), Paris (FR)

(72) Inventors: Julie Charton, Haubourdin (FR); Benoit Deprez, Lille (FR); Florence Leroux, Templemars (FR); Bart Staels, Petit-Enghien (BE); Anne Muhr-Tailleux, Marcq en Baroeul (FR); Nathalie Hennuyer, Corbehem (FR); Sophie Lestavel, Villeneuve d'ascq (FR); Manuel Lassalle, Lille (FR); Barbara Dubanchet, Blotzheim (FR)

(73) Assignees: UNIVERSITE DE LILLE 2 DROIT ET SANTE, Lille (FR); INSTITUT PASTEUR DE LILLE, Lille (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 0 days.

(21) Appl. No.: 15/315,270

(22) PCT Filed: Jun. 11, 2015

(86) PCT No.: PCT/EP2015/063055
§ 371 (c)(1),
(2) Date: Nov. 30, 2016

(87) PCT Pub. No.: WO2015/189330
PCT Pub. Date: Dec. 17, 2015

(65) Prior Publication Data
US 2017/0190687 A1   Jul. 6, 2017

(30) Foreign Application Priority Data
Jun. 12, 2014 (EP) .................... 14305893

(51) Int. Cl.
*C07D 403/12* (2006.01)
*C07D 401/12* (2006.01)
*C07D 233/88* (2006.01)
*C07D 249/14* (2006.01)

(52) U.S. Cl.
CPC ......... *C07D 401/12* (2013.01); *C07D 233/88* (2013.01); *C07D 249/14* (2013.01); *C07D 403/12* (2013.01)

(58) Field of Classification Search
CPC .................................................. C07D 401/12
See application file for complete search history.

(56) References Cited

U.S. PATENT DOCUMENTS 7,304,082 B2 * 12/2007 Marino, Jr. ........ A61K 31/4196
514/384

FOREIGN PATENT DOCUMENTS

| WO | 03104207   | 12/2003 |
| WO | 2005087750 | 9/2005  |
| WO | 2010093845 | 8/2010  |
| WO | 2011071565 | 6/2011  |

OTHER PUBLICATIONS

Inflammatory bowel disease [online], retrieved from the internet on May 30, 2017; URL: http://www.mayoclinic.org/diseases-conditions/inflammatory-bowel-disease/basics/deinifition.*
The International Search Report and Written Opinion, dated Jul. 8, 2015, in the corresponding PCT Appl. No. PCT/EP2015/063055 .
Joshua C P et al: "Reaction of 1-Aryl-, 1,3-Diaryl- and 1-Alkyl-3-aryl-S-alkyl-isothioureas with 4-Akyl/Aryl Thiosemicarbazides: Formation of 4-Alkyl/Aryl-3-arylamino-5-mercapto-1,2,4-triazoles and 2,5-Diarylamino-1,3,4-thiadiazoles", Journal of the Indian Chemical Society, The Indian Chemical Society, Calcutta; in, vol. 67, No. 9, Sep. 1, 1990 (Sep. 1, 1990), pp. 759-763.
Database Caplus,[Online] Jan. 1, 1968(Jan. 1, 1968), Rao Y Ramachandra: "Isomeric changes involving amidino and thioamidino systems. I. Conversion of 5-amino-2-arylamino-1,3,4-thiadiazoles into 5-amino-4-aryl-3-mercapto-1,2,4-triazoles" XP002730380, retrieved from CAPLUS; STN Database accession No. 1969-3963, RNs 21135-68-2, 31123-70-6.
The English translation of the Japanese Office Action, dated Feb. 25, 2019, in the corresponding Japanese Application No. 2016-572538.

* cited by examiner

*Primary Examiner* — Shawquia Jackson

(57) ABSTRACT

The present invention is directed to novel compounds of formula (I), pharmaceutically acceptable salts or solvates thereof, and their use.

(I)

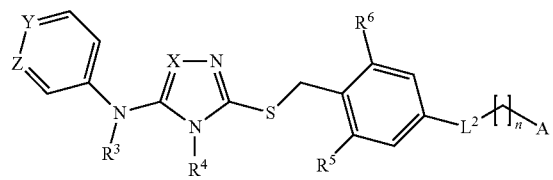

17 Claims, No Drawings

IMIDAZOL- OR 1,2,4-TRIAZOL-DERIVATIVES AND THEIR USE

CROSS-REFERENCE TO RELATED APPLICATIONS

This application is a National Stage Application of PCT/EP2015/063055 filed Jun. 11, 2015, which claims priority from European Patent Application No. 14305893.1 filed Jun. 12, 2014. Each of the prior mentioned applications is hereby incorporated by reference herein in its entirety.

The present invention relates to novel compounds including their pharmaceutically acceptable salts and solvates, which are agonists of TGR5 (G protein-coupled bile acid receptor 1, also named Gpbar 1 or M-BAR) and are useful as therapeutic compounds, particularly in the treatment and/or prevention of TGR5 related diseases, such as Type 2 diabetes (T2D) also known as diabetes mellitus and conditions that are often associated with this disease including, lipid disorders such as dyslipidemia, hypertension, obesity, atherosclerosis and its sequelae.

BACKGROUND OF THE INVENTION

Type 2 diabetes (T2D) also known as diabetes mellitus is a growing health problem. Recent estimates indicate there were 171 million people in the world with diabetes in the year 2000 and this is projected to increase to 366 million by 2030 (Wild S, Roglic G, Green A, Sicree R, King H. Global Prevalence of Diabetes: Estimates for the year 2000 and projections for 2030. Diabetes Care. 2004, 27, 1047-1053). The classical treatment for type 2 diabetes developed over the past 20 years has been based on 2 types of oral anti-hyperglycemic drugs; sulfonylureas that stimulate insulin secretion and the biguanides that have a broad spectrum of effects, but act primarily on hepatic insulin resistance. Then, alpha glucosidase inhibitors (i.e. acarbose) have been developed which decrease the intestinal absorption of glucose. A new category of molecules has appeared called thiazolidinediones (TZD). They act through binding and activation of the nuclear receptor peroxisome proliferator-activated receptor gamma (PPARγ). More recently, the recognition that hormones secreted by the gut play a role in maintaining blood glucose homeostasis has led to emergence of several novel class of medications acting as analogs of the incretin glucagon-like peptide (GLP-1) or as inhibitors of its degradating enzyme dipeptidyl peptidase IV (DPP-IV inhibitors) stabilizing its half-life. GLP-1 is an incretin hormone causing enhanced post-prandial insulin secretion, but also known to have a range of additional effects including reduced gastric motility and appetite suppression, which indirectly impact on glucose metabolism in vivo (Drucker, D. J.; Sherman, S. I.; Bergenstal, R. M.; Buse, J. B., The safety of incretin-based therapies—review of the scientific evidence. J Clin Endocrinol Metab 2011, 96, 2027-2031. Baggio, L. L.; Drucker, D. J., Biology of Incretins: GLP-1 and GIP. Gastroenterology 2007, 132, 2131-2157). These new incretin-based medications offer the advantage of highly successful efficacy associated with an exceedingly favorable side effect profile and neutral effects on weight (Cefalu, W. T., Evolving treatment strategies for the management of type 2 diabetes. Am J Med Sci 2012, 343, 21-6. Gallwitz, B., Glucagon-like peptide-1 analogues for Type 2 diabetes mellitus: current and emerging agents. Drugs 2011, 71, 1675-88).

Despite the use of various hypoglycemic agents, current treatments often fail to achieve sufficient lowering of serum glucose and/or are often associated with deficiencies including hypoglycemic episodes, gastrointestinal problems, weight gain, and loss of effectiveness over time (El-Kaissi, S.; Sherbeeni, S., Pharmacological management of type 2 diabetes mellitus: an update. Curr Diabetes Rev 2011, 7, 392-405).

In this context, the bile acid receptor TGR5 appears as an emerging and promising therapeutic target (Chen X Fau-Lou, G.; Lou G Fau-Meng, Z.; Meng Z Fau-Huang, W.; Huang, W., TGR5: A Novel Target for Weight Maintenance and Glucose Metabolism. Exp Diabetes Res. 2011, 2011: 853501. Pols Tw Fau-Noriega, L. G.; Noriega Lg Fau-Nomura, M.; Nomura M Fau-Auwerx, J.; Auwerx J Fau-Schoonjans, K.; Schoonjans, K., The bile acid membrane receptor TGR5: a valuable metabolic target. Dig. Dis. 2011, 29, 37-44. Porez, G.; Prawitt, J.; Gross, B.; Staels, B. J. Lipid Res. 2012, 53, 1723-1737). TGR5 (also named Gpbarl or M-BAR) (Maruyama, T.; Miyamoto, Y.; Nakamura, T.; Tamai, Y.; Okada, H.; Sugiyama, E.; Nakamura, T.; Itadani, H.; Tanaka, K., Identification of membrane-type receptor for bile acids (M-BAR). Biochem. Biophys. Res. Commun 2002, 298, 714-719. Kawamata, Y.; Fujii, R.; Hosoya, M.; Harada, M.; Yoshida, H.; Miwa, M.; Fukusumi, S.; Habata, Y.; Itoh, T.; Shintani, Y.; Hinuma, S.; Fujisawa, Y.; Fujino, M., A G Protein-coupled Receptor Responsive to Bile Acids. J. Biol. Chem. 2003, 278, 9435-9440) is a member of the G-protein coupled receptor (GPCR) family. TGR5 is broadly expressed in human tissues, including those that are not usually known as targets of bile acids. In particular, TGR5 is highly expressed in adipose tissue, muscle and enteroendocrine cells. A body of evidence supports a role for TGR5 in energy homeostasis. Indeed, administration of bile acids to mice increased energy expenditure in the brown adipose tissue and prevented diet-induced obesity and insulin-resistance. This effect was ascribed to a cAMP dependant intracellular induction of the type 2 iodothyronine deiodase (D2) enzyme, which converts inactive thyroxine (T4) into active 3,5,5'-tri-iodothyronine (T3). By this pathway, bile acids increase energy expenditure in part through activation of mitochondrial function in brown adipose tissue and skeletal muscle, hence preventing obesity and resistance to insulin (Watanabe, M.; Houten, S. M.; Mataki, C.; Christoffolete, M. A.; Kim, B. W.; Sato, H.; Messaddeq, N.; Harney, J. W.; Ezaki, O.; Kodama, T.; Schoonjans, K.; Bianco, A. C.; Auwerx, J., Bile acids induce energy expenditure by promoting intracellular thyroid hormone activation. Nature 2006, 439, (7075), 484-489). Consistent for a role of TGR5 in energy homeostasis, female TGR5 deficient mice although not obese under chow fed conditions, showed significant fat accumulation with body weight gain compared to wild-type mice when fed a high fat diet (Maruyama, T.; Tanaka, K.; Suzuki, J.; Miyoshi, H.; Harada, N.; Nakamura, T.; Miyamoto, Y.; Kanatani, A.; Tamai, Y., Targeted disruption of G protein-coupled bile acid receptor 1 (Gpbarl/M-Bar) in mice. Journal of Endocrinology 2006, 191, 197-205). Moreover, it was shown that oleanolic acid, a component of olive oil that binds to and activates TGR5, lowers glucose and insulin levels in mice fed with a high fat diet and enhances glucose tolerance (Sato, H.; Genet, C.; Strehle, A.; Thomas, C.; Lobstein, A.; Wagner, A.; Mioskowski, C.; Auwerx, J.; Saladin, R., Anti-hyperglycemic activity of a TGR5 agonist isolated from Olea europaea. Biochem. Biophys. Res. Commun 2007, 362, 793-798). Very interestingly, bile acids and compounds that affect TGR5 activity have been shown to increase GLP-1 secretion from enteroendocrine intestinal cells (Katsuma, S.; Hirasawa, A.; Tsujimoto, G. Bile acids promote glucagon-like peptide-1 secretion through TGR5 in a murine enteroendocrine cell line STC-1 Biochem. Biophys. Res. Commun. 2005, 329, 386-390). More recently, using a combination of pharmacological and genetic gain- and loss-of-function studies in vivo, Thomas et al. (Thomas, C.; Gioiello, A.; Noriega, L.; Strehle, A.; Oury, J.; Rizzo, G.; Macchiarulo, A.; Yamamoto, H.; Mataki, C.; Pruzanski, M.; Pellicciari, R.; Auwerx, J.; Schoonjans, K., TGR5-mediated bile acid sensing controls glucose homeostasis. Cell Metab 2009, 10, 167-177) showed that TGR5 signaling induced GLP-1 release also in vivo, leading to improved liver and pancreatic function and enhanced glucose tolerance in obese mice. Therefore, pharmacological targeting of TGR5 may constitute a promising incretin-based strategy for the treatment of diabesity and associated metabolic disorders. Interestingly, in addition to its expression in enteroendocrine L cells and its incretin secretagogue activity, TGR5 has also been shown to be expressed in inflammatory cells and its activation leads to anti-inflammatory effects and to anti-atherosclerotic effects in mouse. (Kawamata, Y.; Fujii, R.; Hosoya, M.; Harada, M.; Yoshida, H.; Miwa, M.; Fukusumi, S.; Habata, Y.; Itoh, T.; Shintani, Y.; Hinuma, S.; Fujisawa, Y.; Fujino, M., A G Protein-coupled Receptor Responsive to Bile Acids. J. Biol. Chem. 2003, 278, 9435-9440. Keitel, V.; Donner, M.; Winandy, S.; Kubitz, R.; Haussinger, D., Expression and function of the bile acid receptor TGR5 in Kupffer cells. Biochem Biophys Res Commun 2008, 372, 78-84. Pols, T. W. H.; Nomura, M.; Harach, T.; LoA Sasso, G.; Oosterveer, M. H.; Thomas, C.; Rizzo, G.; Gioiello, A.; Adorini, L.; Pellicciari, R.; Auwerx, J.; Schoonjans, K., TGR5 Activation Inhibits Atherosclerosis by Reducing Macrophage Inflammation and Lipid Loading. Cell Metabolism 2007, 14, (6), 747-757).

TGR5 agonists including natural or semi-synthetic bile acids (Pellicciari, R.; Gioiello, A.; Macchiarulo, A.; Thomas, C.; Rosatelli, E.; Natalini, B.; Sardella, R.; Pruzanski, M.; Roda, A.; Pastorini, E.; Schoonjans, K.; Auwerx, J., Discovery of 6-Ethyl-23(S)-methylcholic Acid (S-EMCA, INT-777) as a Potent and Selective Agonist for the TGR5 Receptor, a Novel Target for Diabesity J. Med. Chem. 2009, 52, 7958.7961), bile alcohols, triterpenoid compounds such as oleanolic acid, betulinic acids (Genet, C. d.; Strehle, A.; Schmidt, C. I.; Boudjelal, G.; Lobstein, A.; Schoonjans, K.; Souchet, M.; Auwerx, J.; Saladin, R. g.; Wagner, A. Structure-Activity Relationship Study of Betulinic Acid, A Novel and Selective TGR5 Agonist, and Its Synthetic Derivatives: Potential Impact in Diabetes J. Med. Chem. 2010, 53, 178-190), nomilin (Ono, E.; Inoue, J.; Hashidume, T.; Shimizu, M.; Sato, R. Anti-obesity and anti-hyperglycemic effects of the dietary citrus limonoid nomilin in mice fed a high-fat diet. Biochem. Biophys. Res. Commun. 2011, 410, 677-681) or avicholic acid and synthetic nonsteroidal small molecules (Gioiello, A.; Rosatelli, E.; Nuti, R.; Macchiarulo, A.; Pellicciari, R., Patented TGR5 modulators: a review (2006-present). Expert Opin Ther Pat 2012, 22, (12), 1399-1414) have been described recently.

However, safety concerns for some systemic TGR5 agonists were recently mentioned. Hyperplasia of the gall bladder which becomes enlarged due to delayed emptying, increased filling, or a combination of these effects was reported by investigators working with systemic TGR5 agonists in mouse models. Li, T.; Holmstrom, S. R.; Kir, S.; Umetani, M.; Schmidt, D. R.; Kliewer, S. A.; angelsdorf, D. J. The G protein-coupled bile acid receptor, TGR5, stimulates gallbladder filling. Mol. Endocrinol. 2011, 25, 1066-1071, Duan, H.; Ning, M.; Chen, X.; Zou, Q.; Zhang, L.; Feng, Y.; Zhang, L.; Leng, Y.; Shen, J., Design, Synthesis, and Antidiabetic Activity of 4-Phenoxynicotinamide and 4-Phenoxypyrimidine-5-carboxamide Derivatives as Potent and Orally Efficacious TGR5 Agonists. Journal of Medicinal Chemistry 2012, 55, (23), 10475.

More recently, it was reported that TGR5 stimulation in skin by systemic agonists triggers intense pruritus, comparable to the effect of the naturally occurring bile acids during cholestasis (Alemi, F.; Kwon, E.; Poole, D. P.; Lieu, T.; Lyo, V.; Cattaruzza, F.; Cevikbas, F.; Steinhoff, M.; Nassini, R.; Materazzi, S.; Guerrero-Alba, R.; Valdez-Morales, E.; Cottrell, G. S.; Schoonjans, K.; Geppetti, P.; Vanner, S. J.; Bunnett, N. W.; Corvera, C. U., The TGR5 receptor mediates bile acid-induced itch and analgesia. The Journal of Clinical Investigation 2013, 123, (4), 1513). Consequently, a much lower systemic exposure or even a non systemic exposure may be necessary for the development of a non-toxic TGR5 agonist.

International patent application WO 2011/071565 describes imidazole and triazole based TGR5 agonists having a quaternary ammonium moiety.

There is however still a need for new compounds that may be of therapeutic value in the treatment of TGR5 related diseases, such as T2D and conditions that are associated with this disease including, lipid disorders such as dyslipidemia, hypertension, obesity, atherosclerosis and its sequelae.

SUMMARY OF THE INVENTION

The invention thus encompasses compounds of general Formula I, their pharmaceutically acceptable salts and solvates as well as methods of use of such compounds or compositions comprising such compounds as agonists of TGR5 activity.

In a general aspect, the invention provides compounds of general Formula I:

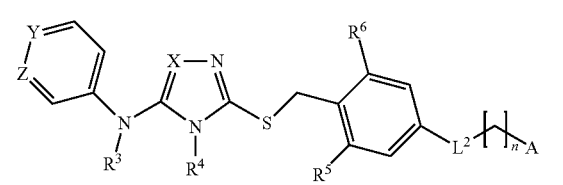

(I)

or pharmaceutically acceptable salts or solvates thereof, wherein

X is CH or N;

Y is $CR^1$ or N;

Z is $CR^2$ or N; with the proviso that Y and Z are not both N;

$R^1$ and $R^2$ are independently H, C1-C2-alkoxy or halo;

$R^3$ is H or C1-C4-alkyl;

$R^4$ is phenyl or pyridinyl, said phenyl or pyridinyl being unsubstituted or substituted by one or more groups selected from the group consisting of halo, C1-C2-alkoxy, and haloalkyl;

$R^5$ and $R^6$ are independently H, halo or C1-C2-alkyl;

$L^2$ is O, —C≡C—, $CH_2$, NH, NH(CO), (CO)NH, $NH(SO_2)$, or $(SO_2)NH$ n is an integer from 0 to 4;

A is selected from the group consisting of $N(R^7)_2$ wherein $R^7$ is H or linear C1-C4-alkyl, —$SO_3H$,

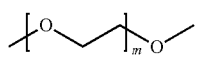

wherein m is 3 to 500,

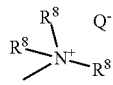

wherein $R^8$ is linear C1-C4-alkyl and $Q^-$ is a counter anion, and a cyclic moiety selected from the group consisting of

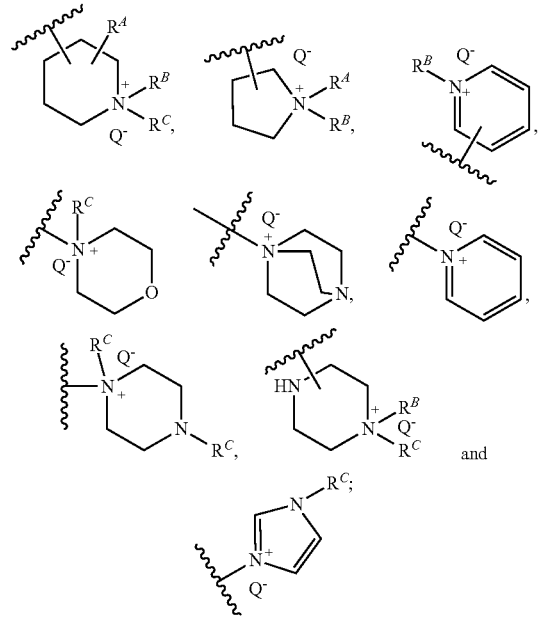

wherein $R^A$ is H, OH, C0-C4-alkyl-COOH or C1-C6-alkyl, $R^B$ is C1-C6-alkyl optionally substituted with COOH, $R^C$ is C1-C6-alkyl, and $Q^-$ is a counter anion; or
$L^2$-$(CH_2)_n$-A is H.

Suitable, generally pharmaceutically acceptable, counter anions V are well known to those skilled in the art. Non-limiting examples of suitable counter anions include acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, halides such as fluoride, chloride, bromide, iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate. Preferred counter anions $Q^-$ are selected from formate and halides such as fluoride, chloride, bromide and iodide.

Preferred compounds of Formula I are those, wherein one or more of $L^2$, n and A are as defined as follows:
$L^2$ is O, —C≡C—, $CH_2$, NH, NH(CO), (CO)NH, NH($SO_2$), or ($SO_2$)NH;
n is an integer from 0 to 4;

A is selected from the group consisting of —$SO_3H$, $N(R^7)_2$, wherein $R^7$ is H or linear C1-C4-alkyl,

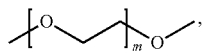

wherein m is 3 to 500,

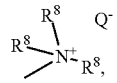

wherein $R^8$ is linear C1-C4-alkyl and $Q^-$ is a counter anion, anda cyclic moiety selected from the group consisting of

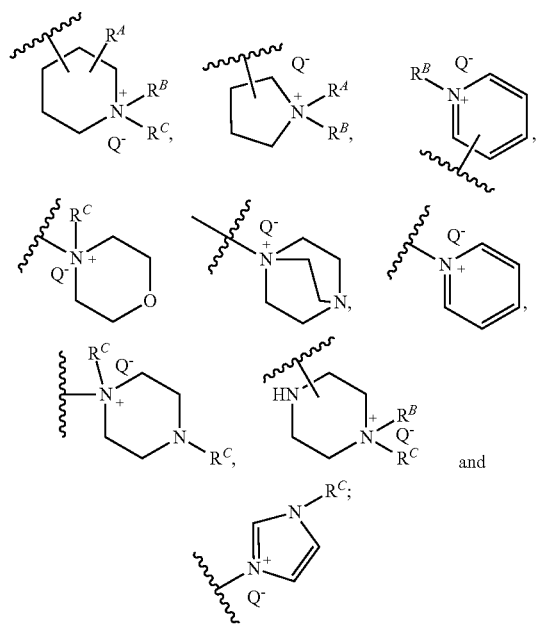

wherein $R^A$ is H, OH, C0-C4-alkyl-COOH or C1-C6-alkyl, $R^B$ is C1-C6-alkyl optionally substituted with —COOH, $R^C$ is C1-C6-alkyl, and $Q^-$ is a counter anion.

Indeed, without wanting to be bound to any theory, the present inventors believe that the $L^2$-$(CH_2)_n$-A moiety as defined herein and not being H limits the absorption of the compounds of the invention in the intestine and thus decreases their systemic action. The resulting compounds are thus topical agonists which have the advantage of promoting GLP-1 secretion in intestine without side effects due to TGR5 activation in other organs.

In another aspect, the present invention provides a pharmaceutical composition comprising at least one compound according to the invention or a pharmaceutically acceptable salt or solvate thereof.

The invention also relates to the use of the above compounds or their pharmaceutically acceptable salts and solvates as modulators of TGR5, preferably as agonists of TGR5 and more preferably as agonists of TGR5 exerting their action locally in the intestine with low or even without systemic exposure. In view of the drawbacks reported for systemic TGR5 agonists, the preferred agonists of the invention have the advantage of enhancing safety and the therapeutic index for potential chronic administration. The invention further provides the use of a compound according to the invention or a pharmaceutically acceptable salt or solvate thereof as a medicament. Preferably, the medicament is used for the treatment and/or prevention of TGR5 related diseases, such as metabolic and/or gastrointestinal diseases.

Metabolic diseases within the meaning of the present invention include, but are not limited to, type II diabetes, obesity, dyslipidemia such as mixed or diabetic dyslipidemia, hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia, hypertension, hyperlipoproteinemia, metabolic syndrome, syndrome X, thrombotic disorders, cardiovascular disease, atherosclerosis and its sequelae including angina, claudication, heart attack, stroke and others, kidney diseases, ketoacidosis, nephropathy, diabetic neuropathy, diabetic retinopathy, nonalcoholic fatty liver diseases such as steatosis or nonalcoholic steatohepatitis (NASH).

In a preferred embodiment the metabolic disease is type II diabetes, a lipid disorder such as dyslipidemia, hypertension, obesity, or atherosclerosis and its sequelae, preferably the disease is type II diabetes.

Gastrointestinal diseases within the meaning of the present invention include, but are not limited to, Inflammatory Bowel Diseases (IBD) including but not limited to colitis, Ulcerative colitis (UC) and Crohn's Disease (CD), and Irritable Bowel Syndrome (IBS), intestinal injury disorders such as short-bowel syndrome, diseases involving intestinal barrier dysfunction such as proctitis and pouchitis, and gastrointestinal disorders characterized by hypermotilenemia or gastrointestinal hypermotility, including but not limited to any type of diarrhea.

In a preferred embodiment, the gastrointestinal disease is Inflammatory Bowel Diseases (IBD) including but not limited to colitis, Ulcerative colitis (UC) and Crohn's Disease (CD).

DETAILED DESCRIPTION OF THE INVENTION

As noted above, the invention relates to compounds of Formula I, as well as their pharmaceutically acceptable salts and solvates.

Preferred compounds of Formula I and pharmaceutically acceptable salts and solvates thereof are those wherein one or more of X, Y, Z, $R^1$-$R^6$, $L^2$, n, and A are defined as follows:
X is CH or N;
Y is $CR^1$;
Z is $CR^2$;
$R^1$ and $R^2$ are idependently H, methoxy, chloro or fluoro, preferably methoxy or chloro, and more preferably both of $R^1$ and $R^2$ are methoxy;
$R^3$ is C1-C2-alkyl, preferably $R^3$ is methyl;
$R^4$ is phenyl or pyridinyl, substituted by one or more groups selected from the group consisting of fluoro, chloro, halomethyl, and C1-C2-alkoxy; preferably, fluoro, chloro, trifluoromethyl, and methoxy;
$R^5$ and $R^6$ are independently H, fluoro, chloro, or methyl; preferably $R^5$ and $R^6$ are both halo, and more preferably $R^5$ and $R^6$ are both fluoro;
$L^2$ is O or —C≡C—;
n is 0 or 1;

A is selected from the group consisting of $SO_3H$, $N(R^7)_2$ wherein $R^7$ is H or methyl, preferably methyl, and

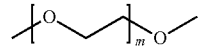

wherein m is 3 to 500;

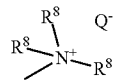

wherein $R^8$ is methyl and $Q^-$ is a counter anion; preferably A is selected from the group consisting of $N(R^7)_2$ wherein $R^7$ is H or methyl, preferably methyl,

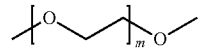

wherein m is 3 to 500, and

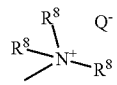

wherein $R^8$ is methyl and $Q^-$ is a counter anion; $L^2$-$(CH_2)_n$-A is H.

Particularly preferred compounds of Formula I and pharmaceutically acceptable salts and solvates thereof are those wherein $L^2$-$(CH_2)_n$-A is not H. Indeed, without wanting to be bound to any theory, the present inventors believe that the $L^2$-$(CH_2)_n$-A moiety as defined herein and not being H limits the absorption of the compounds of the invention in the intestine and thus decrease their systemic action.

In one embodiment of the invention, the compounds of Formula I are those of Formula II

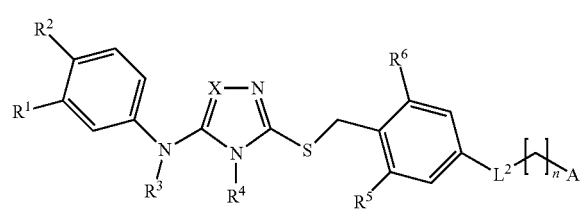

and pharmaceutically acceptable salts, and solvates thereof, wherein X, $R^1$, $R^2$, $R^3$, $R^4$, $R^5$, $R^6$, $L^2$, n, and A are as defined above with respect to Formula I.

Preferred compounds of Formula II and pharmaceutically acceptable salts and solvates thereof are those wherein $R^4$ is phenyl substituted by one or more groups selected from the group consisting of fluoro, chloro, halomethyl, and C1-C2-alkoxy; preferably, fluoro, chloro, trifluoromethyl, and methoxy.

Particularly interesting compounds of Formula II and pharmaceutically acceptable salts and solvates thereof are those, wherein $L^2$ is O, n is 0 and A is

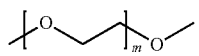

with m=3 to 500,
$L^2$ is ethynylene, n is 1 and A is $N(CH_3)_2$, or
$L^2$ is ethynylene, n is 1 and A is $[N(CH_3)_3]^+ Q^-$.

In one embodiment, compounds of Formula II and pharmaceutically acceptable salts and solvates thereof as described above are those wherein $R^3$ is methyl.

In another embodiment, the compounds of Formula II are those of Formula III

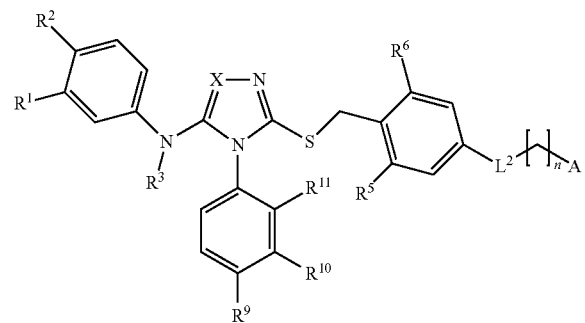

III and pharmaceutically acceptable salts, and solvates thereof, wherein
X, $R^1$, $R^2$, $R^3$, $R^5$, $R^6$, $L^2$, n, and A are as defined above with respect to Formula I; and
$R^9$, $R^{10}$, and $R^{11}$ are independently selected from the group consisting of H, fluoro, chloro, halomethyl, and C1-C2-alkoxy; preferably H, fluoro, chloro, trifluoromethyl, and methoxy, with the proviso that at least one of $R^9$, $R^{10}$, and $R^{11}$ is not H, preferably $R^9$ is fluoro and $R^{10}$ and $R^{11}$ are both H.

Particularly interesting compounds of Formula III and pharmaceutically acceptable salts and solvates thereof are those, wherein
$L^2$ is O, n is 0 and A is

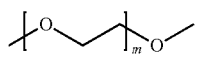

with m=3 to 500,
$L^2$ is ethynylene, n is 1 and A is $N(CH_3)_2$,
$L^2$ is ethynylene, n is 1 and A is $[N(CH_3)_3]^+ Q^-$, and/or
wherein $R^1$ and $R^2$ are preferably both methoxy, and/or
and wherein preferably $R^9$ is fluoro and $R^{10}$ and $R^{11}$ are both H.

In one embodiment, compounds of Formula III as described above are those of Formula IIIa

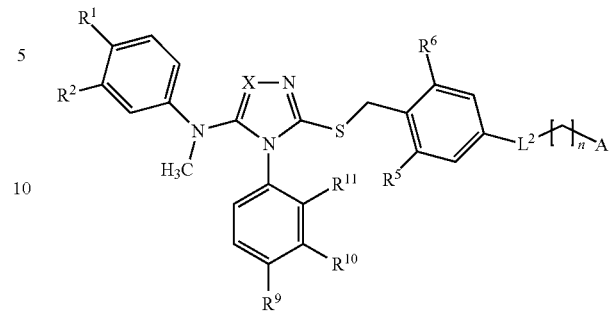

IIIa and pharmaceutically acceptable salts, and solvates thereof, wherein
X, $R^1$, $R^2$, $R^5$, $R^6$, $R^9$, $R^{10}$, $R^{11}$, $L^2$, n, and A are as defined above with respect to Formula III.

In another embodiment, the compounds of Formula I are those of Formula IV

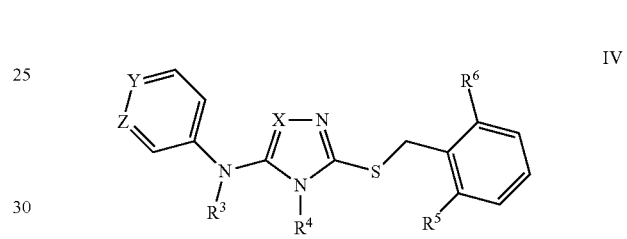

IV and pharmaceutically acceptable salts, and solvates thereof, wherein X, Y, Z, $R^3$, $R^4$, $R^5$, and $R^6$ are as defined above with respect to Formula I.

Preferred compounds of Formula IV and pharmaceutically acceptable salts and solvates thereof are those wherein Y and Z are $CR^1$ and $CR^2$, respectively, wherein $R^1$ and $R^2$ are both methoxy; and/or $R^3$ is methyl; and/or $R^4$ is 4-fluorophenyl; and/or $R^5$ and $R^6$ are both fluoro.

In another embodiment, the compounds of Formula I are those of Formula V

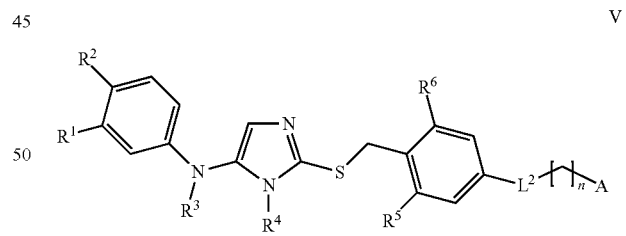

V and pharmaceutically acceptable salts, and solvates thereof, wherein $R^1$, $R^2$, $R^3$, $R^4$, $R^5$, $R^6$, $L^2$, n, and A are as defined above with respect to Formula I.

Particularly interesting compounds of Formula V and pharmaceutically acceptable salts and solvates thereof are those, wherein
$L^2$ is O, n is 0 and A is

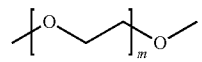

with m=3 to 500,
$L^2$ is ethynylene, n is 1 and A is $N(CH_3)_2$, or
$L^2$ is ethynylene, n is 1 and A is $[N(CH_3)_3]^+Q^-$.

Preferred compounds of Formula V and pharmaceutically acceptable salts and solvates thereof as defined above are those wherein $R^3$ is methyl.

Preferred compounds of Formula V as defined above are those of Formula Va

Va

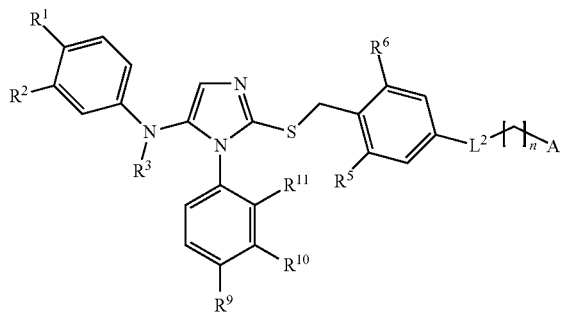

and pharmaceutically acceptable salts, and solvates thereof, wherein
$R^1$, $R^2$, $R^3$, $R^4$, $R^5$, $R^6$, $L^2$, n, and A are as defined above with respect to Formula V, and
$R^9$, $R^{10}$, and $R^{11}$ are independently selected from the group consisting of H, fluoro, chloro, halomethyl, and C1-C2-alkoxy; preferably H, fluoro, chloro, trifluoromethyl, and methoxy, with the the proviso that at least one of $R^9$, $R^{10}$, and $R^{11}$ is not H, preferably $R^9$ is fluoro and $R^{10}$ and $R^{11}$ are both H.

In another embodiment, the compounds of Formula I are those of Formula VI

VI

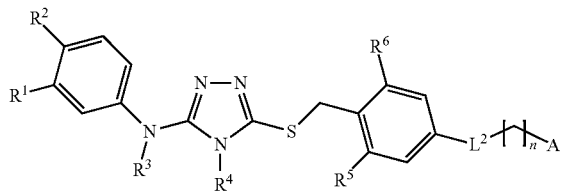

and pharmaceutically acceptable salts, and solvates thereof, wherein $R^1$, $R^2$, $R^3$, $R^4$, $R^5$, $R^6$, $L^2$, n, and A are as defined above with respect to Formula I.

Particularly interesting compounds of Formula VI and pharmaceutically acceptable salts and solvates thereof are those, wherein
$L^2$ is O, n is 0 and A is

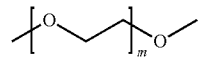

with m=3 to 500,
$L^2$ is ethynylene, n is 1 and A is $N(CH_3)_2$, or
$L^2$ is ethynylene, n is 1 and A is $[N(CH_3)_3]^+Q^-$.

Preferred compounds of Formula VI and pharmaceutically acceptable salts and solvates thereof as defined above are those wherein $R^3$ is methyl.

Preferred compounds of Formula VI as defined above are those of Formula VIa

VIa

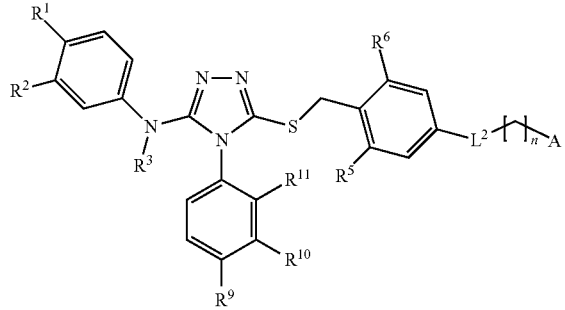

and pharmaceutically acceptable salts, and solvates thereof, wherein
$R^1$, $R^2$, $R^3$, $R^4$, $R^5$, $R^6$, $L^2$, n, and A are as defined above with respect to Formula VI, and
$R^9$, $R^{10}$, and $R^{11}$ are independently selected from the group consisting of H, fluoro, chloro, halomethyl, and C1-C2-alkoxy; preferably H, fluoro, chloro, trifluoromethyl, and methoxy, with the the proviso that at least one of $R^9$, $R^{10}$, and $R^{11}$ is not H, preferably $R^9$ is fluoro and $R^{10}$ and $R^{11}$ are both H.

In one embodiment, the compounds of Formula I and pharmaceutically acceptable salts and solvates thereof and subformulae as decribed above are those wherein $L^2$-$(CH_2)_n$-A is H.

Particularly preferred compounds of Formulae I, II, III, IIIa, V, Va, VI, and VIa and pharmaceutically acceptable salts and solvates thereof are those wherein $R^1$ and $R^2$ are both methoxy.

Particularly preferred compounds of the invention are those listed in Table 1 hereafter:

| Compound | Structure |
|---|---|
| 1 | structure |

-continued

| Compound | Structure |
|---|---|
| 2 | 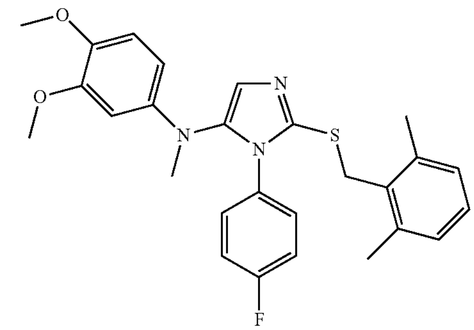 [SMILES: COc1ccc(N(C)c2cnc(SCc3c(C)cccc3C)n2-c2ccc(F)cc2)cc1OC] |
| 3 | 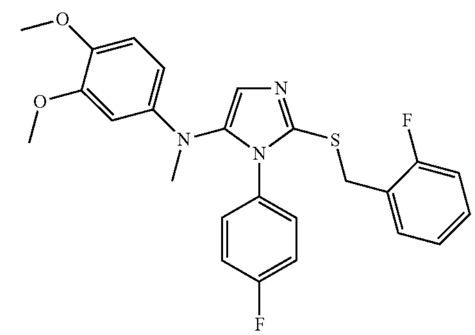 [SMILES: COc1ccc(N(C)c2cnc(SCc3ccccc3F)n2-c2ccc(F)cc2)cc1OC] |
| 4 | 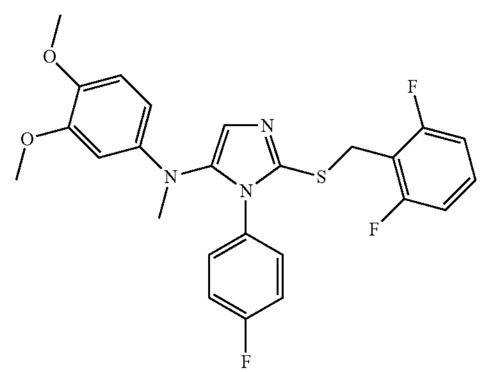 [SMILES: COc1ccc(N(C)c2cnc(SCc3c(F)cccc3F)n2-c2ccc(F)cc2)cc1OC] |
| 5 | 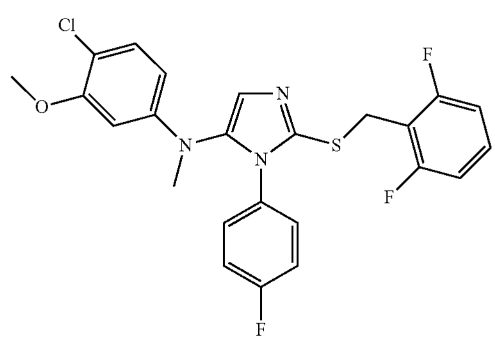 [SMILES: COc1cc(N(C)c2cnc(SCc3c(F)cccc3F)n2-c2ccc(F)cc2)ccc1Cl] |

-continued

| Compound | Structure |
|---|---|
| 6 | 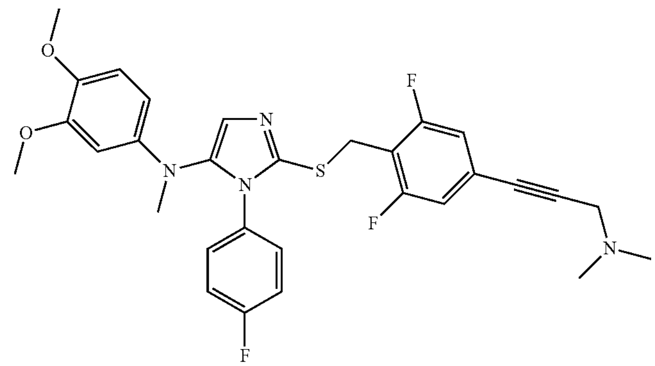 |
| 7 | 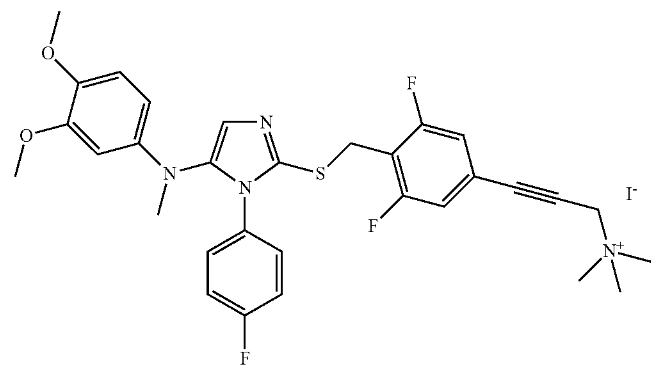 |
| 8 | 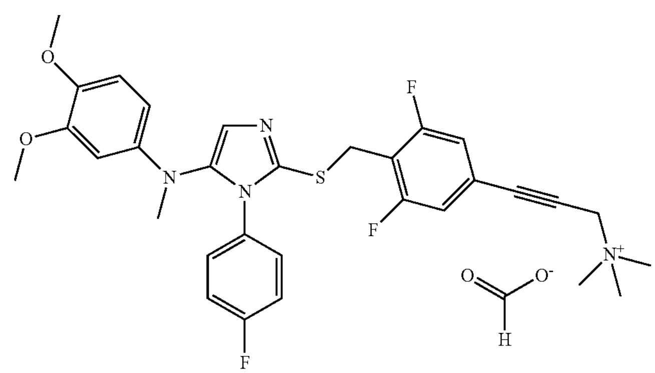 |
| 9 | 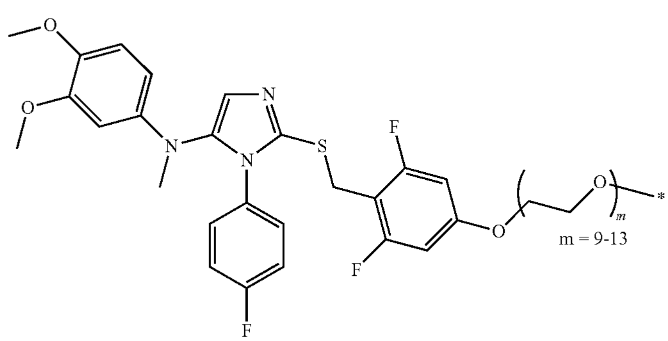 |

-continued
| Compound | Structure |
|---|---|
| 10 | 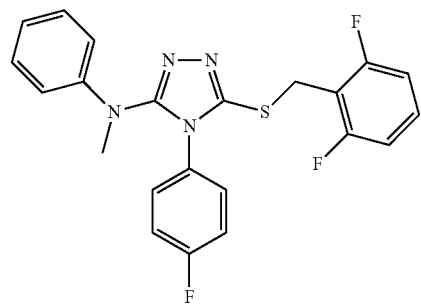 [SMILES: CN(c1ccccc1)c1nnc(SCc2c(F)cccc2F)n1-c1ccc(F)cc1] |
| 11 | 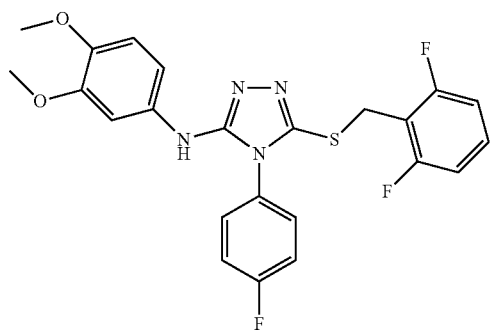 [SMILES: COc1ccc(Nc2nnc(SCc3c(F)cccc3F)n2-c2ccc(F)cc2)cc1OC] |
| 12 | 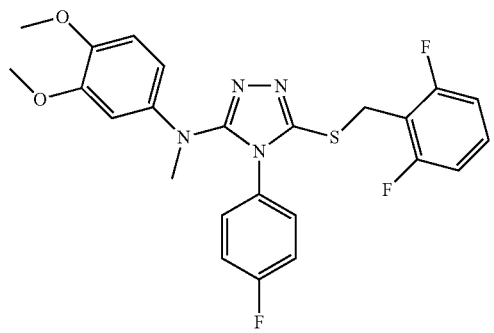 [SMILES: COc1ccc(N(C)c2nnc(SCc3c(F)cccc3F)n2-c2ccc(F)cc2)cc1OC] |
| 13 | 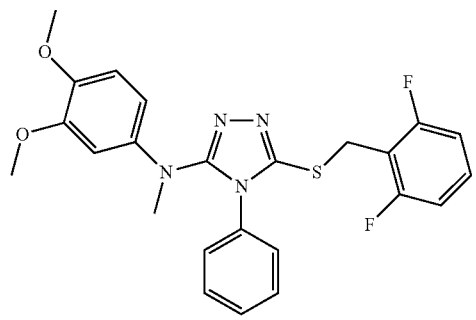 [SMILES: COc1ccc(N(C)c2nnc(SCc3c(F)cccc3F)n2-c2ccccc2)cc1OC] |

-continued
| Compound | Structure |
|---|---|
| 14 | 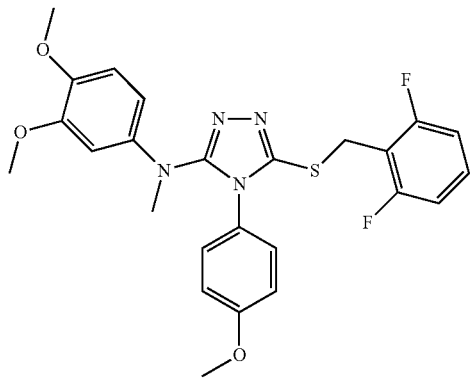 [SMILES: COc1ccc(-n2c(SCc3c(F)cccc3F)nnc2N(C)c2ccc(OC)c(OC)c2)cc1] |
| 15 | 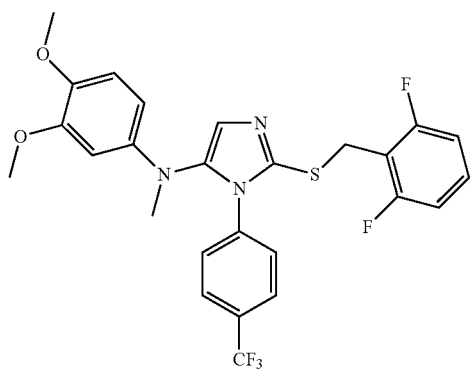 [SMILES: COc1ccc(N(C)c2cnc(SCc3c(F)cccc3F)n2-c2ccc(C(F)(F)F)cc2)cc1OC] |
| 16 | 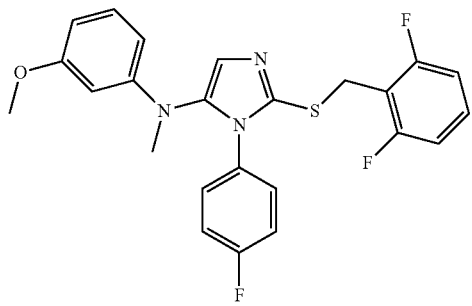 [SMILES: COc1cccc(N(C)c2cnc(SCc3c(F)cccc3F)n2-c2ccc(F)cc2)c1] |
| 17 | 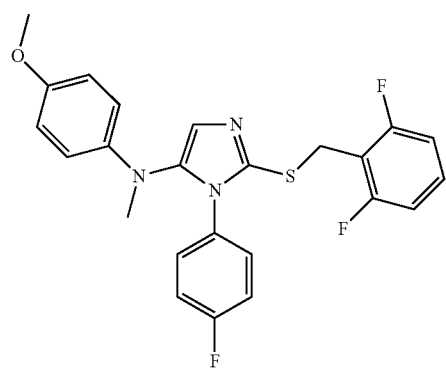 [SMILES: COc1ccc(N(C)c2cnc(SCc3c(F)cccc3F)n2-c2ccc(F)cc2)cc1] |

-continued
| Compound | Structure |
|---|---|
| 18 | 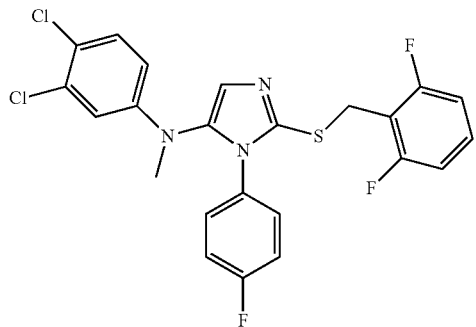 [SMILES: CN(c1ccc(Cl)c(Cl)c1)c1cnc(SCc2c(F)cccc2F)n1-c1ccc(F)cc1] |
| 19 | 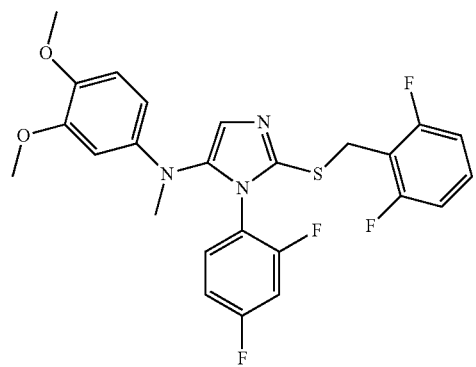 [SMILES: COc1ccc(N(C)c2cnc(SCc3c(F)cccc3F)n2-c2ccc(F)cc2F)cc1OC] |
| 20 | 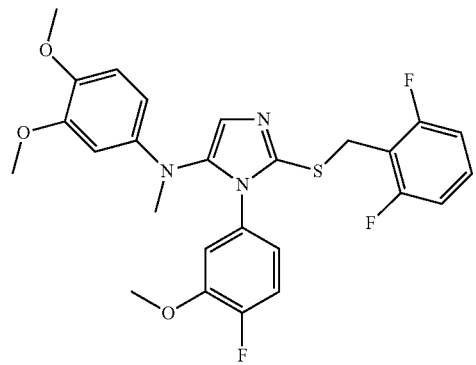 [SMILES: COc1cc(-n2c(N(C)c3ccc(OC)c(OC)c3)cnc2SCc2c(F)cccc2F)ccc1F] |
| 21 | 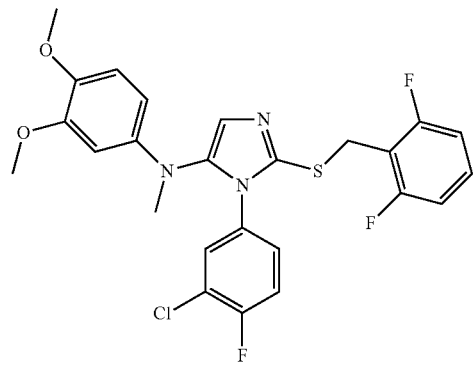 [SMILES: COc1ccc(N(C)c2cnc(SCc3c(F)cccc3F)n2-c2ccc(F)c(Cl)c2)cc1OC] |

| Compound | Structure |
|---|---|
| 22 | 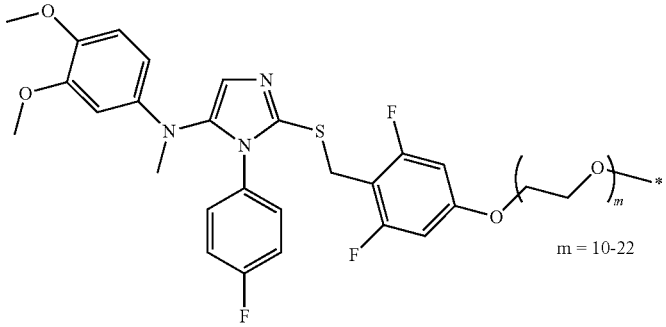<br>m = 10-22 |
| 23 | 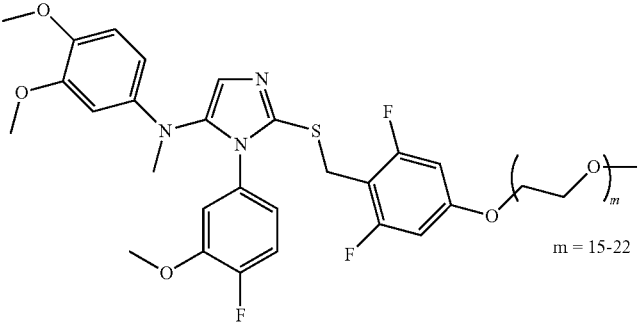<br>m = 15-22 |
| 24 | 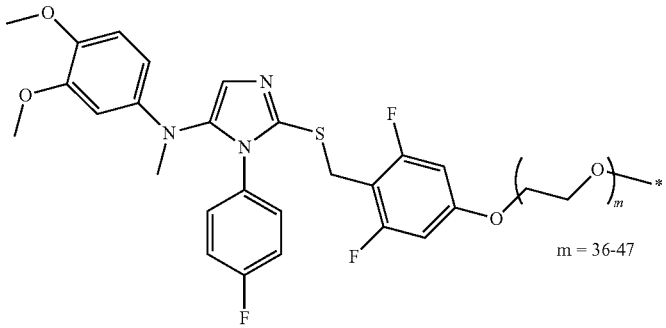<br>m = 36-47 |
| 25 | 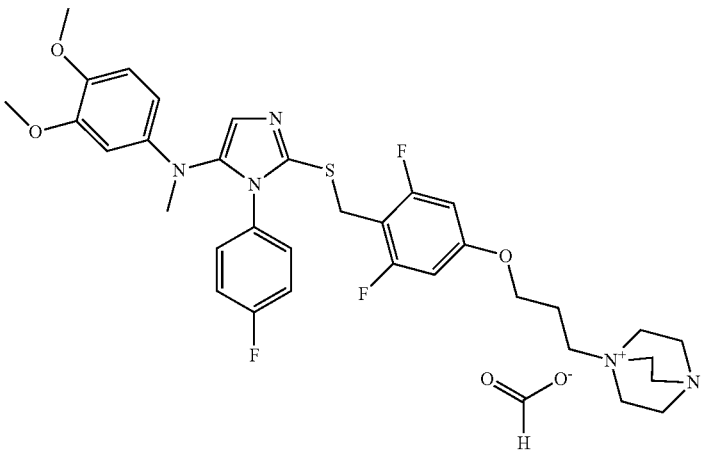 |

| Compound | Structure |
|---|---|
| 26 | 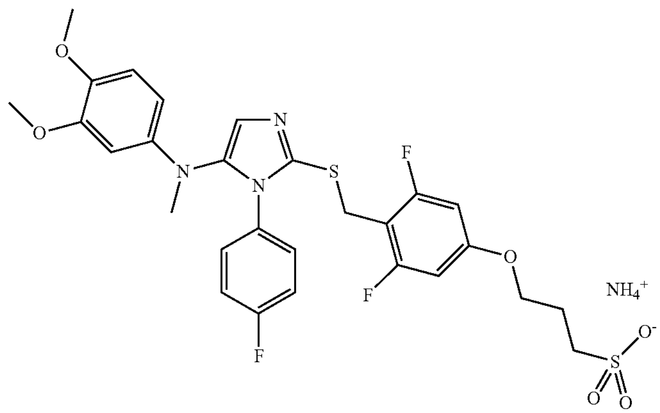 [SMILES: COc1ccc(N(C)c2cnc(SCc3c(F)cc(OCCCS(=O)(=O)[O-])cc3F)n2-c2ccc(F)cc2)cc1OC ; [NH4+]] |

The compounds of the invention and their pharmaceutically acceptable salts and solvates can be prepared by different ways with reactions known by the person skilled in the art. Reaction schemes as described in the example section illustrate by way of example different possible approaches.

The invention further provides the use of the compounds of the invention or pharmaceutically acceptable salts, or solvates thereof as agonists of TGR5, preferably agonists of TGR5 having low or no systemic activity.

Accordingly, in a particularly preferred embodiment, the invention relates to the use of compounds of formula I and subformulae or pharmaceutically acceptable salts and solvates thereof, in particular those of table 1 above, as TGR5 agonists, in particular agonists of TGR5 having low or no systemic activity.

[Applications]

The compounds of the invention are therefore useful in the prevention and/or the treatment of TGR5 related diseases, such as metabolic and/or gastrointestinal diseases.

The invention thus also relates to the use of a compound of the invention or a pharmaceutically acceptable salt or solvate thereof for use in treating and/or preventing a TGR5 related disease, in particular a metabolic and/or a gastrointestinal disease. Or in other terms, the invention also releates to a method of treating and/or preventing a TGR5 related disease, in particular a metabolic and/or a gastrointestinal disease comprising the administration of a therapeutically effective amount of a compound or pharmaceutically acceptable salt or solvate of the invention, to a patient in need thereof. Preferably the patient is a warm-blooded animal, more preferably a human.

Metabolic diseases within the meaning of the present invention include, but are not limited to, type II diabetes, obesity, dyslipidemia such as mixed or diabetic dyslipidemia, hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia hypertension, hyperlipoproteinemia, metabolic syndrome, syndrome X, thrombotic disorders, cardiovascular disease, atherosclerosis and its sequelae including angina, claudication, heart attack, stroke and others, kidney diseases, ketoacidosis, nephropathy, diabetic neuropathy, diabetic retinopathy, nonalcoholic fatty liver diseases such as steatosis or nonalcoholic steatohepatitis (NASH).

In a preferred embodiment, the metabolic disease is type II diabetes, a lipid disorder such as dyslipidemia, hypertension, obesity, or atherosclerosis and its sequelae.

In a particularly preferred embodiment, the diseases are type II diabetes and a lipid disorder such as dyslipidemia, preferably type II diabetes.

Gastrointestinal diseases within the meaning of the present invention include, but are not limited to, Inflammatory Bowel Diseases (IBD) including but not limited to colitis, Ulcerative colitis (UC) and Crohn's Disease (CD), and Irritable Bowel Syndrome (IBS), intestinal injury disorders such as short-bowel syndrome, diseases involving intestinal barrier dysfunction such as proctitis and pouchitis, and gastrointestinal disorders characterized by hypermotilenemia or gastrointestinal hypermotility, including but not limited to any type of diarrhea.

In a preferred embodiment, the gastrointestinal disease is Inflammatory Bowel Diseases (IBD) including but not limited to colitis, Ulcerative colitis (UC) and Crohn's Disease (CD).

The invention also provides for a compound of the invention or a pharmaceutically acceptable salt or solvate thereof for use in delaying the onset of a TGR5 related disease, such as a metabolic and/or a gastrointestinal disease. Or in other terms, the invention also provides for a method for delaying in patient the onset of a TGR5 related diseases, such as a metabolic and/or a gastrointestinal disease comprising the administration of a therapeutically effective amount of a compound or pharmaceutically acceptable salt or solvate of the invention, to a patient in need thereof. Preferably the patient is a warm-blooded animal, more preferably a human. The metabolic and/or gastrointestinal diseases are preferably those defined above.

The invention further provides the use of a compound of the invention or a pharmaceutically acceptable salt or solvate thereof for the manufacture of a medicament for use in treating and/or preventing TGR5 related diseases, in particular metabolic and/or gastrointestinal diseases. Preferably, the metabolic and/or gastrointestinal diseases are those defined above.

According to a further feature of the present invention, there is provided the use of a compound of the invention or a pharmaceutically acceptable salt or solvate for modulating TGR5 receptor activity, in a patient, in need of such treatment, comprising administering to said patient an effective amount of a compound of the present invention, or a pharmaceutically acceptable salt or solvate thereof. In other terms, the invention also provides a method for modulating TGR5 receptor activity, in a patient, in need of such treatment, which comprises administering to said patient an effective amount of a compound of the present invention, or a pharmaceutically acceptable salt or solvate thereof. Preferably, the patient is a warm blooded animal, and even more preferably a human.

According to one embodiment, the compounds of the invention, their pharmaceutical acceptable salts or solvates may be administered as part of a combination therapy. Thus, are included within the scope of the present invention embodiments comprising coadministration of, and compositions and medicaments which contain, in addition to a compound of the present invention, a pharmaceutically acceptable salt or solvate thereof as active ingredient, additional therapeutic agents and/or active ingredients. Such multiple drug regimens, often referred to as combination therapy, may be used in the treatment and/or prevention of any of the diseases or conditions related to with TGR5 receptor modulation, particularly type II diabetes, obesity, dyslipidemia such as mixed or diabetic dyslipidemia, hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia hypertension, hyperlipoproteinemia, metabolic syndrome, syndrome X, thrombotic disorders, cardiovascular disease, atherosclerosis and its sequelae including angina, claudication, heart attack, stroke and others, kidney diseases, ketoacidosis, nephropathy, diabetic neuropathy, diabetic retinopathy, nonalcoholic fatty liver diseases such as steatosis or nonalcoholic steatohepatitis (NASH). The use of such combinations of therapeutic agents is especially pertinent with respect to the treatment of the above-mentioned list of diseases within a patient in need of treatment or one at risk of becoming such a patient.

In addition to the requirement of therapeutic efficacy, which may necessitate the use of active agents in addition to the TGR5 agonist compounds of the invention or their pharmaceutical acceptable salts or solvates thereof, there may be additional rationales which compel or highly recommend the use of combinations of drugs involving active ingredients which represent adjunct therapy, i.e., which complement and supplement the function performed by the TGR5 receptor agonist compounds of the present invention. Suitable supplementary therapeutic agents used for the purpose of auxiliary treatment include drugs which, instead of directly treating or preventing a disease or condition related to TGR5 receptor modulation, treat diseases or conditions which directly result from or indirectly accompany the basic or underlying TGR5 receptor related disease or condition.

Thus, the methods of treatment and pharmaceutical compositions of the present invention may employ the compounds of the invention or their pharmaceutical acceptable salts or solvates thereof in the form of monotherapy, but said methods and compositions may also be used in the form of multiple therapy in which one or more compounds of the invention or their pharmaceutically acceptable salts or solvates are coadministered in combination with one or more other therapeutic agents.

The invention also provides pharmaceutical compositions comprising a compound of the invention or a pharmaceutically acceptable salt or solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable salt or solvate thereof as active ingredient, additional therapeutic agents and/or active ingredients.

Another object of this invention is a medicament comprising at least one compound of the invention, or a pharmaceutically acceptable salt or solvate thereof, as active ingredient.

Generally, for pharmaceutical use, the compounds of the inventions may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Definitions

The definitions and explanations below are for the terms as used throughout the entire application, including both the specification and the claims.

Unless otherwise stated any reference to compounds of the invention herein, means the compounds as such as well as there pharmaceutically acceptable salts and solvates.

When describing the compounds of the invention, the terms used are to be construed in accordance with the following definitions, unless indicated otherwise.

The term "halo" or "halogen" means fluoro, chloro, bromo, or iodo. Preferred halo groups are fluoro and chloro, fluoro being particularly preferred.

The term "alkyl" by itself or as part of another substituent refers to a hydrocarbyl radical of Formula $C_nH_{2n+1}$ wherein n is a number greater than or equal to 1.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl and the like. A preferred haloalkyl radical is trifluoromethyl.

The compounds of the invention containing a basic functional group and/or an acidic functional group may be in the form of pharmaceutically acceptable salts. Pharmaceutically acceptable salts of the compounds of the invention containing one or more basic functional groups include in particular the acid addition salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen pho sphate/dihydro gen phosphate, p yro glutamate, saccharate, stearate, succinate, tannate, tartrate, tosylate, trifluoroacetate and xinofoate salts. Compounds containing one or more acidic functional groups may be capable of forming pharmaceutically acceptable salts with a pharmaceutically acceptable base, for example and without limitation, inorganic bases based on alkaline metals or alkaline earth metals or organic bases such as primary amine compounds, secondary amine compounds, tertiary amine compounds, cyclic amines or basic ion exchange resins. Compounds containing one or more basic functional groups may be capable of forming pharmaceutically acceptable salts, e.g. amine groups may be transformed into ammonium groups by reacting the amine group with an inorganic or organic base or an alkylating agent such as e.g. an alkylhalide (e.g. methyliodide). When the compounds of the invention contain an acidic group as well as a basic group the compounds of the invention may also form internal salts, and such compounds are within the scope of the invention.

Pharmaceutically acceptable salts of compounds of Formula I may for example be prepared as follows:

(i) reacting the compound of Formula I with the desired acid;

(ii) by reacting the compound of Formula I with the desired base; or (iii) converting one salt of the compound of Formula I to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The term "solvate" is used herein to describe a molecular complex comprising the compound of the invention and one or more pharmaceutically acceptable solvent molecules, for example, water or ethanol. The term 'hydrate' is employed when said solvent is water.

All references to compounds of Formula I include references to salts and solvates thereof.

The compounds of the invention include compounds of Formula I as hereinbefore defined, including all polymorphs and crystal habits thereof, prodrugs and isomers thereof (including optical, geometric and tautomeric isomers) and isotopically-labeled compounds of Formula I.

In addition, although generally, with respect to the salts of the compounds of the invention, pharmaceutically acceptable salts are preferred, it should be noted that the invention in its broadest sense also includes non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula I above.

The term "patient" refers to a warm-blooded animal, more preferably a human, who/which is awaiting or receiving medical care or is or will be the object of a medical procedure.

The term "human" refers to subjects of both genders and at any stage of development (i.e. neonate, infant, juvenile, adolescent, adult). In one embodiment, the human is an adolescent or adult, preferably an adult.

The terms "treat", "treating" and "treatment, as used herein, are meant to include alleviating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e. g. TGR5 agonist) which is sufficient to achieve the desired therapeutic or prophylactic effect in the individual to which it is administered.

The term "administration", or a variant thereof (e.g., "administering"), means providing the active agent or active ingredient (e. g. a TGR5 agonist), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "agonist" as used herein means a ligand that activates an intracellular response when it binds to a receptor.

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The term "lipid disorder" as used herein means any plasma lipid disorder including but not limited to dyslipidemia such as mixed or diabetic dyslipidemia, hypercholesterolemia, low HDL cholesterol, high LDL cholesterol, hyperlipidemia and hypertriglyceridemia.

The present invention will be better understood with reference to the following examples. These examples are intended to be representative of specific embodiments of the invention, and are not intended as limiting the scope of the invention.

CHEMISTRY EXAMPLES

All reagents, solvents and starting materials were purchased from commercial suppliers and used without further purification. $^1$H NMR spectra were recorded on a Brucker Avance 300 MHz spectrometer with methanol-d6, $CDCl_3$ or DMSO-d6 as the solvent. $^{13}$C NMR spectra are recorded at 100 MHz. All coupling constants are measured in hertz (Hz) and the chemical shifts (δ) are quoted in parts per million (ppm). Liquid chromatography mass spectroscopy analyses (LCMS) were performed using LCMS-MS triple-quadrupole system (Waters) with a C18 TSK-GEL Super ODS (2 µm particle size column, 50*4.6 mm). LCMS gradient starting from 98% $H_2O$/0.1% formic acid and reaching 2% $H_2O$/98% MeOH within 5 min (method A) at a flow rate of 2 mL/min or starting from 100% $H_2O$/0.1% formic acid and reaching 5% $H_2O$/95% MeOH within 10 min (method B) at a flow rate of 1 mL/min was used. Purity (%) was determined by Reversed Phase HPLC, using UV detection (215 nM). High resolution mass spectroscopy (HRMS) was carried out on a Waters LCT Premier XE (TOF), ESI ionization mode, with a Waters XBridge C18 (150*4.6 mm, 3.5 µm particle size). LCMS gradient starting from 98% ammonium formate buffer 5 mM (pH 9.2) and reaching 95% $CH_3CN$/5% ammonium formate buffer 5 mM (pH 9.2) within 15 min at a flow rate of 1 mL/min was used.

Solvents, reagents and starting materials were purchased from well known chemical suppliers such as for example Sigma Aldrich, Acros Organics, Fluorochem, Eurisotop, VWR International, and the following abbreviations are used:
ACN: Acetonitrile,
DCM: Dichloromethane,
DMF: N,N-dimethylformamide,
EtOAc: Ethyl acetate,
EtOH: Ethanol,
MeOH: Methanol,
RT: Room temperature,
DIEA: N,N-diisopropylethylamine,
TEA: triethylamine,
Y: Yield,
g: Grams,
mg: Milligrams,
L: Liters,
mL Milliliters,
μL: Microliters,
mol: Moles,
mmol: Millimoles,
h: Hours,
min: Minutes,
TLC: Thin layer chromatography,
MW: Molecular weight,
eq: Equivalent,
μW: Microwave,
THF: Tetrahydrofuran,
TFA: Trifluoroacetic acid,
Ac: Acetyl,
tBu: tert-Butyl,
Rt: Retention time,
aq: aqueous.

General Route Toward 5-amino-2-thio-imidazole Derivatives

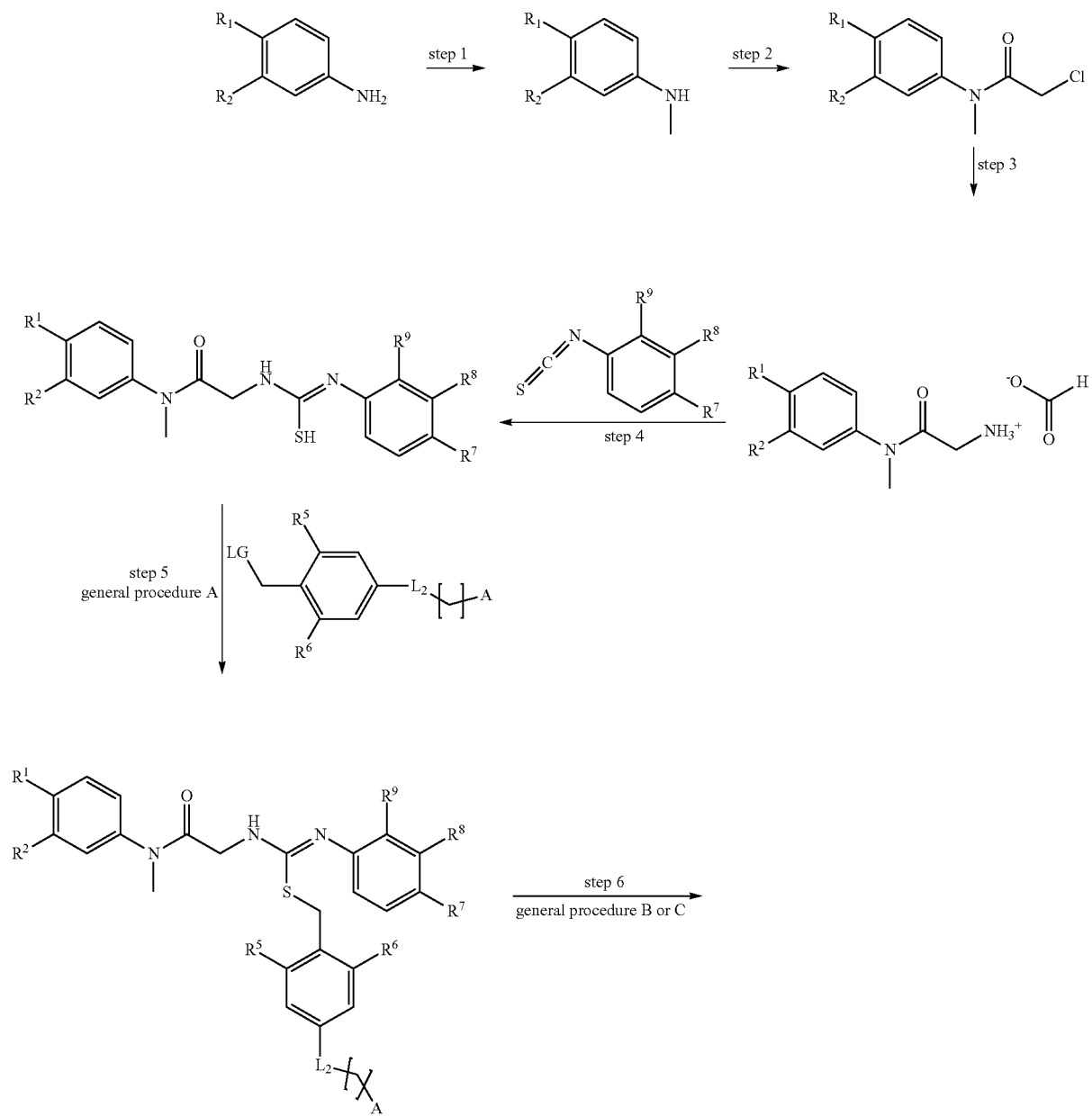

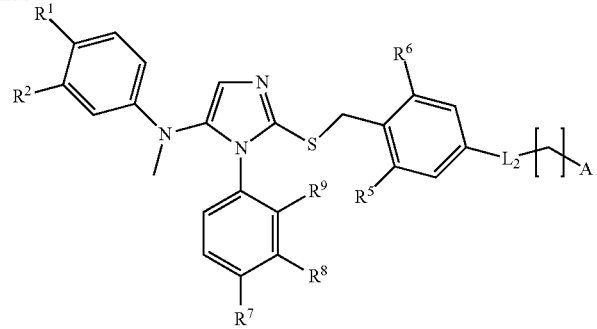

Procedure A

In a round bottom flask is added the isothioureido-derivative (1 eq), Potassium Carbonate (1 eq), sodium Iodide (0.5 eq), and acetonitrile (QS 0.2M). The suspension is stirred at room temperature for 10 min, benzyl halide (1eq) is then added. The suspension is stirred at room temperature overnight. Reaction mixture is then evaporated; residue is dissolved in EtOAc, washed with water and brine. Organic phase is dried over $Na_2SO_4$ and evaporated. Residue is purified by flash chromatography (cHex/EtOAc).

Procedure B

In a round bottom flask are introduced the isothioureido-acetamide derivative (1 eq), ethyl acetate (QS 0.1M), diisopropylethylamine (6 eq), and T3P® (3 eq). Reaction mixture is heated at reflux for 24 h. After several hours, diisopropylethylamine, and T3P® are added several times, until completion. Reaction mixture is then diluted in EtOAc, washed by saturated $NaHCO_3$ aq, and brine. Organic phase is dried over $Na_2SO_4$ and evaporated to dryness. Residue is purified by flash chromatography (cHex/EtOAc).

Procedure C

In a microwave tube are introduced the isothioureido-acetamide derivative (1 eq), ethyl acetate (QS 0.1M), diisopropylethylamine (6 eq), and T3P® (3 eq). Reaction mixture is heated under microwave irradiation at 150° C. for 10 min. Reaction mixture is then diluted with EtOAc, washed by saturated $NaHCO_3$ aq, and brine. Organic phase is then dried over $Na_2SO_4$ and evaporated. Residue is purified by flash chromatography (cHex to cHex/EtOAc).

Synthesis of Intermediate 1

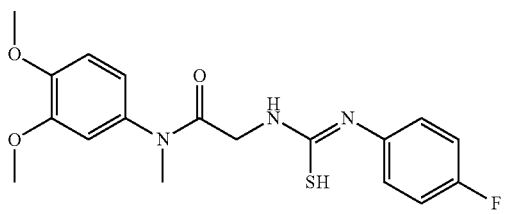 [SMILES: COc1ccc(N(C)C(=O)CN/C(S)=N/c2ccc(F)cc2)cc1OC]

Step 1

(3,4-Dimethoxy-phenyl)-methyl-amine (Intermediate 1a)

In a 250 mL flask are added 3 g of 3,4-dimethoxyaniline and 5.29 g of sodium methoxide in 35 mL of methanol (dried over $Na_2SO_4$). Then, 1.18 g of paraformaldehyde and 15 mL of methanol (dried over $Na_2SO_4$) are added. Molecular sieve (4 Angstroms) is then added and the mixture is stirred overnight at room temperature. 0.74 g of sodium borohydride are then added, and the mixture is heated under reflux for 1 hour. The mixture is then evaporated, dissolved in ethyl acetate and water, the two phases are separated. The aqueous phase is then basified by addition of saturated $NaHCO_3$ aq, and extracted by ethyl acetate. The organic phases are washed by saturated $NaHCO_3$ aq, brine, dried over $Na_2SO_4$ and evaporated, to give 2.67 g of an oily residue (77%), which was used without further purification in the next step.

MS $[M+H]^+$ m/z=168.0

$^1$H-NMR (DMSO-d6): δ (ppm) 2.62 (d, 3H, J=5.0 Hz); 3.61 (s, 3H); 3.69 (s, 3H); 5.20 (q, 1H, J=4.9 Hz); 5.99 (Dd, 1H, J=8.5 Hz, J=2.5 Hz); 6.22, (d, 1H, J=2.5 Hz); 6.71 (d, 1H, J=8.5 Hz).

Step 2

2-Chloro-N-(3,4-dimethoxy-phenyl)-N-methyl-acetamide (Intermediate 1b)

In a 250 mL flask are introduced a solution of 2.67 g of (3,4-Dimethoxy-phenyl)-methyl-amine and 7.9 mL of DIPEA in 45 mL of DCM (dried over $Na_2SO_4$). The solution is stirred at 0° C. Then, a solution of 2.4 mL of chloroacetyl chloride in 30 mL of DCM (dried over $Na_2SO_4$) is added dropwise in the flask. The mixture is then evaporated to dryness to give a brown residue which was used without further purification in the next step.

MS $[M+H]^+$ m/z=244.1

Step 3

[2-(3,4-dimethoxy-N-methyl-anilino)-2-oxo-ethyl] ammonium formate (Intermediate 1c)

Residue corresponding to 2-Chloro-N-(3,4-dimethoxy-phenyl)-N-methyl-acetamide obtained by procedure 2 is dissolved in 25 mL of Ethanol 95°, and is added dropwise in a 500 mL flask containing 320 mL of aqueous ammonia at 65° C. Reaction mixture is then evaporated to dryness. Residue is then dissolved in DCM, and extracted several times by an aqueous solution of HCOOH 1M. Aqueous phase is then evaporated to dryness, and the residue is triturated in AcCN. The supernatant is evaporated to dryness, to give 3.82 g of a brown powder (75% yield over the 2 steps).

MS $[M+H]^+$ m/z=225.1

$^1$H-NMR (DMSO-d6): δ (ppm) 3.17 (s, 3H); 3.99 (s, 2H); 3.76-3.77 (m, 6H); 6.90 (dd, 1H, J=8.4 Hz, J=2.2 Hz); 6.99-7.03 (m, 2H); 8.00 (brs, 3H); 8.20 (s, 1H)

Step 4

N-(3,4-Dimethoxy-phenyl)-2-[3-(4-fluoro-phenyl)-isothioureido]-N-methyl-acetamide (Intermediate 1)

1.5 g of 4-fluorophenylisothiocyanate and 1.59 mL of TEA are added in a 250 mL flask in 15 mL Ethanol. 3.2 g of [2-(3,4-dimethoxy-N-methyl-anilino)-2-oxo-ethyl]ammonium formate (83% purity) are dissolved in 115 mL of ethanol, 1.33 mL of TEA are added, and the mixture is added dropwise at RT. After the addition, the reaction is over. Reaction mixture is evaporated to dryness, and purified by flash chromatography (cHex/EtOAc), to give 2.8 g of a yellowish powder (76%).

MS [M−H]⁻ m/z=244.1

¹H-NMR (DMSO-d6): δ (ppm) 2.49 (s, 3H); 3.78 (m, 6H); 4.00 (d, 2H, J=4.1 Hz); 6.92 (Dd, 1H, J=8.4 Hz, J=1.8 Hz); 7.01-7.03 (m, 2H); 7.15 (m, 2H); 7.45 (m, 2H); 7.73 (m, 1H); 9.90 (s, 1H)

EXAMPLE 1

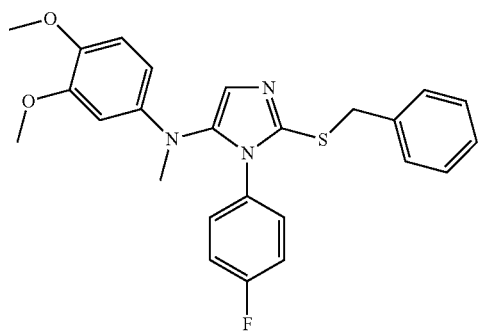 [SMILES: COc1ccc(N(C)c2cnc(SCc3ccccc3)n2-c2ccc(F)cc2)cc1OC]

Step 5

2-[2-Benzyl-3-(4-fluoro-phenyl)-isothioureido]-N-(3,4-dimethoxy-phenyl)-N-methyl-acetamide The titled product is obtained without purification as an oily residue (259 mg, 98%), following Procedure A, using N-(3,4-Dimethoxy-phenyl)-2-[3-(4-fluoro-phenyl)-isothioureido]-N-methyl-acetamide (Intermediate 1) (195 mg) and benzylbromide (85 mg).

MS [M+H]⁺ m/z=468.0

¹H-NMR (DMSO-d6): δ (ppm) 3.17 (s, 3H); 3.69-3.76 (m, 8H); 4.14 (s, 2H); 6.61 (m, 3H); 6.88 (m, 1H); 6.95-7.01 (m, 4H); 7.22-7.31 (m, 5H).

Step 6

[2-Benzylsulfanyl-3-(4-fluoro-phenyl)-3H-imidazol-4-yl]-(3,4-dimethoxy-phenyl)-methyl-amine The titled product is obtained as an orange powder (68 mg, 32%), following Procedure C, using 2-[2-Benzyl-3-(4-fluoro-phenyl)-isothioureido]-N-(3,4-dimethoxy-phenyl)-N-methyl-acetamide (249 mg).

MS [M+H]⁺ m/z=450.0

¹H-NMR (CDCl₃): δ (ppm) 2.92 (s, 3H); 3.75 (s, 3H); 3.81 (s, 3H); 4.26 (s, 2H); 6.09 (dd, J=2.8 Hz, J=8.8 Hz, 1H); 6.20 (d, J=2.7 Hz, 1H); 6.68 (d, J=8.8 Hz, 1H); 6.74-6.78 (m, 2H); 6.89-6.95 (m, 2H); 7.04 (s, 1H); 7.19-7.29 (m, 5H)

¹³C-NMR (CDCl₃): δ (ppm) 38.7; 40.3; 55.9; 56.5; 99.9; 105.8; 112.4; 115.7; 115.9 (d, J=22.8 Hz); 123.6; 127.4; 128.5; 129.0; 129.3 (d, J=8.6 Hz); 130.7; 137.4; 139.2; 139.4; 142.7; 143.1; 149.5; 162.4 (d, J=248.9 Hz).

EXAMPLE 2

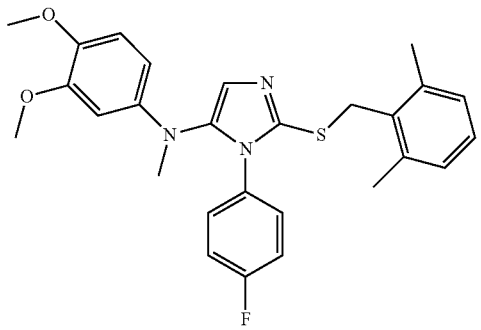 [SMILES: COc1ccc(N(C)c2cnc(SCc3c(C)cccc3C)n2-c2ccc(F)cc2)cc1OC]

Step 5

N-(3,4-Dimethoxy-phenyl)-2-[2-(2,6-dimethyl-benzyl)-3-(4-fluoro-phenyl)-isothioureido]-N-methyl-acetamide The titled product is obtained without purification as an oily residue (230 mg, 90%), following Procedure A, using N-(3,4-Dimethoxy-phenyl)-2-[3-(4-fluoro-phenyl)-isothioureido]-N-methyl-acetamide (Intermediate 1) (195 mg) and 2-(chloromethyl)-1,3-dimethyl-benzene (77 mg).

MS [M+H]⁺ m/z=496.0

¹H-NMR (DMSO-d6): δ (ppm) 2.25 (s, 6H); 3.18 (s, 3H); 3.68-3.77 (m, 5H); 4.14 (s, 2H); 6.69-7.05 (m, 11H).

Step 6

(3,4-Dimethoxy-phenyl)-[2-(2,6-dimethyl-benzylsulfanyl)-3-(4-fluoro-phenyl)-3H-imidazol-4-yl]-methyl-amine The titled product is obtained as an orange powder (63 mg, 34%) following procedureC using N-(3,4-Dimethoxy-phenyl)-2-[2-(2,6-dimethyl-benzyl)-3-(4-fluoro-phenyl)-isothioureido]-N-methyl-acetamide (200 mg).

MS [M+H]⁺ m/z=478.0

¹H-NMR (CDCl₃): δ (ppm) 2.28 (s, 6H); 2.95 (s, 3H); 3.78 (s, 3H); 3.82 (s, 3H); 4.34 (s, 2H); 6.15 (dd, J=8.7 Hz, J=2.7 Hz); 6.25 (d, J=2.8 Hz); 6.70 (d, J=8.7 Hz); 6.86-7.05 (m, 8H).

¹³C-NMR (CDCl₃): δ (ppm) 19.6; 33.3; 40.4; 56.0; 56.4; 100.1; 106.1; 112.4; 115.9 (d, J=23.0 Hz); 123.4; 127.5; 128.3; 129.3 (d, J=8.7 Hz); 130.8; 132.4; 137.6; 139.4; 140.0; 142.8; 143.1; 149.6; 162.3 (d, J=250.2 Hz).

EXAMPLE 3

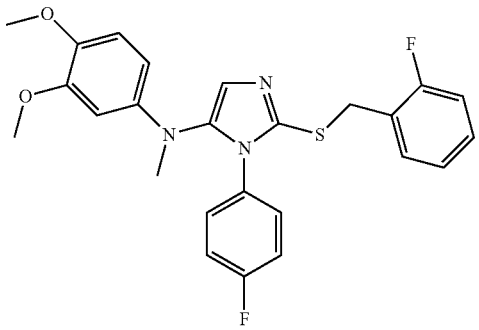 [SMILES: COc1ccc(N(C)c2cnc(SCc3ccccc3F)n2-c2ccc(F)cc2)cc1OC]

Step 5

N-(3,4-Dimethoxy-phenyl)-2-[2-(2-fluoro-benzyl)-3-(4-fluoro-phenyl)-isothioureido]-N-methyl-acetamide The titled product is obtained without purification as an oily residue (254 mg, 96%), following Procedure A, using N-(3,4-Dimethoxy-phenyl)-2-[3-(4-fluoro-phenyl)-isothioureido]-N-methyl-acetamide (Intermediate 1) (195 mg) and 1-(bromomethyl)-2-fluoro-benzene (94 mg).

MS [M+H]$^+$ m/z=486.0

$^1$H-NMR (DMSO-d6): δ (ppm) 3.16 (s, 3H); 3.39-3.76 (m, 8H); 4.17 (s, 2H); 6.59-6.89 (m, 4H); 6.95-7.00 (m, 4H); 7.11-7.19 (m, 2H); 7.31 (m, 1H); 7.41 (m, 1H)

Step 6

(3,4-Dimethoxy-phenyl)-[2-(2-fluoro-benzylsulfanyl)-3-(4-fluoro-phenyl)-3H-imidazol-4-yl]-methyl-amine The titled product is obtained as an orange powder (130 mg, 61%), following Procedure C, using N-(3,4-Dimethoxy-phenyl)-2-[2-(2-fluoro-benzyl)-3-(4-fluoro-phenyl)-isothioureido]-N-methyl-acetamide.

MS [M+H]$^+$ m/z=468.0

$^1$H-NMR (CDCl$_3$): δ (ppm) 3.77 (s, 3H); 3.81 (s, 3H); 4.27 (s, 2H); 6.11 (dd, J=8.7 Hz, J=2.7 Hz, 1H); 6.22 (d, J=2.7 Hz, 1H); 6.69 (d, J=8.7 Hz); 6.79-6.84 (m, 2H); 6.90-7.06 (m, 5H); 7.20-7.25 (m, 2H).

$^{13}$C-NMR (CDCl$_3$): δ (ppm) 31.8; 40.3; 55.9; 56.5; 100.0; 105.8; 112.4; 115.5 (d, J=21.5 Hz); 116.0 (d, J=22.8 Hz); 123.8; 124.1; 124.7 (d, J=14.8 Hz); 129.1; 129.2; 129.4; 130.7; 131.0; 139.1; 139.3; 142.7; 143.1; 149.6; 160.9 (d, J=248.3 Hz); 162.4 (d, J=249.8 Hz)

EXAMPLE 4

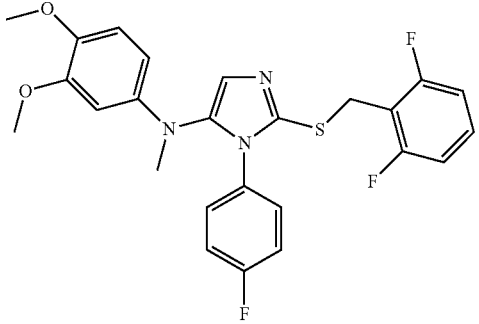 [SMILES: COc1ccc(N(C)c2cnc(SCc3c(F)cccc3F)n2-c2ccc(F)cc2)cc1OC]

Step 5

2-[2-(2,6-difluoro-benzyl)-3-(4-fluoro-phenyl)-isothioureido]-N-(3,4-dimethoxy-phenyl)-N-methyl-acetamide The titled product is obtained without purification as an oily residue (1.15 g, 91%), following Procedure A, using N-(3,4-Dimethoxy-phenyl)-2-[3-(4-fluoro-phenyl)-isothioureido]-N-methyl-acetamide (Intermediate 1) (940 mg) and 2-Bromomethyl-1,3-difluoro-benzene (518 mg).

MS [M+H]$^+$ m/z=504.0

$^1$H-NMR (DMSO-d6): δ (ppm) 3.16 (s, 3H); 3.69-3.76 (m, 8H); 4.19 (s, 2H); 6.61 (m, 2H); 6.79-6.89 (m, 2H); 6.95-7.00 (m, 4H); 7.05-7.13 (m, 3H); 7.38 (m, 1H)

Step 6

[2-(2,6-Difluoro-benzylsulfanyl)-3-(4-fluoro-phenyl)-3H-imidazol-4-yl]-(3,4-dimethoxy-phenyl)-methyl-amine In a 50 mL flask are added 2-[2-(2,6-difluoro-benzyl)-3-(4-fluoro-phenyl)-isothioureido]-N-(3,4-dimethoxy-phenyl)-N-methyl-acetamide (500 mg), 10 mL EtOAc, TEA (843 μL), and T3P® (1.77 mL). Reaction mixture is then stirred at reflux for 28 hours. After 8 hours, TEA (843 μL) and T3P® (1.77 mL) were added. After 25 hours, TEA (422 μL) and T3P® (885 μL) were added. After dilution with 20 mL EtOAc, the solution is washed by saturated NaHCO$_3$ aq, and brine. Organic phase is dried over Na$_2$SO$_4$ and evaporated. Residue is purified by flash chromatography (DCM/MeOH). 160 mg of an oily residue corresponding to the titled product are obtained (33%).

MS [M+H]$^+$ m/z=487.3

$^1$H-NMR (CDCl$_3$): δ (ppm) 2.92 (s, 3H); 3.80 (s, 3H); 3.82 (s, 3H); 4.16 (s, 2H); 6.16 (dd, J=8.7 Hz, J=2.7 Hz, 1H); 6.30 (d, J=2.7 Hz, 1H); 6.72 (d, J=8.7 Hz, 1H); 6.78 (m, 2H); 6.83-6.85 (m, 4H); 6.92 (s, 1H); 7.19 (m, 1H).

$^{13}$C-NMR (CDCl$_3$): δ (ppm) 25.9; 40.1; 55.9; 56.4; 99.9; 105.5; 111.2 (m); 112.4; 113.6 (t, J=19.3 Hz); 115.9 (d, J=22.9 Hz); 124.4; 129.1-129.2 (m); 130.8; 138.1; 139.6; 142.7; 143.2; 149.6; 161.1 (dd, J=250.0 Hz, J=7.7 Hz); 162.2 (d, J=249.0 Hz).

EXAMPLE 5

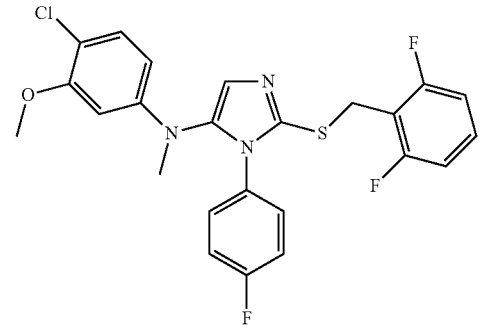 [SMILES: COc1cc(N(C)c2cnc(SCc3c(F)cccc3F)n2-c2ccc(F)cc2)ccc1Cl]

Step 1

(4-Chloro-3-methoxy-phenyl)-methyl-amine

In a 50 mL flask are added 4-Chloro-3-methoxy-phenylamine (907 mg), sodium methoxide (1.56 g), 10 mL anhydrous methanol, and paraformaldehyde (690 mg). Reaction mixture is then stirred overnight at room temperature. Then, paraformaldehyde (173 mg) and sodium methoxyde (311 mg) are added, and reaction mixture is heated at reflux for 1 hour. Sodium borohydride (436 mg) is then added, and reaction mixture is stirred at reflux for 4 hours. Once back at room temperature, mixture is partially evaporated, and KOH aq 1M (50 mL) is then added. The obtained suspension is extracted by Et$_2$O, organic phase is dried over Na$_2$SO$_4$ and evaporated. The obtained residue is purified by flash chromatography (cHex to cHex/EtOAc 8/2) to give 650 mg of the expected product (66%).

MS [M+H]$^+$ m/z=171.9

$^1$H-NMR (DMSO-d6): δ (ppm) 2.66 (d, J=4.9 Hz, 3H); 3.77 (s, 3H); 5.80 (q, J=4.9 Hz, 1H); 6.09 (dd, J=2.5 Hz, J=8.7 Hz, 1H); 6.25 (d, J=2.4 Hz, 1H); 7.04 (d, J=8.7 Hz, 1H).

Step 2

2-Chloro-N-(4-chloro-3-methoxy-phenyl)-N-methyl-acetamide

In a 100 mL flask are introduced a solution of 620 mg of 4-Chloro-3-methoxy-phenyl)-methyl-amine and 1.7 mL of DIPEA in 18 mL of DCM (dried over Na$_2$SO$_4$). The solution is stirred at 0° C. Then, a solution of 568 μL of chloroacetyl chloride in 14 mL of DCM (dried over Na$_2$SO$_4$) is added dropwise in the flask. The mixture is then evaporated to dryness to give a brown residue which was used without further purification in the next step.

MS [M+H]$^+$ m/z=248.0

Step 3

2-Amino-N-(4-chloro-3-methoxy-phenyl)-N-methyl-acetamide

Residue corresponding to 2-Chloro-N-(4-chloro-3-methoxy-phenyl)-N-methyl-acetamide (n=3.6 mmol) is dissolved in 6 mL EtOH 95°. The obtained solution is added dropwise in aqueous ammonia (30% w/w, 75 mL) at 65° C. After 1 hour stirring at 65° C., reaction mixture is evaporated. The residue is dissolved in water, pH is adjusted to 10, and the solution is extracted several times by DCM. Organic phases are dried over over Na$_2$SO$_4$ and evaporated, to give a brown oily residue. It was used in the next step without further purification.

MS [M+H]$^+$ m/z=229.0

Step 4

N-(4-Chloro-3-methoxy-phenyl)-2-[3-(4-fluoro-phenyl)-isothioureido]-N-methyl-acetamide In a 250 mL flask, 4-fluorophenylisothiocyanate (551.4 mg) and triethylamine (583 μL) are dissolved in 3 mL Ethanol. To this is added dropwise at room temperature a solution of 2-Amino-N-(4-chloro-3-methoxy-phenyl)-N-methyl-acetamide in 48 mL Ethanol. After 1 hour stirring at room temperature, mixture is evaporated to dryness, and residue is purified by flash chromatography (cHex/DCM 1/1 to pure DCM). 546 mg of a yellowish powder corresponding to the titled product are then obtained (39% yield over the 3 steps).

MS [M+H]$^+$ m/z=382.1

$^1$H-NMR (DMSO-d6): δ (ppm) 3.21 (s, 3H); 3.88 (s, 3H); 4.06 (brs, 2H); 7.01 (m, 1H); 7.16 (m, 2H); 7.26 (brs, 1H); 7.45 (m, 2H); 7.52 (d, J=8.3 Hz, 1H); 7.76 (brs, 1H); 9.90 (brs, 1H).

Step 5

N-(4-Chloro-3-methoxy-phenyl)-2-[2-(2,6-difluoro-benzyl)-3-(4-fluoro-phenyl)-isothioureido]-N-methyl-acetamide The titled product is obtained as an oily residue (603 mg, 87%), without purification, following Procedure A, using N-(4-Chloro-3-methoxy-phenyl)-2-[3-(4-fluoro-phenyl)-isothioureido]-N-methyl-acetamide (468 mg) and 2-Bromomethyl-1,3-difluoro-benzene (254 mg).

MS [M+H]$^+$ m/z=508.2

$^1$H-NMR (DMSO-d6): δ (ppm) 3.20 (s, 3H); 3.79-3.89 (m, 5H); 4.19 (s, 2H); 6.23 (brs, 2H); 6.95-7.10 (m, 6H); 7.18 (s, 1H); 7.38 (m, 1H); 7.48 (m, 1H).

Step 6

(4-Chloro-3-methoxy-phenyl)-[2-(2,6-difluoro-benzylsulfanyl)-3-(4-fluoro-phenyl)-3H-imidazol-4-yl]-methyl-amine In a microwave tube are introduced N-(4-Chloro-3-methoxy-phenyl)-2-[2-(2,6-difluoro-benzyl)-3-(4-fluoro-phenyl)-isothioureido]-N-methyl-acetamide (145 mg), 3 mL of ethyl acetate, DIPEA (74.8 μL), and T3P® (168 μL). Reaction mixture is then heated twice under microwave irradiation, 10 min at 100° C. T3P® (348 μL) and DIPEA (206 μL) are then added, and the mixture is heated at 150° C. for 20 min under microwave irradiation. Reaction mixture is washed by saturated NaHCO$_3$ aq, and brine. Organic phase is dried over Na$_2$SO$_4$ and evaporated. The obtained residue is purified by Flash Chromatography (DCM/cHex then DCM/MeOH) to give 83 mg of a yellowish residue (59%).

MS [M+H]$^+$ m/z=508.2

$^1$H-NMR (DMSO-d6): δ (ppm) 2.96 (s, 3H); 3.75 (s, 3H); 4.08 (s, 2H); 6.09 (dd, J=2.7 Hz, J=8.8 Hz, 1H); 6.27 (d, J=2.6 Hz, 1H); 7.02-7.07 (m, 3H); 7.11-7.15 (m, 3H); 7.21 (m, 2H); 7.37 (m, 1H)

$^{13}$C-NMR (DMSO-d6): δ (ppm) 26.0; 26.8; 56.2; 98.2; 106.4; 110.7; 112.1 (d, J=23.9 Hz); 113.8 (t, J=19.9 Hz); 116.5 (d, J=23.2 Hz); 125.2; 130.0; 130.1 (d, J=9.1 Hz); 130.5 (t, J=10.9 Hz); 131.2; 137.9; 138.6; 149.0; 155.3; 161.0 (dd, J=248.8 Hz, J=7.4 Hz); 162.3 (d, J=245.9 Hz).

EXAMPLES 6, 7 & 8

Example 7: A = I
Example 8: A = HCOO

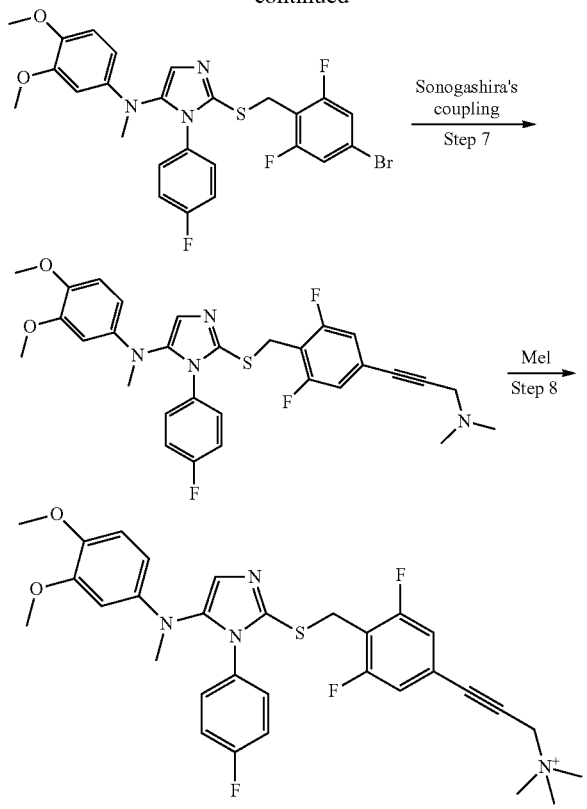

Step 5

2-[2-(4-Bromo-2,6-difluoro-benzyl)-3-(4-fluoro-phenyl)-isothioureido]N-(3,4-dimethoxy-phenyl)-N-methyl-acetamide The titled product is obtained as a yellowish powder (1.07 g, 95%) following procedure A using N-(3,4-Dimethoxy-phenyl)-2-[3-(4-fluoro-phenyl)-isothioureido]-N-methyl-acetamide (750 mg), and 5-bromo-2-(chloromethyl)-1,3-difluoro-benzene (461 mg).

MS [M+H]$^+$ m/z=583.8

$^1$H-NMR (DMSO-d6): δ (ppm) 3.15 (s, 3H); 3.73 (m, 8H); 4.14 (s, 2H); 6.60 (m, 2H); 6.79 (brs, 1H); 6.86 (m, 1H); 6.97 (m, 4H); 7.46 (m, 2H)

Step 6

[2-(4-Bromo-2,6-difluoro-benzylsulfanyl)-3-(4-fluoro-phenyl)-3H-imidazol-4-yl]-(3,4-dimethoxy-phenyl)-methyl-amine The titled product is obtained as an orange oil (867 mg, 74%) following procedureB using 2-[2-(4-Bromo-2,6-difluoro-benzyl)-3-(4-fluoro-phenyl)-isothioureido]-N-(3,4-dimethoxy-phenyl)-N-methyl-acetamide (1.07 g).

MS [M+H]$^+$ m/z=565.9

$^1$H-NMR (DMSO-d6): δ (ppm) 2.91 (s, 3H); 3.64-3.65 (m, 6H); 3.97 (s, 2H); 6.04 (dd, 1H, J=8.6 Hz, J=2.6 Hz); 6.20 (d, 1H, J=2.8 Hz); 6.76 (d, 1H, J=8.7 Hz); 6.96 (s, 1H); 7.11 (dd, 2H, J=9.0 Hz, J=5.1 Hz); 7.19 (m, 2H); 7.41 (m, 2H).

Step 7 (Example 6)

(3,4-Dimethoxy-phenyl)-[2-[4-(3-dimethylamino-prop-1-ynyl)-2,6-difluoro-benzylsulfanyl]-3-(4-fluoro-phenyl)-3H-imidazol-4-yl]-methyl-amine In a 25 mL flask, [2-(4-Bromo-2,6-difluoro-benzylsulfanyl)-3-(4-fluoro-phenyl)-3H-imidazol-4-yl]-(3,4-dimethoxy-phenyl)-methyl-amine (600 mg), dimethylpropargylamine (172 μL), pyrrolidine (133 μL) are added in 5 mL of dry and degassed DMF. Then, PdCl$_2$(dppf)$_2$ (68 mg) and CuI (20 mg) are added. Reaction mixture is heated under argon at 80° C. for 6 h. Reaction mixture is cooled down to room temperature, diluted with EtOAc, washed with brine, dried over Na$_2$SO$_4$ and evaporated. Crude product is purified by flash chromatography (DCM/cHex then DCM/MeOH), to give 281 mg of a white powder (47%).

MS [M+H]$^+$ m/z=566.9

$^1$H-NMR (CDCl$_3$): δ (ppm) 2.35 (s, 6H); 2.91 (s, 3H); 3.45 (s, 2H); 3.79 (s, 3H); 3.82 (s, 3H); 4.08 (s, 2H); 6.15 (Dd, 1H, J=2.7 Hz, J=8.7 Hz); 6.28 (d, 1H, J=2.7 Hz); 6.72 (d, 1H, J=8.7 Hz); 6.87 (d, 2H, J=8.0 Hz); 6.97 (m, 4H); 7.02 (s, 1H)

Step 8 (Example 7)

(3-{4-[5-[(3,4-Dimethoxy-phenyl)-methyl-amino]-1-(4-fluoro-phenyl)-1H-imidazol-2-ylsulfanylmethyl]-3,5-difluoro-phenyl}-prop-2-ynyl)-trimethyl-ammonium iodide In a 25 mL flask are added (3,4-Dimethoxy-phenyl)-[2-[4-(3-dimethylamino-prop-1-ynyl)-2,6-difluoro-benzylsulfanyl]-3-(4-fluoro-phenyl)-3H-imidazol-4-yl]-methyl-amine (254 mg), and 5 mL of a mixture dry Et$_2$O/dry THF 1:1. Iodomethane (27.7 μL) is then added, and reaction mixture is stirred at room temperature. After 1 h30 and 4 h, iodomethane (27.7 μL) is added again. Reaction mixture is then evaporated to dryness. Residue is triturated in Et$_2$O, filtrated, and the residue is purified by preparative HPLC (pH 3.8) to give 55 mg of the titled product as a brown residue (17%).

MS [M]$^+$m/z=581.3

$^1$H-NMR (DMSO-d6): δ (ppm) 2.92 (s, 3H); 3.21 (s, 9H); 3.64 (s, 3H); 3.65 (s, 3H); 4.01 (s, 2H); 4.68 (s, 2H); 6.06 (dd, J=2.8 Hz, J=8.8 Hz, 1H); 6.21 (d, J=2.7 Hz, 1H); 6.75 (d, J=8.8 Hz, 1H); 6.95 (s, 1H); 7.13-7.25 (m, 4H); 7.40 (m, 2H).

$^{13}$C-NMR (DMSO-d6): δ (ppm) 26.2; 52.7; 52.9; 55.9; 56.7; 80.7; 88.1; 100.1; 105.6; 113.8; 115.6; 116.3; 116.5; 122.0; 124.4; 130.2; 131.5; 136.5; 140.4; 142.6; 143.4; 149.8; 160.6; 162.2.

Step 8 (Example 8)

(3-{4-[5-[(3,4-Dimethoxy-phenyl)-methyl-amino]-1-(4-fluoro-phenyl)-1H-imidazol-2-ylsulfanylmethyl]-3,5-difluoro-phenyl}-prop-2-ynyl)-trimethyl-ammonium formate (3,4-Dimethoxy-phenyl)-[2-[4-(3-dimethylamino-prop-1-ynyl)-2,6-difluoro-benzylsulfanyl]-3-(4-fluoro-phenyl)-3H-imidazol-4-yl]-methyl-amine (365 mg) is dissolved in 6.4 mL of a mixture of dry Et$_2$O/THF (1/1), under argon, and iodomethane (80 μL) are then added. Mixture is stirred at room temperature. After 1 h30 iodomethane (80 μL) is added again. After 30 min, reaction is evaporated to dryness.

Residue is then purified twice by preparative HPLC (HCOOH 0.1% first, then pH 9.2). 75 mg (19%) of a yellowish powder, corresponding o the titled product are then obtained.

MS [M]$^+$ m/z=581.1

$^1$H-NMR (CDCl$_3$): δ (ppm) 2.94 (s, 3H); 3.45 (s, 9H); 3.78-3.80 (m, 6H); 4.01 (s, 2H); 4.87 (s, 2H); 6.16 (dd, J=2.7 Hz, J=8.7 Hz, 1H); 6.27 (d, J=2.7 Hz); 6.71 (d, J=8.7 Hz); 6.96-7.07 (m, 7H); 8.58 (s, 1H).

$^{13}$C-NMR (CDCl$_3$): δ (ppm) 25.7; 40.3; 53.1; 55.9; 56.4; 56.8; 89.1; 100.2; 106.0; 112.4; 115.2 (d, J=27.0 Hz); 116.1 (d, J=22.7 Hz); 116.5 (t, J=19.8 Hz); 121.4 (t, J=12.5 Hz); 124.1; 129.2 (d, J=9.0 Hz); 130.8 (d; J=3.2 Hz); 137.1; 140.2; 142.8; 143.0; 149.5; 160.7 (dd, J=9.1 Hz, J=251.3 Hz); 162.4 (d, J=249.1 Hz).

Synthesis of Intermediate 2

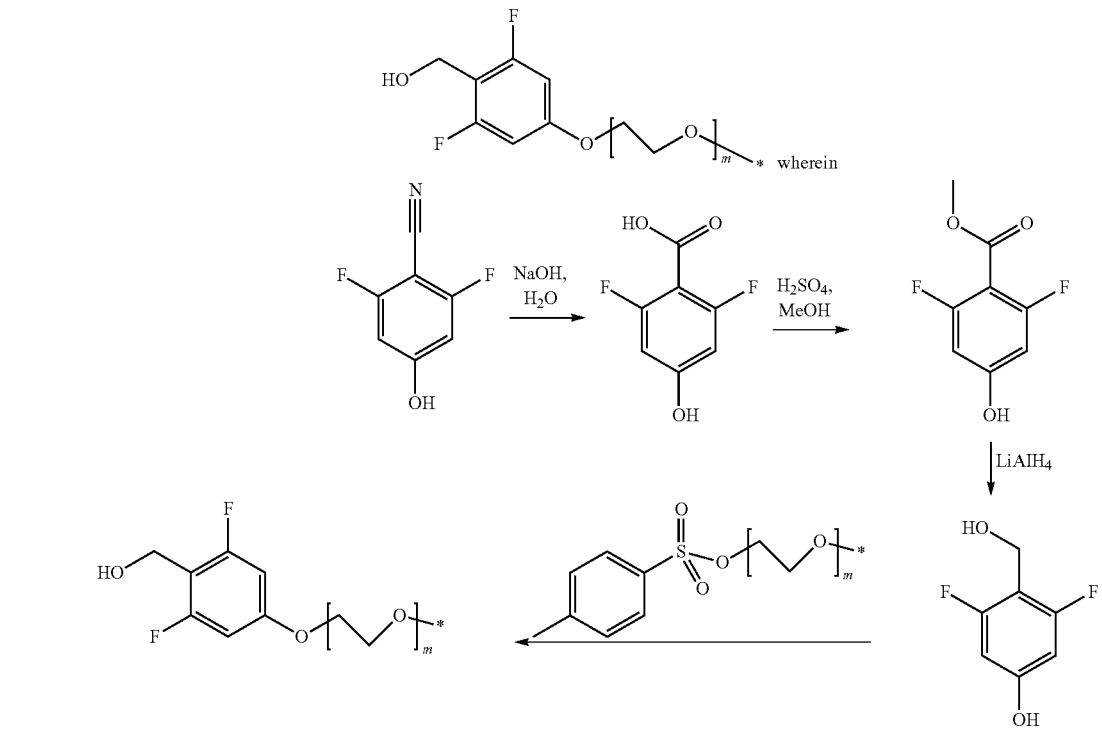

m = 9-13

2,6-Difluoro-4-hydroxy-benzoic acid 2,6-Difluoro-4-hydroxy-benzonitrile (1.5 g) is dissolved in 7 mL distilled water and a solution of 1.35 g of NaOH in 4 mL water is then added. Reaction mixture is then heated at reflux for 4 days. Heating is then stopped, and reaction mixture is acidified by adding concentrated HCl, and extracted with Et$_2$O. Organic phase is then extracted by saturated NaHCO$_3$ aq. This aqueous solution is then acidified by adding concentrated HCl, and then extracted by Et$_2$O. Organic phase is dried over Na$_2$SO$_4$, and evaporated, to give 1.58 g of a white solid corresponding to the expected acid (94%).

MS [M−H]$^−$ m/z=172.9

$^1$H-NMR (DMSO-d6): δ (ppm); 6.49 (m, 2H); 10.96 (brs, 1H); 13.20 (brs, 1H)

2,6-Difluoro-4-hydroxy-benzoic acid methyl ester 2,6-difluoro-4-hydroxy-benzoic acid (1.58 g) is dissolved in 18 mL Methanol, concentrated sulphuric acid (257 μL) is then added, and reaction mixture is heated at reflux overnight.

Reaction mixture is then evaporated, and residue is dissolved in EtOAc, washed twice by water, brine, dried over Na$_2$SO$_4$ and evaporated to give 1.48 g of the expected product as a white powder (90%).

MS [M−H]$^−$ m/z=187.1

$^1$H-NMR (DMSO-d6): δ (ppm) 3.80 (s, 3H); 6.54 (m, 2H); 11.12 (s, 1H)

3,5-Difluoro-4-hydroxymethyl-phenol

In a 100 mL flask are added 2,6-Difluoro-4-hydroxy-benzoic acid methyl ester (1.48 g), 26 mL anhydrous THF, and 34 mL of a 1M solution of DIBALH in cyclohexane at 0-5° C. Reaction mixture is then stirred at this temperature for 1.5h, and then poured into a 250 mL flask containing 27 mL of cold (0-5° C.) 1M aqueous potassium sodium L-tartrate solution. Reaction mixture is stirred at room temperature for 30 min. Aqueous phase is extracted by EtOAc, and combined organic phases are then washed with brine, dried over Na$_2$SO$_4$, and evaporated. Aqueous phase is acidified to pH 5, and extracted by EtOAc. Organic phase is dried over Na$_2$SO$_4$ and evaporated. The yellowish powders obtained are pulled together. 1 g of the expected product is obtained (80%).

MS [M−H]$^−$ m/z=159.0

$^1$H-NMR (DMSO-d6): δ (ppm) 4.36 (d, 2H, J=5.2 Hz); 5.00 (t, 1H, J=5.5 Hz); 6.41 (m, 2H); 10.28 (s, 1H)

4-methylbenzenesulfonic acid methoxy-polyethyleneglycyl ester (average MW=627 g/mol)

Polyethyleneglycol methyl ether (1.5 g) (mean MW=500 g/mol) is dissolved in dry THF (10 mL). The solution is cooled at 0° C. NaH 60% (w/w) (180 mg) is added and the reaction mixture is stirred at 0° C. to 20° C. for 2 h. Then tosyl chloride (1.14 g) is added at 0° C. and reaction mixture was stirred at RT for 24 hours. Reaction mixture is then evaporated, and residue is purified by flash chromatography (DCM/MeOH) to give 1.68 g of a colorless oil corresponding to the clean expected product (89%).

MS [M+H$_3$O]$^+$ m/z=644.3 (n=10)

$^1$H-NMR (DMSO-d6): δ (ppm) 2.41 (s, 3H); 3.23 (s, 3H); 3.44-3.49 (m, 36H); 3.57 (m, 2H); 4.10 (m, 2H); 7.48 (d, 2H, J=8.0 Hz); 7.78 (d, 2H, J=8.3 Hz).

[2,6-Difluoro-4-(methoxy-polyethyleneglycoxy)-phenyl]-methanol (Average MW=615 g/mol)

4-methylbenzenesulfonic acid methoxy-polyethyleneglycyl ester (1.5 mmol, 981 mg) is dissolved in MeCN (5 mL), 3,5-Difluoro-4-hydroxymethyl-phenol (1.80 mmol, 288 mg) and K2CO3 (1.80 mmol, 249 mg) are added, and reaction mixture is stirred overnight under reflux. Reaction mixture is then cooled down, and filtered. The filtrate is concentrated under vaccuum and purified by Flash Chromatography (DCM/MeOH) to give 676 mg of an uncolored oil (73%).

MS [M+H$_3$O]$^+$ m/z=632.2 (n=10)

$^1$H-NMR (DMSO-d6): δ (ppm) 3.23 (s, 3H); 3.41-3.56 (m, 42H); 3.72 (m, 2H); 4.11 (m, 2H); 4.40 (d, 2H, J=5.5 Hz); 5.08 (t, 1H, J=5.5 Hz); 6.71 (m, 2H).

EXAMPLE 9

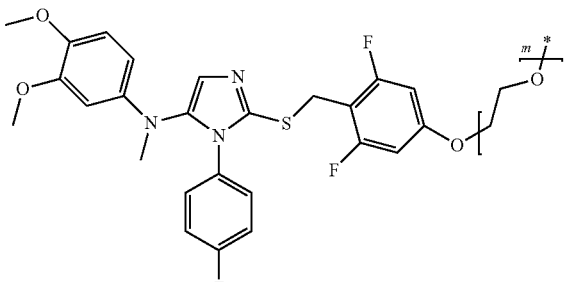

mixture m = 9-13

Step 5

2-[2-[2,6-Difluoro-4-(methoxy-polyethyleneglycoxy)-benzyl]-3-(4-fluoro-phenyl)-isothioureido]-N-(3,4-dimethoxy-phenyl)-N-methyl-acetamide (Average MW=1012.7 g/mol)

[2,6-Difluoro-4-(methoxy-polyethyleneglycoxy)-phenyl]-methanol (676 mg) and TEA (156 µL) are dissolved in dry DCM at 0° C. Mesylchloride (82 µL) is then added dropwise, and the mixture is stirred at room temperature overnight. TEA (47 µL) and mesylchloride (25 µL) are then added. After 1 hour, TEA (156 µL) and mesylchloride (82 µL) are added again. After 3 hours, TEA (47 µL) is added again. Reaction mixture is then evaporated to dryness. This residue is added to a 25 mL flask loaded with N-(3,4-Dimethoxy-phenyl)-2-[3-(4-fluoro-phenyl)-isothioureido]-N-methyl-acetamide (397 mg), K$_2$CO$_3$ (45 mg), NaI (79 mg), and 4 mL of acetonitrile. The suspension is stirred at room temperature for 14 hours. Reaction mixture is then evaporated, and purified by flash chromatography (cHex/DCM then DCM MeOH) to give 499 mg of a brown oil (47%).

MS [M+H+H$_3$O]$^{2+}$ m/z=518.4 (n=10)

Step 6

[2-[2,6-Difluoro-4-(2-methoxy-polyethyleneglycoxy)-benzylsulfanyl]-3-(4-fluoro-phenyl)-3H-imidazol-4-yl]-(3,4-dimethoxy-phenyl)-methyl-amine (Average MW=972.1 g/mol, m=9-13)

The titled compound is obtained as a orange oil (75 mg, 16%) following Procedure B, using 2-[2-[2,6-Difluoro-4-(methoxy-polyethyleneglycoxy)-benzyl]-3-(4-fluoro-phenyl)-isothioureido]-N-(3,4-dimethoxy-phenyl)-N-methyl-acetamide (499 mg). Purification was performed by preparative HPLC.

MS [M+H+H$_3$O]$^{2+}$ m/z=487.2 (n=10)

$^1$H-NMR (DMSO-d6): δ (ppm) 2.92 (s, 3H); 3.23 (s, 3H); 3.42-3.55 (m, 42H); 3.63-3.64 (m, 6H); 3.70-3.73 (m, 2H); 3.99 (s, 2H); 4.09-4.12 (m, 2H); 6.06 (dd, J=2.7 Hz, J=8.6 Hz, 1H); 6.21 (d, J=2.7 Hz, 1H); 6.67-6.70 (m, 2H); 6.75 (d, J=8.8 Hz, 1H); 6.96 (s, 1H); 7.09-7.22 (m, 4H).

$^{13}$C-NMR (DMSO-d6): δ (ppm) 26.1; 55.9; 56.5; 58.5; 68.6; 69.0; 70.0; 70.2; 70.3; 71.7; 99.1 (d, J=28.0 Hz); 99.9; 105.4 (t); 105.5; 113.7; 116.3 (d, J=22.9 Hz); 124.3; 130.0 (d, J=9.0 Hz); 131.5 (d, J=3.6 Hz); 137.3; 140.1; 142.5; 143.4; 149.7; 161.3 (dd); 162.1 (d)

General Route Toward
5-amino-3-thio-[1,2,4]triazole Derivatives

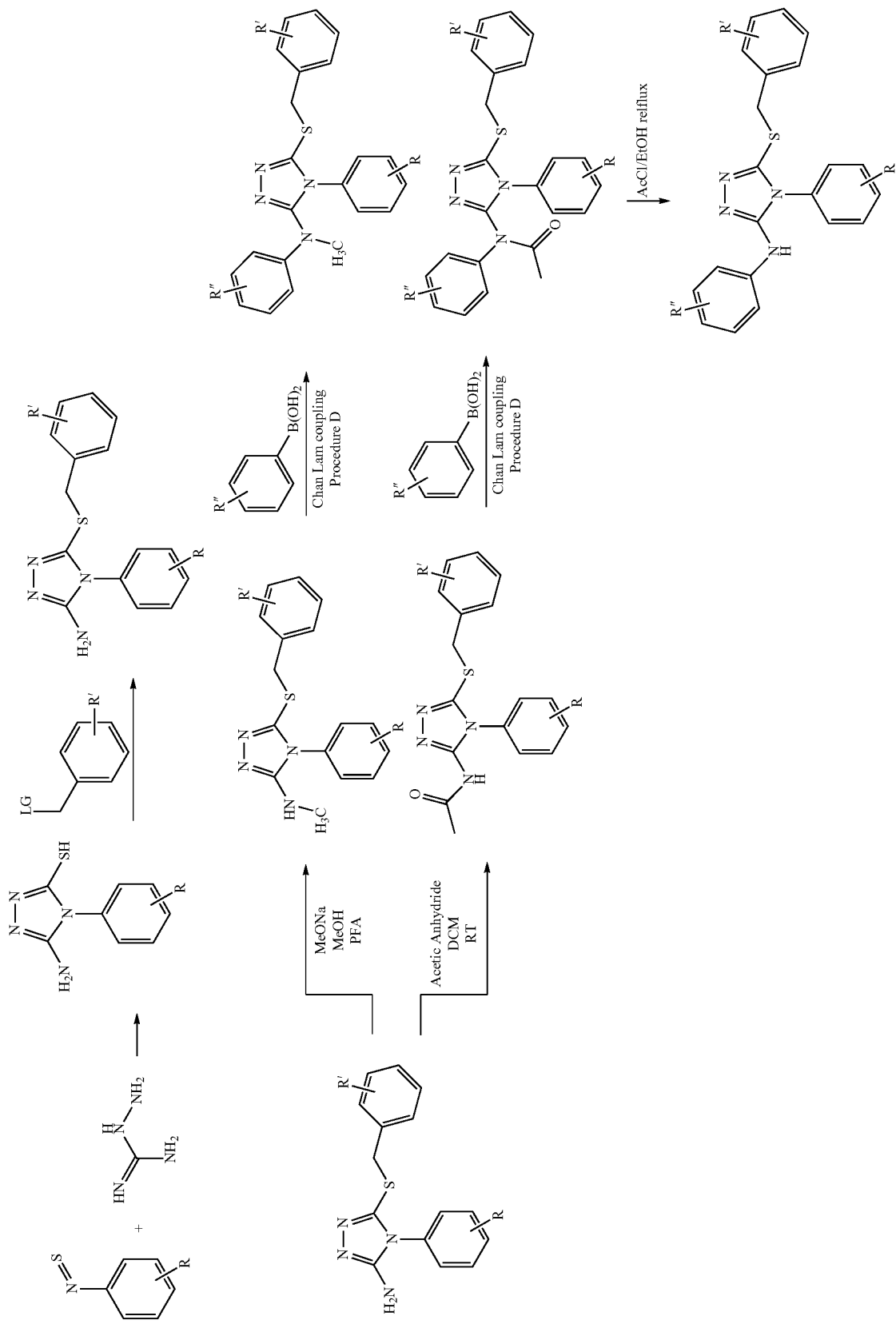

Procedure D

The thio-triazolyl-amine derivative (1 eq) and the phenylboronic acid derivative (1 eq) are dissolved in dichloromethane (QS 20 mM). Molecular sieve 4 Å, pyridine (2 eq) and copper$^{(II)}$ acetate (Cu(OAc)$_2$) (1.5 eq) are added to the solution. Reaction mixture is stirred at room temperature for several hours. Pyridine, phenylboronic acid derivative, and Cu(OAc)$_2$ are added several time until satisfying conversion. Reaction mixture is then filtered on Celite. Filtrate is washed by water, and saturated NaHCO$_3$ aq. Organic phase is dried over MgSO$_4$, and evaporated to dryness. Residue is purified by flash chromatography (DCM/MeOH).

Synthesis of Intermediate 3

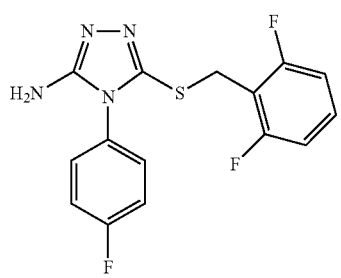 [SMILES: Nc1nnc(SCc2c(F)cccc2F)n1-c1ccc(F)cc1]

5-Amino-4-(4-fluoro-phenyl)-4H-[1,2,4]triazole-3-thiol 4-fluorophenylisothiocyanate (1.04 g, 6.54 mmol), aminoguanidinium chloride (1.45 g, 13.1 mmol), diisopropylethylamine (3.12 mL, 19.6 mmol) are dissolved in DMF (9.40 mL). Reaction mixture is stirred at 50° C. for 15 h, then evaporated to dryness. 13 mL of NaOH aq 2M are then added, and reaction mixture is stirred at 50° C. for 18 hours. Suspension is then filtered, and filtrate is neutralized by addition of HCl aq 2M and filtrated. Both precipitates are pulled together, to give 1.2 g of an orange powder (87%).

MS [M+H]$^+$ m/z=210.9

$^1$H-RMN (DMSO-d6): δ (ppm) 5.96 (s, 2H); 7.38 (m, 4H); 12.80 (s)

5-(2,6-Difluoro-benzylsulfanyl)-4-(4-fluoro-phenyl)-4H-[1,2,4]triazol-3-ylamine

5-Amino-4-(4-fluoro-phenyl)-4H-[1,2,4]triazole-3-thiol (501 mg, 2.38 mmol), 2-Bromomethyl-1,3-difluoro-benzene (492 mg, 2.37 mmol), DIEA (416 µL, 2.62 mmol) are dissolved in 12 mL dichloromethane. Reaction mixture is stirred at room temperature for 3 hours, then washed with water and brine, and organic phase is dried over MgSO$_4$, and evaporated to dryness to give 787 mg of the expected product as a white powder (98%).

MS [M+H]$^+$ m/z=336.9

$^1$H-RMN (DMSO-d6): δ (ppm) 3.88 (s, 2H); 5.89 (s, 2H); 7.03 (pseudo-t, 2H, J=8.0 Hz); 7.32 (m, 5H)

EXAMPLE 10

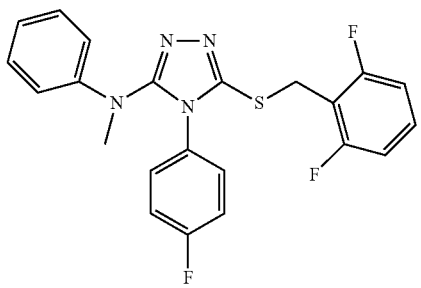 [SMILES: CN(c1ccccc1)c1nnc(SCc2c(F)cccc2F)n1-c1ccc(F)cc1]

[5-(2,6-Difluoro-benzylsulfanyl)-4-(4-fluoro-phenyl)-4H-[1,2,4]triazol-3-yl]-methyl-amine A suspension of 5-(2,6-Difluoro-benzylsulfanyl)-4-(4-fluoro-phenyl)-4H-[1,2,4]triazol-3-ylamine (200 mg, 595 µmol) and MeONa (161 mg, 2.98 mmol) in 610 µL methanol is added to a suspension of paraformaldehyde (25 mg, 833 µmol) in 580 µL methanol. Reaction mixture is stirred at room temperature for 16 hours. NaBH$_4$ (22.5 mg, 595 µmol) is then added, and reaction mixture is stirred at reflux for 30 min. After cooling down to room temperature, reaction mixture is partially evaporated. KOH aq 1M (5 mL) are then added. This solution is then extracted by EtOAc. Organic phase is dried over MgSO$_4$, and evaporated to dryness. Residu is purified by flash chromatography h (DCM/MeOH), to give 157.6 mg of the expected product as a yellowish solid (76%).

MS [M+H]$^+$ m/z=350.9

$^1$H-RMN (DMSO-d6): δ (ppm) 2.73 (d, 3H, J=4.8 Hz); 3.91 (s, 2H); 5.82 (q, 1H, J=4.7 Hz); 7.04 (pseudo-t, 2H, J=8.0 Hz); 7.25-7.43 (m, 5H).

[5-(2,6-Difluoro-benzylsulfanyl)-4-(4-fluoro-phenyl)-4H-[1,2,4]triazol-3-yl]-methyl-phenyl-amine The titled compound is obtained as a yellowish solid (46 mg, 13%) after purification by preparative HPLC, following procedure D using [5-(2,6-Difluoro-benzylsulfanyl)-4-(4-fluoro-phenyl)-4H-[1,2,4]triazol-3-yl]-methyl-amine (281 mg, 800 µmol) and phenylboronic acid.

MS [M+H]$^+$ m/z=426.8

EXAMPLE 11

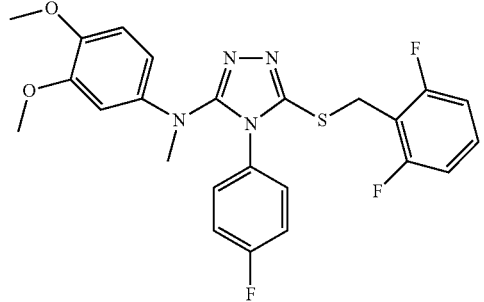 [SMILES: COc1ccc(N(C)c2nnc(SCc3c(F)cccc3F)n2-c2ccc(F)cc2)cc1OC]

[5-(2,6-Difluoro-benzylsulfanyl)-4-(4-fluoro-phenyl)-4H-[1,2,4]triazol-3-yl]-(3,4-dimethoxy-phenyl)-methyl-amine The titled compound is obtained as a yellowish solid (42.4 mg, 11%) after purification by preparative HPLC, following procedure 9 using [5-(2,6-Difluoro-benzylsulfanyl)-4-(4-fluoro-phenyl)-4H-[1,2,4]triazol-3-yl]-methyl-amine (281 mg, 800 µmol) and 3,4-dimethoxyphenylboronic acid.

MS [M+H]$^+$ m/z=486.9

$^1$H-RMN (CDCl$_3$): δ (ppm) 2.69 (s, 3H); 3.92 (s, 3H); 3.95 (s, 3H); 4.26 (s, 2H); 6.84-6.94 (m, 3H); 7.10-7.42 (m, 7H)

EXAMPLE 12

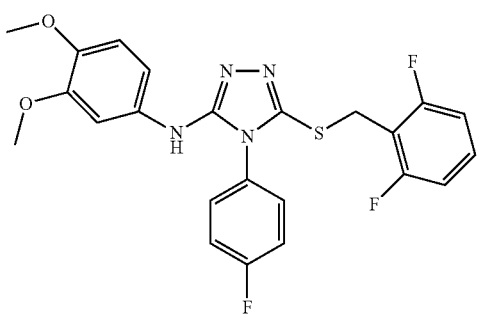 [SMILES: COc1ccc(Nc2nnc(SCc3c(F)cccc3F)n2-c2ccc(F)cc2)cc1OC]

N-[5-(2,6-Difluoro-benzylsulfanyl)-4-(4-fluoro-phenyl)-4H-[1,2,4]triazol-3-yl]-acetamide 5-(2,6-Difluoro-benzylsulfanyl)-4-(4-fluoro-phenyl)-4H-[1,2,4]triazol-3-ylamine (318 mg, 94.5 µmol) is dissolved in 0.5 mL dichloromethane, acetic anhydride (450 µL, 4.73 mmol) is then added. Reaction mixture is stirred at room temperature for 30 min. 5 mL of NaHCO$_3$ aq 2N are then added. Phases are separated, and organic phase is dried over MgSO$_4$, and evaporated to dryness. Residue is recrystallized in isopropanol to give 238 mg of the expected product as white crystals (66%).

MS [M+H]$^+$ m/z=378.9

$^1$H-RMN (DMSO-d6): δ (ppm) 1.84 (s, 3H); 4.19 (s, 2H); 7.05 (pseudo-t, 2H, J=8.0 Hz); 7.33 (m, 5H); 10.37 (brs, 1H).

N-[5-(2,6-Difluoro-benzylsulfanyl)-4-(4-fluoro-phenyl)-4H-[1,2,4]triazol-3-yl]-N-(3,4-dimethoxy-phenyl)-acetamide The titled compound is obtained as a yellowish oil (420 mg, 50%) following procedure D, using N-[5-(2,6-Difluoro-benzylsulfanyl)-4-(4-fluoro-phenyl)-4H-[1,2,4]triazol-3-yl]-acetamide (570 mg, 1.5 mmol), and 3,4-dimethoxyphenylboronic acid.

MS [M+H]$^+$ m/z=514.9

$^1$H-RMN (DMSO-d6): δ (ppm) 1.65 (s, 3H); 3.79 (s, 3H); 3.81 (s, 3H); 4.31 (s, 2H); 7.05-7.18 (m, 3H); 7.24-7.54 (m, 7H)

[5-(2,6-Difluoro-benzylsulfanyl)-4-(4-fluoro-phenyl)-4H-[1,2,4]triazol-3-yl]-(3,4-dimethoxy-phenyl)-amine Acetyl chloride (2.4 mL) and ethanol (5 mL) are gently mixed at 0-5° C., and the mixture is added to a solution of N-[5-(2,6-Difluoro-benzylsulfanyl)-4-(4-fluoro-phenyl)-4H-[1,2,4]triazol-3-yl]-N-(3,4-dimethoxy-phenyl)-acetamide (310 mg, 602 µmol) in 4.6 mL ethanol. Reaction mixture is then heated at 100° C. for 30 min. Reaction mixture is then evaporated; residue is dissolved in EtOAc, washed by water, and saturated NaHCO$_3$ $_{aq3}$. Organic phase is dried over MgSO$_4$, and evaporated to dryness. Residue is recrystallized in isopropanol/methanol to give 163.5 mg of the expected product as a white solid (57%).

MS [M+H]$^+$ m/z=472.9

$^1$H-RMN (DMSO-d6): δ (ppm) 3.77 (s, 3H); 3.78 (s, 3H); 4.22 (s, 2H); 5.13 (brs, 1H); 7.00 (d, 1H, J=8.8 Hz); 7.35-7.55 (m, 7H).

EXAMPLE 13

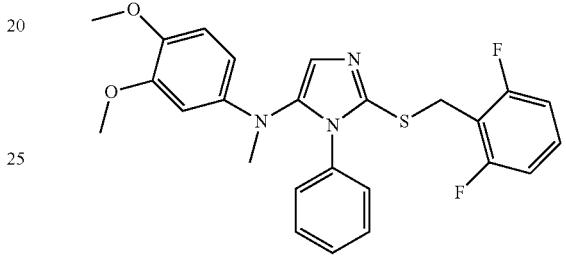

Step 4 of General route toward 5-amino-2-thio-imidazole derivatives

N-(3,4-Dimethoxy-phenyl)-N-methyl-2-(3-phenyl-isothioureido)-acetamide

Phenylisothiocyanate (159.5 µL, 1.33 mmol) and TEA (216 µL, 1.60 mmol) are added in a 100 mL flask in 2 mL Ethanol. Residue from [2-(3,4-dimethoxy-N-methyl-anilino)-2-oxo-ethyl]ammonium formate (Intermediate 1c) (400 mg, 1.33 mmol) is dissolved in 16 mL of ethanol, TEA (180 µL, 1.33 mmol) is added, and the mixture is added dropwise at RT. After the addition, the reaction is over. Reaction mixture is evaporated to dryness, and purified by flash chromatography (pure cyclohexane to DCM/MeOH 99.5/0.5), to give the titled product as a yellowish residue (162 mg, 34%).

MS [M+H]$^+$ m/z=359.9

Step 5

2-[2-(2,6-Difluoro-benzyl)-3-phenyl-isothioureido]-N-(3,4-dimethoxy-phenyl)-N-methyl-acetamide In a 25 mL flask are added N-(3,4-Dimethoxy-phenyl)-N-methyl-2-(3-phenyl-isothioureido)-acetamide (162 mg, 450 µmol), Potassium Carbonate (62 mg, 450 µmol), sodium Iodide (34 mg, 225 µmol), and 2.5 mL of acetonitrile. The suspension is stirred at room temperature for 10 min, and 2-(bromomethyl)-1,3-difluoro-benzene (93 mg, 450 µmol) is then added. The suspension is stirred at room temperature for hours. The medium is then evaporated, residue is dissolved in EtOAc, washed with water and brine, organic phase is dried over Na$_2$SO$_4$ and evaporated to dryness to give the titled product as a yellowish solid (183 mg, 84%).

MS [M+H]+ m/z=486.0

1H-NMR (CDCl3): δ (ppm) 3.27 (s, 3H); 3.81-3.87 (m, 8H); 4.12 (s, 2H); 6.68-7.21 (m, 11H).

Step 6

[2-(2,6-Difluoro-benzylsulfanyl)-3-phenyl-3H-imidazol-4-yl]-(3,4-dimethoxy-phenyl)-methyl-amine 2-[2-(2,6-Difluoro-benzyl)-3-phenyl-isothioureido]-N-(3,4-dimethoxy-phenyl)-N-methyl-acetamide (183 mg, 0.38 mmol) is dissolved in 3.8 mL of ethyl acetate. Diisopropylethylamine (395 μL, 2.26 mmol), and T3P® in EtOAc (666 μL, 1.13 mmol) are then added. The mixture is heated with microwave at 150° C. for 10 min. Reaction mixture is then diluted with EtOAc, washed by an aqueous saturated solution of NaHCO3, and by brine. Organic phase is then dried over Na2SO4 and evaporated. Residue is then purified by flash chromatography (cHex to cHex/EtOAc 85/15), and then again by flash chromatography (cHex/DCM 1/1 to DCM/MeOH 99/1) to give the titled product as a reddish solid (21 mg, 11%).

MS [M+H]+ m/z=467.9

1H-NMR (CDCl3): δ (ppm) 2.90 (s, 3H); 3.80 (s, 3H); 3.82 (s, 3H); 4.18 (s, 2H); 6.17 (dd, 1H, J=8.7 Hz, J=2.8 Hz); 6.31 (d, 1H, J=2.8 Hz); 6.70-6.83 (m, 3H); 6.99-7.04 (m, 3H); 7.18 (m, 1H); 7.25-7.32 (m, 3H).

13C-NMR (CDCl3): δ (ppm) 25.7; 40.0; 55.9; 56.5; 99.8; 105.3; 111.3 (m); 112.4; 113.6 (t, J=19.4 Hz); 124.2; 127.3; 128.7; 128.9; 129.1 (t, J=9.9 Hz); 134.9; 138.3; 139.5; 142.6; 143.3; 149.6; 161.3 (dd, J=249.8 Hz, J=7.4 Hz).

EXAMPLE 14

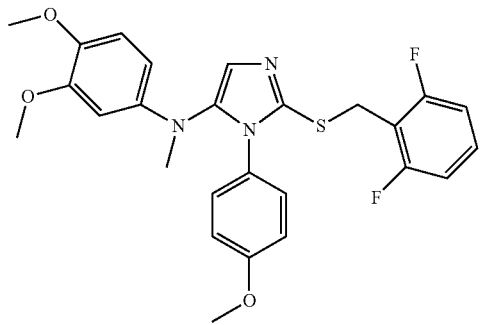 [SMILES: COc1ccc(-n2c(N(C)c3ccc(OC)c(OC)c3)cnc2SCc2c(F)cccc2F)cc1]

Step 4 of General route toward 5-amino-2-thio-imidazole derivatives

N-(3,4-Dimethoxy-phenyl)-2-[3-(4-methoxy-phenyl)-isothioureido]-N-methyl-acetamide 4-methoxyphenylisothiocyanate (184.0 μL, 1.33 mmol) and TEA (216 μL, 1.60 mmol) are added in a 100 mL flask in 2 mL Ethanol. [2-(3,4-dimethoxy-N-methyl-anilino)-2-oxo-ethyl]ammonium formate (Intermediate 1c) (400 mg, 1.33 mmol) is dissolved in 16 mL of ethanol, TEA (180 μL, 1.33 mmol) is added, and the mixture is added dropwise at room temperature. After the addition, the reaction is over. Reaction mixture is evaporated to dryness, and purified by flash chromatography (pure cyclohexane to DCM/MeOH 99/1), to give the titled product as a yellowish powder (157 mg, 30%).

MS [M+H]+ m/z=389.9

Step 5

2-[2-(2,6-Difluoro-benzyl)-3-(4-methoxy-phenyl)-isothioureido]-N-(3,4-dimethoxy-phenyl)-N-methyl-acetamide In a 25 mL flask are added N-(3,4-Dimethoxy-phenyl)-2-[3-(4-methoxy-phenyl)-isothioureido]-N-methyl-acetamide (157 mg, 400 μmol), Potassium Carbonate (56 mg, 400 μmol), sodium Iodide (30 mg, 200 μmol), and 2 mL of acetonitrile. The suspension is stirred at room temperature for 10 min, and 2-(bromomethyl)-1,3-difluoro-benzene (83 mg, 400 μmol) is then added. The suspension is stirred at room temperature for 16 hours. The medium is then evaporated, residue is dissolved in EtOAc, washed with water and brine, organic phase is dried over Na2SO4 and evaporated to dryness to give the titled product as an orange solid (170 mg, 82%).

MS [M+H]+ m/z=516.0

1H-NMR (CDCl3): δ (ppm) 3.28 (s, 3H); 3.71 (s, 3H); 3.82-3.88 (m, 8H); 4.12 (s, 2H); 6.70-6.85 (m, 9H); 7.17 (m, 1H).

Step 6

[2-(2,6-Difluoro-benzylsulfanyl)-3-(4-methoxy-phenyl)-3H-imidazol-4-yl]-(3,4-dimethoxy-phenyl)-methyl-amine 2-[2-(2,6-Difluoro-benzyl)-3-(4-methoxy-phenyl)-isothioureido]-N-(3,4-dimethoxy-phenyl)-N-methyl-acetamide (170 mg, 0.33 mmol) is dissolved in 3.3 mL of ethyl acetate. Diisopropylethylamine (346 μL, 1.98 mmol), and T3P® in EtOAc (583 μL, 0.98 mmol) are then added. The mixture is heated with microwave at 150° C. for 10 min. Reaction mixture is then diluted with EtOAc, washed by an aqueous saturated solution of NaHCO3, and by brine. Organic phase is then dried over Na2SO4 and evaporated. Residue is then purified by flash chromatography (cHex to cHex/EtOAc 85/15), to give the titled product a reddish solid (77 mg, 46%).

MS [M+H]+ m/z=498.0

1H-NMR (CDCl3): δ (ppm) 2.91 (s, 3H); 3.77 (s, 3H); 3.80-3.81 (m, 6H); 4.17 (s, 2H); 6.16 (dd, 1H, J=8.7 Hz, J=2.8 Hz); 6.30 (d, 1H, J=2.7 Hz); 6.70-6.83 (m, 5H); 6.93 (m, 2H); 7.01 (s, 1H); 7.18 (m, 1H).

13C-NMR (CDCl3): δ (ppm) 25.6; 39.9; 55.4; 55.9; 56.5; 99.6; 105.1; 111.2 (m); 112.4; 113.6 (t, J=19.6 Hz); 114.1; 124.2; 127.5; 128.5; 129.1 (t, J=10.4 Hz); 138.6; 139.6; 142.4; 143.4; 149.5; 159.5; 161.2 (dd, J=250.1 Hz, J=7.9 Hz).

EXAMPLE 15

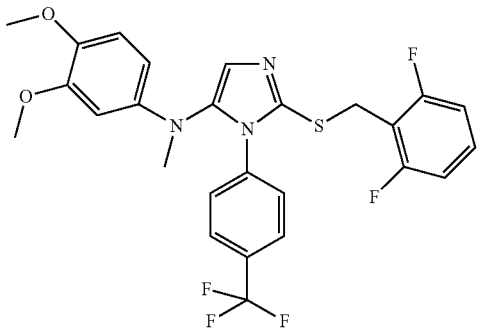 [SMILES: COc1ccc(N(C)c2cnc(SCc3c(F)cccc3F)n2-c2ccc(C(F)(F)F)cc2)cc1OC]

Step 4 of General Route Toward
5-amino-2-thio-imidazole Derivatives

N-(3,4-Dimethoxy-phenyl)-N-methyl-2-[3-(4-trifluoromethyl-phenyl)-isothioureido]-acetamide 4-(trifluomethyl)phenylisothiocyanate (332 mg, 1.63 mmol) and TEA (264 µL, 1.96 mmol) are added in a 100 mL flask in 2 mL Ethanol. [2-(3,4-dimethoxy-N-methyl-anilino)-2-oxo-ethyl]ammonium formate (Intermediate 1c) (490 mg, 1.63 mmol) is dissolved in 18 mL of ethanol, TEA (220 µL, 1.63 mmol) is added, and the mixture is added dropwise at RT. After the addition, the reaction is over. Reaction mixture is evaporated to dryness, and purified by flash chromatography (pure cyclohexane to cHex/EtOAc 6/4), to give the titled product as a yellowish powder (352 mg, 50%).

MS [M+H]+ m/z=427.9

1H-NMR (DMSO-d6): δ (ppm) 3.18 (s, 3H); 3.78 (s, 3H); 3.79 (s, 3H); 4.02 (d, 2H, J=3.8 Hz); 6.93 (dd, 1H, J=2.2 Hz, J=8.5 Hz); 7.01-7.06 (m, 2H); 7.65 (d, 2H, J=8.6 Hz); 7.80 (d, 2H, J=8.6 Hz); 8.08 (s, 1H); 10.3 (s, 1H).

Step 5

2-[2-(2,6-Difluoro-benzyl)-3-(4-trifluoromethyl-phenyl)-isothioureido]-N-(3,4-dimethoxy-phenyl)-N-methyl-acetamide In a 25 mL flask are added N-(3,4-Dimethoxy-phenyl)-N-methyl-2-[3-(4-trifluoromethyl-phenyl)-isothioureido]-acetamide (352 mg, 820 µmol), Potassium Carbonate (114 mg, 820 µmol), sodium Iodide (62 mg, 410 µmol), and 4.1 mL of acetonitrile. The suspension is stirred at room temperature for 10 min, and 2-(bromomethyl)-1,3-difluorobenzene (170 mg, 820 µmol) is then added. The suspension is stirred at room temperature for 16 hours. The medium is then evaporated, residue is dissolved in EtOAc, washed with water and brine, organic phase is dried over Na2SO4 and evaporated to dryness to give the titled product as an orange solid (438 mg, 96%).

MS [M+H]+ m/z=554.0

1H-NMR (DMSO-d6): δ (ppm) 3.16 (s, 3H); 3.68 (s, 3H); 3.76 (m, 5H); 4.21 (s, 2H); 6.77-6.88 (m, 3H); 6.95-6.99 (m, 2H); 7.05-7.11 (m, 3H); 7.39 (m, 1H); 7.49 (d, 2H, J=8.4 Hz).

Step 6

[2-(2,6-Difluoro-benzylsulfanyl)-3-(4-trifluoromethyl-phenyl)-3H-imidazol-4-yl]-(3,4-dimethoxy-phenyl)-methyl-amine 2-[2-(2,6-Difluoro-benzyl)-3-(4-trifluoromethyl-phenyl)-isothioureido]-N-(3,4-dimethoxy-phenyl)-N-methyl-acetamide (438 mg, 0.79 mmol) is dissolved in 8 mL of ethyl acetate. Diisopropylethylamine (829 µL, 4.75 mmol), and T3P® in EtOAc (1.40 mL, 2.37 mmol) are then added. The mixture is heated with microwave at 150° C. for 10 min. Reaction mixture is then diluted with EtOAc, washed by an aqueous saturated solution of NaHCO3, and by brine. Organic phase is then dried over Na2SO4 and evaporated. Residue is then purified by flash chromatography (cHex to cHex/EtOAc 85/15), to give the titled compound as an orange solid (166 mg, 39%).

MS [M+H]+ m/z=535.9

1H-NMR (CDCl3): δ (ppm) 2.92 (s, 3H); 3.80 (s, 3H); 3.83 (s, 3H); 4.16 (s, 2H); 6.19 (dd, J=8.7 Hz, J=2.7 Hz, 1H); 6.31 (d, J=2.7 Hz, 1H); 6.72 (d, J=8.8 Hz, 1H); 6.79 (m, 2H); 7.06 (s, 1H); 7.13 (d, J=8.3 Hz, 2H); 7.18 (m, 1H); 7.53 (d, J=8.3 Hz, 2H).

13C-NMR (CDCl3): δ (ppm) 26.3; 40.3; 56.0; 56.5; 100.2; 106.0; 111.4 (m); 112.5, 113.5 (t, J=19.3 Hz); 123.7 (q, J=271.3 Hz); 126.1 (q, J=10.1 Hz); 130.6 (q, J=32.6 Hz); 137.9; 138.0; 139.8; 143.0; 149.7; 161.2 (dd, J=250.0 Hz, J=7.4 Hz).

EXAMPLE 16

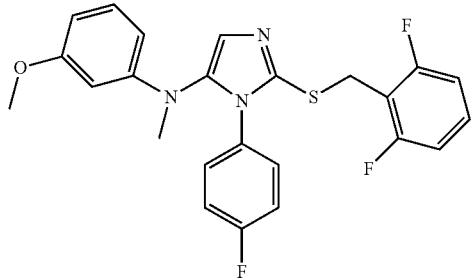 [SMILES: COc1cccc(N(C)c2cnc(SCc3c(F)cccc3F)n2-c2ccc(F)cc2)c1]

Step 1

3-methoxy-N-methyl-aniline

In a 25 mL flask are added 3-methoxyaniline (2.0 mmol, 0.224 mL) and sodium methoxide (10 mmol, 545 mg) in 3.5 mL of anhydrous methanol. Then, paraformaldehyde (4 mmol, 119 mg) is diluted in 1.5 mL of anhydrous methanol and the solution is added to the mixture. Molecular sieves (4 Angstroms) is then added and the mixture is stirred overnight at room temperature. The mixture is heated under reflux for 1 hour with sodium borohydride (2 mmol, 75.6 mg), then sodium borohydride (3.172 mmol, 120 mg) is added again and reaction mixture is stirred under reflux for 3 hour. The reaction mixture is filtered on Celite, evaporated, dissolved in EtOAc and water, and the two phases are separated. The aqueous phase is then basified by addition of saturated NaHCO3 aq, and extracted by EtOAc. The organic phase are washed by saturated NaHCO3 aq and by brine, dried over MgSO4, evaporated and dried under reduced pressure to give the expected product as a brown oil (266 mg, 96%).

MS: [M+H]$^+$ m/z=138.0

$^1$H-NMR (CDCl$_3$): δ (ppm) 2.84 (s, 3H); 3.78 (s, 3H); 6.19 (t, 1H, J=2.3 Hz); 6.26-6.31 (m, 2H); 7.10 (t, 1H, J=8.1 Hz).

Step 2' tert-butyl N-[2-(3-methoxy-N-methyl-anilino)-2-oxo-ethyl]carbamate

In a 25 mL flask is added 3-methoxy-N-methyl-aniline (1.554 mmol, 213 mg) in 1 mL of EtOAc. Then 2-(tert-butoxycarbonylamino)acetic acid (1.865 mmol, 326 mg), T3P (2.331 mmol, 1.374 mL) and DIEA (4.662 mmol, 814 μL) are added, and the mixture is stirred for 30 min at room temperature. Then the reaction mixture is diluted with ethyl acetate. The solution is washed by water, then by saturated NaHCO$_3$ $_{aq}$ and brine. The organic phase is dried over MgSO$_4$, and filtered and then evaporated and dried under reduced pressure to give a light brown solid. This residue is purified by flash chromatography (DCM/cyclohexane 9/1 to pure DCM and then DCM/MeOH 1000/1) to give the expected product as a yellowish powder (444 mg, 97%). [M+H]$^+$ m/z=295.2

Step 3'

[2-(3-methoxy-N-methyl-anilino)-2-oxo-ethyl]ammonium; 2,2,2-trifluoroacetate Tert-butyl N-[2-(3-methoxy-N-methyl-anilino)-2-oxo-ethyl]carbamate (444.4 mg, 1.510 mmol) is dissolved in 4 mL of DCM. TFA (19.97 mmol, 1.529 mL) is added and the reaction mixture is stirred at room temperature for 30 minutes. Solvent is removed to give a viscous reddish oil. 699 mg of residue are obtained corresponding to the expected product and to a rest of 3-methoxy-N-methyl-aniline. Residue is used in the next step without further purification.

MS: [M+H]$^+$ m/z=195.1

Step 4

N-(3-methoxy-phenyl)-2-[3-(4-fluoro-phenyl)-isothioureido]-N-methyl-acetamide In a 100 mL flask are added 1-fluoro-4-isothiocyanato-benzene (1.287 mmol, 446 mg) and TEA (1.544 mmol, 0.208 mL) in 2 mL of Ethanol. To this is added dropwise at room temperature a solution of [2-(3-methoxy-N-methyl-anilino)-2-oxo-ethyl]ammonium, 2,2,2-trifluoroacetate (1.287 mmol, 446 mg) and TEA (4.254 mmol, 0.574 mL) in 20 mL of ethanol. Reaction mixture is evaporated to drynessto give an oil. This oil is purified by flash chromatography (pure DCM to DCM/methanol 98/2), to give 361 mg of a white solid, corresponding to the expected product (69%).

MS: [M+H]$^+$ m/z=386.0

$^1$H-NMR (DMSO-d6): δ (ppm) 3.19 (s, 3H); 3.78 (s, 3H); 4.03 (brs, 2H); 6.92-7.04 (m, 3H); 7.09-7.21 (m, 2H); 7.30-7.50 (m, 3H); 7.68-7.79 (m, 1H).

Step 5

2-[2-(2,6-Difluoro-benzyl)-3-(4-fluoro-phenyl)-isothioureido]-N-(3-methoxy-phenyl)-N-methyl-acetamide In a 5 mL flask are added N-(3-methoxy-phenyl)-2-[3-(4-fluoro-phenyl)-isothioureido]-N-methyl-acetamide (100 mg, 288 μmol), Potassium Carbonate (40 mg, 288 μmol), sodium Iodide (22 mg, 144 μmol), and 1.5 mL of acetonitrile. The suspension is stirred at room temperature for 10 min, and 2-(bromomethyl)-1,3-difluoro-benzene (60 mg, 288 μmol) is then added. The suspension is stirred at room temperature for 6 hours. The medium is then evaporated, residue is dissolved in EtOAc, washed with water and brine, organic phase is dried over Na$_2$SO$_4$ and evaporated to dryness to give the titled product as an orange solid (136 mg, 94%).

MS: [M+H]$^+$ m/z=474.1

$^1$H-NMR (CDCl$_3$): δ (ppm) 3.32 (s, 3H); 3.81 (s, 3H); 3.90 (brs, 2H); 4.13 (brs, 2H); 6.68-6.96 (m, 9H); 7.16-7.26 (m, 1H); 7.34 (t, 1H, J=16.2 Hz).

Step 6

[2-(2,6-Difluoro-benzylsulfanyl)-3-(4-fluoro-phenyl)-3H-imidazol-4-yl]-(3-methoxy-phenyl)-methyl-amine 2-[2-(2,6-Difluoro-benzyl)-3-(4-fluoro-phenyl)-isothioureido]-N-(3-methoxy-phenyl)-N-methyl-acetamide (136 mg, 0.27 mmol) is dissolved in 2.7 mL of ethyl acetate. Diisopropylethylamine (283 μL, 1.62 mmol), and T3P in EtOAc (477 μL, 0.83 mmol) are then added. The mixture is heated with microwave at 150° C. for 10 min. Diisopropylethylamine (283 μL, 1.62 mmol), and T3P in EtOAc (477 μL, 0.83 mmol) are added again, and reaction mixture is heated again under microwave irradiation at 150° C. for 10 min. Diisopropylethylamine (142 μL, 0.81 mmol), and T3P in EtOAc (240 μL, 0.41 mmol) are added again, and reaction mixture is heated again under microwave irradiation at 150° C. for 10 min. Diisopropylethylamine (142 μL, 0.81 mmol), and T3P in EtOAc (240 μL, 0.41 mmol) are added again, and reaction mixture is heated again under microwave irradiation at 150° C. for 10 min. Reaction mixture is then diluted with EtOAc, washed by water, by saturated NaHCO$_3$ $_{aq}$, and by brine. Organic phase is then dried over Na$_2$SO$_4$ and evaporated. Residue is then purified by flash chromatography (cHex to cHex/EtOAc 85/15), to give the titled compound as an orange residue (12.1 mg, 10%).

MS [M+H]$^+$ m/z=456.1

$^1$H-NMR (CDCl$_3$): δ (ppm) 2.91 (s, 3H); 3.77 (s, 3H); 4.19 (s, 2H); 6.22 (t, 1H, J=2.3 Hz); 6.25 (dd, 1H, J=8.2 Hz, J=2.3 Hz); 6.37 (dd, 1H, J=8.2 Hz, J=2.3 Hz); 6.81-6.86 (m, 2H); 6.94-6.99 (m, 4H); 7.05 (s, 1H); 7.10 (t, 1H, J=8.1 Hz); 7.15-7.25 (m, 1H).

$^{13}$C-NMR (CDCl$_3$): δ (ppm) 25.8; 39.4; 55.2; 99.9; 103.5; 106.3; 111.3 (m); 113.5 (t, J=19.3 Hz); 116.0 (d, J=22.9 Hz); 125.3; 129.1 (d, J=8.8 Hz); 129.2 (t, J=10.3 Hz); 129.8; 130.7 (d, J=3.1 Hz); 138.5; 138.7; 149.9; 160.6; 161.2 (dd, J=250.2 Hz, J=7.6 Hz); 162.3 (d, J=249.3 Hz).

EXAMPLE 17

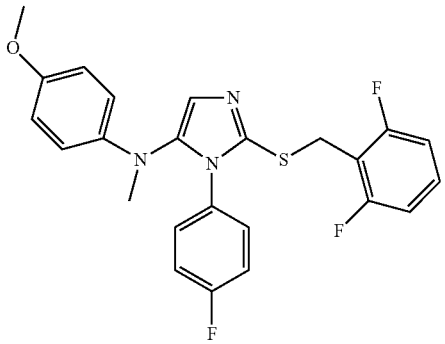 [SMILES: COc1ccc(N(C)c2cnc(SCc3c(F)cccc3F)n2-c2ccc(F)cc2)cc1]

Step 2' tert-butyl N-[2-(4-methoxy-N-methyl-anilino)-2-oxo-ethyl]carbamate

In a 25 mL flask is added commercial 4-methoxy-N-methyl-aniline (274 mg, 2 mmol) in 4 mL of EtOAc. Then 2-(tert-butoxycarbonylamino)acetic acid (420 mg, 2.4 mmol), T3P (1.768 ml, 3 mmol) and DIEA (1.048 mL, 6 mmol) are added. The mixture is stirred for 30 min at room temperature. Then the reaction mixture is diluted with ethyl acetate, washed with water, saturated NaHCO$_3$ $_{aq}$ and brine. The organic phase is dried over MgSO$_4$, filtered and then evaporated, to give the expected product as a bronze solid (463 mg, 79%).

MS: [M+H]$^+$ m/z=295.1

Step 3'

[2-(4-methoxy-N-methyl-anilino)-2-oxo-ethyl]ammonium; 2,2,2-trifluoroacetate

Tert-butyl N-[2-(4-methoxy-N-methyl-anilino)-2-oxo-ethyl]carbamate (463.70 mg, 1.575 mmol) is dissolved in 4 mL of DCM. TFA (20.84 mmol, 1.595 mL) is added and the reaction mixture is stirred at room temperature for 30 minutes. Solvent is removed to give a viscous reddish oil. 510 mg of residue is obtained corresponding to the expected product and to a rest of 4-methoxy-N-methyl-aniline. Residue is used in the next step without further purification.

MS: [M+H]$^+$ m/z=195.0

$^1$H-NMR (CDCl$_3$): δ (ppm) 3.20 (s, 3H); 3.57 (s, 2H); 3.83 (s, 3H); 6.95 (d, 2H, J=8.9 Hz); 7.12 (d, 2H, J=9.0 Hz); 7.80 (s, 3H);

Step 4

N-(4-methoxy-phenyl)-2-[3-(4-fluoro-phenyl)-isothioureido]-N-methyl-acetamide

In a 100 mL flask are added 1-fluoro-4-isothiocyanato-benzene (1.575 mmol, 241 mg) and TEA (1.890 mmol, 0.255 mL) in 5 mL of Ethanol. To this is added dropwise at room temperature a solution of [2-(4-methoxy-N-methyl-anilino)-2-oxo-ethyl]ammonium, 2,2,2-trifluoroacetate (1.575 mmol, 485 mg) and TEA (1.575 mmol, 0.213 mL) in 20 mL of Ethanol. Reaction mixture is evaporated to dryness to give 865 mg of pale green powder, corresponding to the expected product. Residue is used in the next step without further purification.

[M+H]$^+$ m/z=348.0

Step 5

2-[2-(2,6-Difluoro-benzyl)-3-(4-fluoro-phenyl)-isothioureido]-N-(4-methoxy-phenyl)-N-methyl-acetamide In a 100 mL flask are added N-(4-methoxy-phenyl)-2-[3-(4-fluoro-phenyl)-isothioureido]-N-methyl-acetamide (547 mg, 1.575 mmol), potassium carbonate (342 mg, 2.481 mmol), sodium iodide (185 mg, 1.240 mmol) and 12.4 mL of acetonitrile. The suspension is stirred at room temperature for 10 min, and 2-(bromomethyl)-1,3-difluoro-benzene (513 mg, 2.481 mmol) is then added. The suspension is stirred at room temperature for 16 hours. The medium is then evaporated, residue is dissolved in EtOAc, washed with water and brine, the organic phase is dried over MgSO$_4$ and evaporated to give a yellow oil, corresponding to the expected product (727 mg, 97%).

[M+H]$^+$ m/z=475.1

Step 6

[2-(2,6-Difluoro-benzylsulfanyl)-3-(4-fluoro-phenyl)-3H-imidazol-4-yl]-(4-methoxy-phenyl)-methyl-amine The titled product is obtained as an orange powder (120 mg, 17%), following Procedure C, using 2-[2-(2,6-Difluoro-benzyl)-3-(4-fluoro-phenyl)-isothioureido]-N-(4-methoxy-phenyl)-N-methyl-acetamide (1.535 mmol, 726 mg).

[M+H]$^+$ m/z=456.1

$^1$H-NMR (CDCl$_3$): δ (ppm) 2.92 (s, 3H); 3.76 (s, 3H); 4.18 (brs, 2H); 6.57-6.60 (m, 2H); 6.70-6.77 (m, 2H); 6.80-6.86 (m, 2H); 6.92-6.95 (m, 4H); 7.00 (s, 1H); 7.15-7.23 (m, 1H)

$^{13}$C-NMR (CDCl$_3$): δ (ppm) 25.9; 40.2; 55.7; 111.3 (m); 113.6; 114.4; 115.4; 115.9 (d, J=23.0 Hz); 124.1; 129.0-129.3 (m); 130.9 (d, J=3.4 Hz); 138.1; 140.0; 142.7; 153.1; 161.3 (dd, J=250.0 Hz, J=7.4 Hz); 162.3 (d, J=249.2 Hz).

EXAMPLE 18

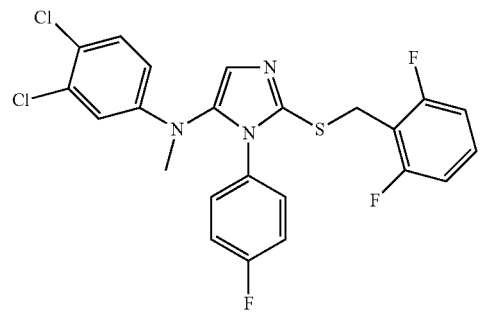 [SMILES: CN(c1ccc(Cl)c(Cl)c1)c1cnc(SCc2c(F)cccc2F)n1-c1ccc(F)cc1]

Step 1

3,4-dichloro-N-methyl-aniline

In a 25 mL flask are added 3,4-dichloroaniline (324 mg, 2.0 mmol) and sodium methoxide (540 mg, 10 mmol) in 3.5 mL of anhydrous methanol. Then, paraformaldehyde (120 mg, 4 mmol) is diluted in 1.5 mL of anhydrous methanol and the solution is added to the mixture. Molecular sieves (4 Angstroms) is then added and the mixture is stirred overnight at room temperature. The mixture is then heated under reflux for 1 hour with sodium borohydride (151 mg, 4 mmol). Reaction mixture is then filtered on Celite, evaporated, residue is dissolved in EtOAc and water, and the two phases are separated. Aqueous phase is then basified by addition of saturated $NaHCO_3$ $_{aq}$, and extracted by EtOAc. Organic phases are washed by saturated $NaHCO_3$ $_{aq}$. and by brine, dried over $MgSO_4$, evaporated and dried under vacuum to give a yellow oil corresponding to the titled product (227 mg, 64%).

MS: $[M+H]^+$ m/z=179.9

$^1$H-NMR (CDCl$_3$): δ (ppm) 2.83 (s, 3H); 6.48 (dd, 1H, J=8.7 Hz, J=2.8 Hz); 6.70 (d, J=2.8 Hz, 1H); 7.21 (d, 1H, J=8.8 Hz).

Step 2' tert-butyl N-[2-(3,4-dichloro-N-methyl-anilino)-2-oxo-ethyl]carbamate

In a 10 mL flask are added 3,4-dichloro-N-methyl-aniline (226 mg, 1.287 mmol) in 2.6 mL of EtOAc. Then 2-(tert-butoxycarbonylamino)acetic acid (608 mg, 3.474 mmol), T3P (2.2747 mL, 3.859 mmol) and DIEA (1.012 mL, 5.791 mmol) are added. The mixture is stirred at 40° C. for 2 days. Then the reaction mixture is diluted with ethyl acetate, washed with water, saturated $NaHCO_3$ $_{aq}$ and brine. The organic phase is dried over $MgSO_4$, and evaporated to dryness to give a yellowish oil. For the next step, yield is considered to be 100%.

MS: $[M+H-C(CH_3)_3]^+$ m/z=277.0

$^1$H-NMR (CDCl$_3$): δ (ppm) 1.4 (m, 9H); 3.25 (s, 3H); 3.65 (s, 2H); 3.35 (s, 1H); 7.1 (dd, 1H, J=2.4 Hz, J=8.4 Hz); 3.37 (d, 2H, J=2.3 Hz); 7.72 (d, 1H, J=8.5 Hz)

Step 3'

[2-(3,4-dichloro-N-methyl-anilino)-2-oxo-ethyl]ammonium; 2,2,2-trifluoroacetate tert-butyl N-[2-(4-methoxy-N-methyl-anilino)-2-oxo-ethyl]carbamate (428 mg, 1.287 mmol) is dissolved in 4 mL of DCM. TFA (1.303 mL, 17.03 mmol) is added and the reaction mixture is stirred at room temperature for 30 minutes. Solvent is removed to give an oil. Residue is used in the next step without further purification.

MS: $[M+H]^+$ m/z=235.11

Step 4

N-(3,4-dichloro-phenyl)-2-[3-(4-fluoro-phenyl)-isothioureido]-N-methyl-acetamide In a 100 mL flask are added 1-fluoro-4-isothiocyanato-benzene (446 mg, 1.287 mmol) and TEA (0.208 mL, 1.544 mmol) in 2 mL of Ethanol. To this is added dropwise at room temperature a solution of [2-(3,4-dichloro-N-methyl-anilino)-2-oxo-ethyl]ammonium, 2,2,2-trifluoroacetate (446 mg 1.287 mmol) and TEA (0.574 mL, 4.25 mmol) in 20 mL of ethanol. Reaction mixture is then evaporated to dryness. The residue is purified by flash chromatography (DCM to DCM/methanol 98/2), to give 550 mg of a white solid corresponding to the titled product (quantitative yield).

Step 5

2-[2-(2,6-Difluoro-benzyl)-3-(4-fluoro-phenyl)-isothioureido]-N-(3,4-dichloro-phenyl)-N-methyl-acetamide In a 100 mL flask are added N-(3,4-dichloro-N-methyl-anilino)-2-[3-(4-fluoro-phenyl)-isothioureido]-N-methyl-acetamide (280 mg, 0.725 mmol), potassium carbonate (100 mg, 0.725 mmol), sodium iodide (54.33 mg, 0.362 mmol) and 3.6 mL of acetonitrile. The suspension is stirred at room temperature for 10 min, and 2-(bromomethyl)-1,3-difluoro-benzene (150 mg, 0.725 mmol) is then added. The suspension is stirred at room temperature for 16 hours. The medium is then evaporated, residue is dissolved in EtOAc, washed with water and brine, the organic phase is dried over $MgSO_4$ and evaporated to give 334 mg of a yellowish oil, corresponding to the titled product (90%).

MS: $[M+H]^+$ m/z=512.1

$^1$H-NMR (CDCl$_3$): δ (ppm) 3.31 (s, 3H); 3.92 (s, 2H); 4.12 (s, 2H); 6.75-6.98 (m, 6H); 7.13 (m, 1H); 7.23 (m, 1H); 7.38 (m, 1H); 7.53 (d, 1H, J=8.49 Hz).

Step 6

[2-(2,6-Difluoro-benzylsulfanyl)-3-(4-fluoro-phenyl)-3H-imidazol-4-yl]-(3,4-dichloro-phenyl)-methyl-amine The titled product is obtained as an orange powder (143 mg, 44%), following Procedure C, using 2-[2-(2,6-Difluoro-benzyl)-3-(4-fluoro-phenyl)-isothioureido]-N-(3,4-dichloro-phenyl)-N-methyl-acetamide (334 mg, 0.65 mmol).

MS: $[M+H]^+$ m/z=496.0

$^1$H-NMR (CDCl$_3$): δ (ppm) 2.92 (s, 3H); 4.19 (s, 2H); 6.45 (dd, J=3.05 Hz, J=8.91 Hz, 1H); 6.72 (d, J=2.96 Hz, 1H); 6.87 (t, J=7.71 Hz, 1H); 6.82-6.95 (m, 6H); 7.05 (s, 1H); 7.2 (d, J=2.57 Hz, 1H); 7.22 (d, J=2.57 Hz, 1H)

$^{13}$C-NMR (CDCl$_3$): δ (ppm) 25.8; 39.6; 111.4 (m); 112.5; 113.5 (t, J=19.4 Hz); 114.5; 116.3 (d, J=23.1 Hz); 121.7; 125.6; 129.0 (d, J=8.8 Hz); 129.3 (t, J=10.3 Hz); 130.4; 132.9; 137.4; 139.5; 148.0; 161.2 (dd, J=250.0 Hz, J=7.3 Hz); 162.5 (d, J=249.9 Hz).

EXAMPLE 19

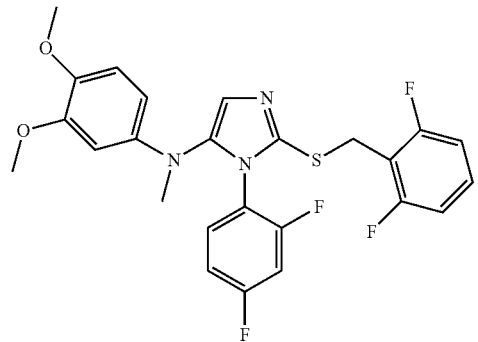 [SMILES: COc1ccc(N(C)c2cnc(SCc3c(F)cccc3F)n2-c2ccc(F)cc2F)cc1OC]

Step 2' tert-butyl N-[2-(3,4-dimethoxy-N-methyl-anilino)-2-oxo-ethyl]carbamate

In a 250 mL flask are added 3,4-dimethoxy-N-methyl-aniline (903 mg, 5.405 mmol) in 4 mL of EtOAc. Then 2-(tert-butoxycarbonylamino)acetic acid (1136 mg, 6.486 mmol), T3P (4.777 mL, 5159 mmol) and DIEA (2.832 mL, 16.21 mmol) are added. The mixture is stirred for 30 min at room temperature. Then reaction mixture is diluted with ethyl acetate, washed with water, saturated NaHCO$_3$ $_{aq}$ and brine. The organic phase is dried over MgSO$_4$, and evaporated to dryness, to give 1.77 g of reddish powder corresponding to the expected product (100%).

MS: [M+H]$^+$ m/z=325.0

$^1$H-NMR (CDCl$_3$): δ (ppm) 1.42 (s, 9H); 3.27 (s, 3H); 3.68 (s, 2H); 3.89 (m, 6H); 6.68 (d, 1H, J=2.4 Hz); 6.76 (dd, 1H, J=2.4 Hz, J=8.4 Hz); 6.86 (d, 1H, J=8.5 Hz)

Step 3'

[2-(3,4-dimethoxy-N-methyl-anilino)-2-oxo-ethyl]ammonium; 2,2,2-trifluoroacetate

In a 50 mL flask tert-butyl N-[2-(3,4-dimethoxy-N-methyl-anilino)-2-oxo-ethyl]carbamate (1770.4 mg, 5.458 mmol) is dissolved in 13.6 mL of DCM. TFA (5.526 mL, 72.21 mmol) is added and the reaction mixture is stirred at room temperature for 15 minutes. Solvent is evaporated to dryness to give a purple oil, corresponding to the expected product. Residue is used without further purification in the next step.

MS: [M+H]$^+$ m/z=225.1

Step 4

N-(3,4-dimethoxy-phenyl)-2-[3-(2,4-difluoro-phenyl)-isothioureido]-N-methyl-acetamide

In a 100 mL flask are added 2,4-difluoro-1-isothiocyanato-benzene (290 mg, 1.698 mmol) and TEA (0.275 ml, 2.037 mmol) in 5 mL of Ethanol. To this is added dropwise at room temperature a solution of [2-(3,4-dimethoxy-N-methyl-anilino)-2-oxo-ethyl]ammonium, 2,2,2-trifluoroacetate (574 mg, 1.698 mmol) and TEA (0.229 mL, 1.698 mmol) in 20 mL of ethanol. Reaction mixture is then evaporated to dryness. Residue is then purified by flash chromatography (DCM/cHex 1/1 to DCM/methanol 98/2) to give 335 mg of a yellowish powder corresponding to the expected product (50%).

MS: [M+H]$^+$ m/z=396.1

$^1$H-NMR (DMSO-d6): δ (ppm) 3.16 (s, 3H); 3.76 (s, 3H); 3.78 (s, 3H); 4.00 (s, 2H); 6.90-7.08 (m, 4H); 7.29 (m, 1H); 7.62 (m, 1H); 7.98 (brs, 1H); 9.59 (brs, 1H).

Step 5

2-[2-(2,6-Difluoro-benzyl)-3-(2,4-difluoro-phenyl)-isothioureido]-N-(3,4-dimethoxy-phenyl)-N-methyl-acetamide

In a 100 mL flask are added N-(3,4-dimethoxy-phenyl)-2-[3-(2,4-difluoro-phenyl)-isothioureido]-N-methyl-acetamide (335 mg, 0.85 mmol), potassium carbonate (117 mg, 0.847 mmol), sodium iodide (63 mg, 0.424 mmol) and 4.20 mL of acetonitrile. The suspension is stirred at room temperature for 10 min, and 2-(bromomethyl)-1,3-difluorobenzene (175 mg, 0.847 mmol) is then added. The suspension is stirred at room temperature for 16 hours. The medium is then evaporated, residue is dissolved in EtOAc, washed with water and brine, the organic phase is dried over MgSO4 and evaporated to give 413 mg of a yellowish oil corresponding to the titled product (93%).

MS: [M+H]$^+$ m/z=522.2

$^1$H-NMR (CDCl$_3$): δ (ppm) 3.31 (s, 3H); 3.83-3.99 (m, 8H); 4.18 (s, 2H); 6.65-6.93 (m, 9H); 7.17-7.25 (m, 1H).

Step 6

[2-(2,6-Difluoro-benzylsulfanyl)-3-(2,4-difluoro-phenyl)-3H-imidazol-4-yl]-(3,4-dimethoxy-phenyl)-methyl-amine

The titled product is obtained as a reddish solid (226 mg, 56%), following Procedure C, using 2-[2-(2,6-Difluoro-benzyl)-3-(2,4-difluoro-phenyl)-isothioureido]-N-(3,4-dimethoxy-phenyl)-N-methyl-acetamide (413 mg, 0.79 mmol).

MS: [M+H]$^+$ m/z=504.1

$^1$H-NMR (CDCl$_3$): δ (ppm) 3.02 (s, 3H); 3.77 (s, 3H); 3.80 (s, 3H); 4.17 (m, 2H); 6.14 (dd, 1H, J=8.7 Hz, J=2.8 Hz); 6.25 (d, 1H, J=2.8 Hz); 6.64-6.76 (m, 2H); 6.77-6.87 (m, 4H); 7.05 (s, 1H); 7.20 (m, 1H).

$^{13}$C-NMR (CDCl$_3$): δ (ppm) 26.2; 40.7; 55.8; 56.4; 100.6; 104.9 (dd, J=26.4 Hz, J=23.7 Hz); 106.2; 111.1-112.1 (m); 113.7 (t, J=19.4 Hz); 119.1 (dd, J=13.0 Hz, J=4.1 Hz); 123.8; 129.2 (t, J=10.3 Hz); 130.5 (d, J=10.2 Hz); 138.7; 140.4; 142.7; 143.0; 149.4; 157.8 (dd, J=255.1 Hz, J=12.9 Hz); 161.2 (dd, J=250.2 Hz, J=7.5 Hz); 162.9 (dd, J=252.4 Hz, J=11.3 Hz).

EXAMPLE 20

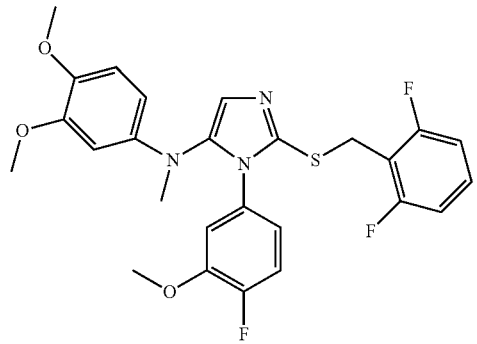 [SMILES: COc1cc(-n2c(N(C)c3ccc(OC)c(OC)c3)cnc2SCc2c(F)cccc2F)ccc1F]

Step 4

N-(3,4-dimethoxy-phenyl)-2-[3-(4-fluoro-3-methoxy-phenyl)-isothioureido]-N-methyl-acetamide

In a 25 mL flask, TCDI (133 mg, 0.749 mmol) is dissolved in 3 mL of dioxane. [2-(3,4-dimethoxy-N-methyl-anilino)-2-oxo-ethyl]ammonium, 2,2,2-trifluoroacetate (230 mg, 0.681 mmol) in 3.50 mL of dioxane is then added dropwise. The solution is then stirred at room temperature for 1.5 hour. 4-fluoro-3-methoxy-aniline (106 mg, 0.750 mmol) and TEA (285 µL, 2.04 mmol) are added to the solution. Reaction mixture is stirred at 60° C. overnight. Solvent is then removed. Residue is dissolved in EtOAc, and washed with water and aqueous 0.1N HCl solution, dried over MgSO$_4$. After evaporation, residue is purified by flash chromatography (pure cHex to cHex/EtOAc 8/2) to give 136 mg of an orange solid corresponding to the titled product (49%).

MS: [M+H]$^+$ m/z=408.1

$^1$H-NMR (DMSO d-6): δ (ppm) 3.16 (s, 3H); 3.74-3.82 (m, 9H); 4.00 (d, 2H, J=4.2 Hz); 6.84-6.96 (m, 2H); 6.98-7.06 (m, 2H); 7.15 (dd, 1H, J=11.3 Hz, J=8.7 Hz); 7.37 (dd, J=7.9 Hz, J=2.2 Hz); 7.77 (brs, 1H); 9.91 (s, 1H).

Step 5

2-[2-(2,6-Difluoro-benzyl)-3-(4-fluoro-3-methoxy-phenyl)-isothioureido]-N-(3,4-dimethoxy-phenyl)-N-methyl-acetamide In a 5 mL flask are added N-(3,4-dimethoxy-phenyl)-2-[3-(4-fluoro-3-methoxy-phenyl)-isothioureido]-N-methyl-acetamide (124 mg, 304 μmol), Potassium Carbonate (42 mg, 304 μmol), sodium Iodide (23 mg, 152 μmol), and 1.5 mL of acetonitrile. The suspension is stirred at room temperature for 10 min, and 2-(bromomethyl)-1,3-difluoro-benzene (63 mg, 304 μmol) is then added. The suspension is stirred at room temperature for 18 hours. The medium is then evaporated, residue is dissolved in EtOAc, washed with water and brine, organic phase is dried over Na$_2$SO$_4$ and evaporated to dryness to give the titled product as a yellowish oil (156 mg, 91%).

MS: [M+H]$^+$ m/z=534.2

$^1$H-NMR (CDCl$_3$): δ (ppm) 3.28 (s, 3H); 3.78-3.84 (m, 11H); 4.11 (brs, 2H); 5.82 (s, 1H); 6.29 (brs, 1H); 6.44 (d, 1H, J=6.3 Hz); 6.61-6.89 (m 6H); 7.13-7.26 (m, 1H).

Step 6

[2-(2,6-Difluoro-benzylsulfanyl)-3-(4-fluoro-3-methoxy-phenyl)-3H-imidazol-4-yl]-(3,4-dimethoxy-phenyl)-methyl-amine The titled product is obtained as an orange powder (143 mg, 63%), following Procedure C, using 2-[2-(2,6-Difluoro-benzyl)-3-(4-fluoro-3-methoxy-phenyl)-isothioureido]-N-(3,4-dimethoxy-phenyl)-N-methyl-acetamide (156 mg, 0.28 mmol).

MS: [M+H]$^+$ m/z=516.2

$^1$H-NMR (CDCl$_3$): δ (ppm) 2.90 (s, 3H); 3.54 (s, 3H); 3.82 (s, 6H); 4.20 (s, 2H); 6.18 (dd, 1H, J=8.7 Hz, J=2.8 Hz); 6.33 (d, 1H, J=2.8 Hz); 6.54 (dd, 1H, J=7.5 Hz, J=2.4 Hz); 6.59-6.64 (m, 1H); 6.75 (d, 1H, J=8.7 Hz); 6.78-6.86 (m, 2H); 6.98 (dd, 1H, J=10.8 Hz, J=8.6 Hz); 7.06 (s, 1H); 7.14-7.24 (m, 1H).

$^{13}$C-NMR (CDCl$_3$): δ (ppm) 25.7; 39.9; 55.9; 56.0; 56.6; 99.7; 105.2; 111.1-111.4 (m); 112.6; 112.7 (d, J=2.4 Hz); 113.6 (t, J=19.4 Hz); 115.9 (d, J=19.6 Hz); 119.7 (d, J=7.3 Hz); 124.9; 129.2 (t, J=10.2 Hz); 130.9 (d, J=3.6 Hz); 138.6; 139.0; 142.6; 143.5; 147.5 (d, J=11.6 Hz); 149.8; 152.0 (d, J=248.9 Hz); 161.2 (dd, J=249.9 Hz, J=7.7 Hz).

EXAMPLE 21

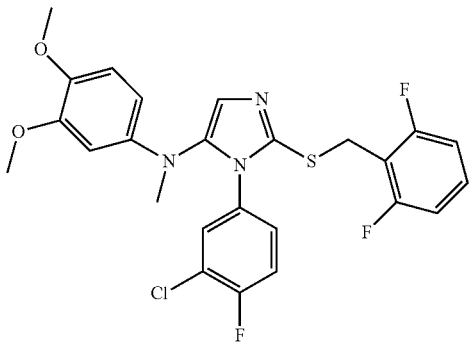 [SMILES: COc1ccc(N(C)c2cnc(SCc3c(F)cccc3F)n2-c2ccc(F)c(Cl)c2)cc1OC]

Step 4

N-(3,4-dimethoxy-phenyl)-2-[3-(3-chloro-4-fluoro-phenyl)-isothioureido]-N-methyl-acetamide In a 100 mL flask are added 1-fluoro-4-isothiocyanato-benzene (318 mg, 1.697 mmol) and TEA (0.275 mL, 2.036 mmol) in 5 mL of Ethanol. To this is added dropwise at room temperature a solution of [2-(3,4-dimethoxy-N-methyl-anilino)-2-oxo-ethyl]ammonium, 2,2,2-trifluoroacetate (574 mg, 1.697 mmol) and TEA (0.229 mL, 1.697 mmol) in 20 mL of ethanol. Reaction mixture is then evaporated to dryness and purified by flash chromatography (pure DCM to DCM/MeOH 98/2) to give 367 mg of pale green powder, corresponding to the expected product (53%).

MS: [M+H]$^+$ m/z=412.0

$^1$H-NMR (DMSO-d6): δ (ppm) 3.17 (s, 3H); 3.77 (s, 3H); 3.79 (s, 3H); 4.00 (d, 2H, J=4.2 Hz); 6.93 (dd, 1H, J=8.4 Hz, 2.3 Hz); 7.34-7.36 (m, 2H); 7.84-7.95 (m, 2H); 10.05 (s, 1H).

Step 5

2-[2-(2,6-Difluoro-benzyl)-3-(3-chloro-4-fluoro-phenyl)-isothioureido]-N-(3,4-dimethoxy-phenyl)-N-methyl-acetamide In a 25 mL flask are added N-(3,4-dimethoxy-phenyl)-2-[3-(3-chloro-4-fluoro-phenyl)-isothioureido]-N-methyl-acetamide (184 mg, 0.45 mmol), potassium carbonate (61 mg, 0.446 mmol), sodium iodide (33 mg, 0.223 mmol) and 2.23 mL of acetonitrile. The suspension is stirred at room temperature for 10 min, and 2-(bromomethyl)-1,3-difluoro-benzene (92 mg, 0.446 mmol) is then added. The suspension is stirred at room temperature for 16 hours. The medium is then evaporated, residue is dissolved in EtOAc, washed with water and brine, the organic phase is dried over MgSO$_4$ and evaporated to give 238 mg of an orange oil, corresponding to the titled product (99%).

MS: [M+H]$^+$ m/z=538.1

$^1$H-NMR (CDCl$_3$): δ (ppm) 3.29 (s, 3H); 3.79-3.93 (m, 8H); 4.13 (s, 2H); 6.57-7.00 (m, 9H); 7.15-7.27 (m, 1H).

Step 6

[2-(2,6-Difluoro-benzylsulfanyl)-3-(3-chloro-4-fluoro-phenyl)-3H-imidazol-4-yl]-(3,4-dimethoxy-phenyl)-methyl-amine The titled product is obtained as an orange powder (126 mg, 55%), following Procedure C, using 2-[2-(2,6-Difluorobenzyl)-3-(3-chloro-4-fluoro-phenyl)-isothioureido]-N-(3,4-dimethoxy-phenyl)-N-methyl-acetamide (238 mg, 0.44 mmol).

MS: [M+H]+ m/z=520.1

1H-NMR (CDCl3): δ (ppm) 2.96 (s, 3H); 3.80 (s, 3H); 3.82 (s, 3H); 4.14 (s, 2H); 6.15 (dd, 1H, J=8.7 Hz, J=2.7 Hz); 6.71 (d, 1H, J=8.7 Hz); 6.77-6.89 (m, 3H); 6.91 (dd, 1H, J=6.4 Hz, J=2.5 Hz); 7.01 (t, 1H, J=8.5 Hz); 7.03 (s, 1H); 7.20 (m, 1H).

13C-NMR (CDCl3): δ (ppm) 26.3; 40.6; 56.0; 56.5; 100.6; 106.5; 111.3 (m); 112.3; 113.6 (t, J=19.4 Hz); 116.6 (d, J=22.4 Hz); 121.2 (d, J=19.1 Hz); 124.0; 127.5 (d, J=7.7 Hz); 129.3 (t, J=10.2 Hz); 129.7; 131.4 (d, J=3.9 Hz); 137.9; 139.9; 142.9; 143.2; 149.7; 157.8 (d, J=251.7 Hz); 161.1 (dd, J=249.7 Hz, J=7.6 Hz).

Synthesis of Intermediate 3

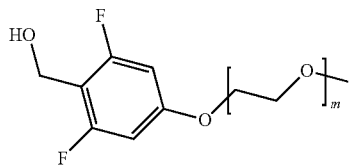

m = 10-22

[2,6-Difluoro-4-(methoxy-polyethyleneglycoxy)-phenyl]-methanol (Average MW=947 g/mol)

Polyethyeneglycol methyl ether tosylate (average molecular weight=900) (1.2 mmol, 1080 mg) is dissolved in acetonitrile (4 mL), 3,5-Difluoro-4-hydroxymethyl-phenol (1.32 mmol, 211 mg) and K2CO3 (1.44 mmol, 199 mg) are added. The reaction mixture is stirred overnight under reflux. The reaction mixture is then cooled down, and filtered. The filtrate is concentrated under vaccuum and purified by preparative HPLC, to give a white viscous residue corresponding to the titled product (697 mg, 61%).

MS: [M+H3O]+ m/z=808.2 (m=14)

1H-NMR (DMSO-d6): δ (ppm) 3.23 (s, 3H); 3.38-3.58 (m, 66H); 3.72 (m, 2H); 4.11 (m, 2H); 4.40 (s, 2H); 6.71 (m, 2H).

EXAMPLE 22

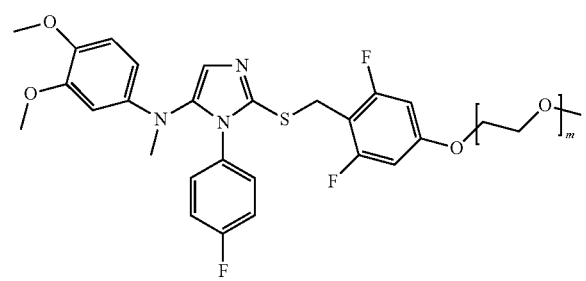

m = 10-22

Step 5

2-[2-[2,6-Difluoro-4-(methoxy-polyethyleneglycoxy)-benzyl]-3-(4-fluoro-phenyl)-isothioureido]-N-(3,4-dimethoxy-phenyl)-N-methyl-acetamide (Average MW=1209 g/mol)

[2,6-Difluoro-4-(methoxy-polyethyleneglycoxy)-phenyl]-methanol (intermediate 3) (697 mg, 0.74 mmol) and TEA (144 μL, 1.07 mmol) are dissolved in 2 mL dry DCM at 0° C. Mesylchloride (68.6 μL, 0.89 mmol) is then added dropwise, and the mixture is stirred at room temperature overnight. Reaction mixture is then evaporated to dryness. This residue is added to a 25 mL flask loaded with N-(3,4-Dimethoxy-phenyl)-2-[3-(4-fluoro-phenyl)-isothioureido]-N-methyl-acetamide (279 mg, 0.74 mmol), K2CO3 (153 mg, 1.11 mmol), and 4 mL of acetonitrile. The suspension is stirred at room temperature for 4 hours. Then K2CO3 (102 mg, 0.74 mmol) is added, and reaction is stirred at 50° C. for 16 hours. Reaction mixture is then evaporated to dryness and purified twice by flash chromatography (pure DCM to DCM/MeOH 98/2) to give 146 mg of a pale pink solid, corresponding to the expected product (17%).

MS [M+H+H3O]2+ m/z=606.2 (n=15)

Step 6

[2-[2,6-Difluoro-4-(2-methoxy-polyethyleneglycoxy)-benzylsulfanyl]-3-(4-fluoro-phenyl)-3H-imidazol-4-yl]-(3,4-dimethoxy-phenyl)-methyl-amine (Average MW=1204 g/mol)

The titled compound is obtained as a orange oil (20 mg, 13%) following Procedure B, using 2-[2-[2,6-Difluoro-4-(methoxy-polyethyleneglycoxy)-benzyl]-3-(4-fluoro-phenyl)-isothioureido]-N-(3,4-dimethoxy-phenyl)-N-methyl-acetamide (148 mg). Purification was performed by preparative HPLC.

MS [M+H+H3O]2+ m/z=619.2 (n=16)

1H-NMR (CD2Cl2): δ (ppm) 2.96 (s, 3H); 3.36 (s, 3H); 3.50-3.72 (m, 80H); 3.74-3.77 (m, 6h); 3.78-3.88 (m, 4H); 4.04-4.14 (m, 4H); 6.15 (dd, 1H, J=8.70 Hz, J=2.79); 6.27 (d, 1H, J=2.79 Hz); 6.41-6.50 (m, 2H); 6.72 (d, 1H, J=8.70 Hz); 6.96-7.07 (m, 5H).

13C-NMR (CD2Cl2): δ (ppm) 25.8; 40.1; 55.8; 56.4; 58.6; 68.3; 69.2; 70.3; 70.4; 70.5; 70.8; 71.9; 98.1-98.7 (m); 100.1; 105.5; 105.6 (t, J=20.5 Hz); 112.9; 115.7 (d, J=23.0 Hz); 124.0; 129.3 (d, J=8.8 Hz); 131.1 (d, J=3.3 Hz); 138.0; 139.8; 142.8; 143.3; 149.8; 159.7 (t, J=14.5 Hz); 161.6 (dd, J=247.1 Hz, J=11.3 Hz); 162.3 (d, J=248.3 Hz).

EXAMPLE 23

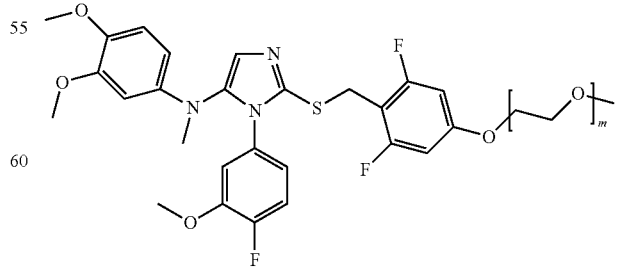

m = 15-22

Step 5

2-[2-[2,6-Difluoro-4-(methoxy-polyethyleneglycoxy)-benzyl]-3-(4-fluoro-3-methoxy-phenyl)-isothioureido]-N-(3,4-dimethoxy-phenyl)-N-methyl-acetamide (Average MW=1209 g/mol)

[2,6-Difluoro-4-(methoxy-polyethyleneglycoxy)-phenyl]-methanol (intermediate 3) (893 mg, 1.02 mmol) and TEA (198 µL, 1.47 mmol) are dissolved in 2 mL dry DCM at 0° C. Mesylchloride (96 µL, 1.22 mmol) is then added dropwise, and the mixture is stirred at room temperature overnight. At that time, TEA (136 µL, 1.02 mmol) and Mesylchloride (79 µL, 1.02 mmol) are added again. Reaction mixture is then evaporated to dryness. This residue is added to a 25 mL flask loaded with N-(3,4-dimethoxy-phenyl)-2-[3-(4-fluoro-3-methoxy-phenyl)-isothioureido]-N-methyl-acetamide (414 mg, 1.02 mmol), $K_2CO_3$ (211 mg, 1.52 mmol), NaI (76.1 mg, 0.51 mmol) and 4 mL of acetonitrile. The suspension is stirred at room temperature for 48 hours. Reaction mixture is then evaporated to dryness and purified by preparative HPLC to give 333 mg of a pale pink solid, corresponding to the expected product (26%).

MS $[M+H+H_3O]^{2+}$ m/z=643.5 (n=16)

$^1$H-NMR ($CD_2Cl_2$): δ (ppm) 3.29 (s, 3H); 3.35 (s, 3H); 3.50-3.72 (m, 80H); 3.80-3.90 (m, 13H); 4.03-4.17 (m, 4H); 6.32 (brs, 1H); 6.46-6.56 (m, 3H); 6.70-7.02 (5H).

Step 6

[2-[2,6-Difluoro-4-(2-methoxy-polyethyleneglycoxy)-benzylsulfanyl]-3-(4-fluoro-3-methoxy-phenyl)-3H-imidazol-4-yl]-(3,4-dimethoxy-phenyl)-methyl-amine (Average MW=1329 g/mol)

2-[2-[2,6-Difluoro-4-(methoxy-polyethyleneglycoxy)-benzyl]-3-(4-fluoro-3-methoxy-phenyl)-isothioureido]-N-(3,4-dimethoxy-phenyl)-N-methyl-acetamide (average MW=1209 g/mol) (266 mg, 0.21 mmol) was dissolved in 2.1 mL of dry EtOAc, and introduced in a 2-5 mL microwave tube. The solution was flushed with argon, then DIEA (233 µL, 1.26 mmol) and T3P in EtOAc (371 µL, 0.63 mmol) were added, and the mixture was heated under microwave irradiation at 150° C. for 10 min (absorption level set on high). Reaction being not complete, DIEA (155 µL, 0.84 mmol) and T3P in EtOAc (247 µL, 0.42 mmol) were added again, and reaction mixture was heated a 130° C. for 5 min under microwave irradiation. Reaction mixture was evaporated to dryness and purified by preparative HPLC, to give 47 mg of a pale orange oil, corresponding to the expected product (17%).

MS $[M+H+H_3O]^{2+}$ m/z=678.6 (n=18)

$^1$H-NMR ($CD_2Cl_2$): δ (ppm) 2.93 (s, 3H); 3.36 (s, 3H); 3.48-3.72 (m, 76H); 3.73-3.78 (m, 6H); 3.79-3.85 (m, 2H); 4.04-4.13 (m, 4H); 6.17 (dd, 1H, J=8.7 Hz, J=2.7 Hz); 6.31 (d, 1H, J=2.6 Hz); 6.40-6.50 (m, 2H); 6.57 (dd, 1H, J=7.6 Hz, J=2.3 Hz); 6.63-6.70 (m, 1H); 6.75 (d, 1H, J=8.7 Hz); 6.96-7.09 (m, 2H).

$^{13}$C-NMR ($CD_2Cl_2$): δ (ppm) 25.8; 39.9; 55.8; 55.9; 56.5; 58.6; 68.3; 69.2; 70.4; 70.5; 70.8; 71.9; 98.1-98.5 (m); 99.9; 105.5; 105.6 (t, J=20.2 Hz); 112.9 (d, J=2.5 Hz); 113.1; 115.7 (d, J=19.6 Hz); 119.8 (d, J=7.3 Hz); 124.7; 131.2 (d, J=3.6 Hz); 138.2; 139.3; 142.7; 143.6; 147.6 (d, J=11.6 Hz); 150.0; 151.9 (d, J=247.9 Hz); 159.7 (t, J=14.1 Hz); 161.7 (dd, J=252.8 Hz, J=5.6 Hz).

Synthesis of Intermediate 4

m = 34-51

[2,6-Difluoro-4-(methoxy-polyethyleneglycoxy)-phenyl]-methanol (Average MW=947 g/mol)

Polyethyeneglycol methyl ether tosylate (average molecular weight=2000) (1.2 mmol, 2400 mg) is dissolved in MeCN (4 mL), 3,5-Difluoro-4-hydroxymethyl-phenol (1.32 mmol, 211 mg) and $K_2CO_3$ (1.44 mmol, 199 mg) are added. The reaction mixture is stirred overnight under reflux. The reaction mixture is then cooled down, and filtered. The filtrate is concentrated under vaccuum. Then residue is partially solubilized in a DCM/MeOH 99/1 mixture, and $Et_2O$ is then added, leading to the formation of a precipitate (mainly corresponding to the tosylate), which is filtered. Filtrate is evaporated to dryness to give a white solid corresponding to the titled product. It is used without further purification in the next step, yield is considered to be 100%

$^1$H-NMR (DMSO-d6): δ (ppm) 3.23 (s, 3H); 3.36-3.76 (m, 278H); 4.06-4.14 (m, 2H); 4.40 (brs, 2H); 5.08 (brs, 1H); 6.56-6.76 (m, 2H).

EXAMPLE 24

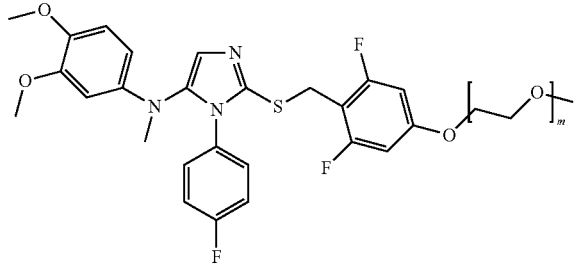

m = 36-47

Step 5

2-[2-[2,6-Difluoro-4-(methoxy-polyethyleneglycoxy)-benzyl]-3-(4-fluoro-phenyl)-isothioureido]-N-(3,4-dimethoxy-phenyl)-N-methyl-acetamide (Average MW=2413 g/mol)

[2,6-Difluoro-4-(methoxy-polyethyleneglycoxy)-phenyl]-methanol (intermediate 4) (2.91 g, 1.47 mmol) and TEA (246 µL, 1.83 mmol) are dissolved in 5 mL dry DCM at 0° C. Mesylchloride (114 µL, 1.46 mmol) is then added dropwise, and the mixture is stirred at room temperature overnight. Reaction mixture is then evaporated to dryness. This residue is added to a 50 mL flask loaded with N-(3,4-dimethoxy-phenyl)-2-[3-(4-fluoro-phenyl)-isothioureido]-N-methyl-acetamide (553 mg, 1.47 mmol), $K_2CO_3$ (304 mg, 2.20 mmol), and 4 mL of acetonitrile. The suspension is stirred at room temperature overnight. Reaction mixture is then evaporated to dryness and residue is then purified by FC (cHex/DCM 1/1 to DCM/MeOH 96/4) to give 693 mg of a yellow solid corresponding to the expected product (20%).

MS [M+H+3H$_3$O]$^{4+}$ m/z=609.4 (n=42)

Step 6

[2-[2,6-Difluoro-4-(2-methoxy-polyethyleneglycoxy)-benzylsulfanyl]-3-(4-fluorophenyl)-3H-imidazol-4-yl]-(3,4-dimethoxy-phenyl)-methyl-amine (Average MW=2347 g/mol)

2-[2-[2,6-Difluoro-4-(methoxy-polyethyleneglycoxy)-benzyl]-3-(4-fluoro-phenyl)-isothioureido]-N-(3,4-dimethoxy-phenyl)-N-methyl-acetamide (average MW=2413 g/mol) (554 mg, 0.23 mmol) in 2.3 mL of ethyl acetate. To this solution are added DIEA (240.8 µL, 1.38 mmol) and T3P (408 µL, 0.69 mmol). Reaction mixture is then heated at reflux for 24 hours. Reaction mixture is then evaporated to dryness and purified by preparative HPLC to give 110 mg of a yellowish solid corresponding to the expected product (20%).

MS [M+H+2H$_3$O]$^{3+}$ m/z=786.0 (n=41)

$^1$H-NMR (CD$_2$Cl$_2$): δ (ppm) 2.96 (s, 3H); 3.36-3.87 (m, 213H); 4.04-4.11 (m, 4H); 6.15 (dd, 1H, J=8.70 Hz, J=2.79); 6.27 (d, 1H, J=2.76 Hz); 6.41-6.50 (m, 2H); 6.72 (d, 1H, J=8.73 Hz); 6.96-7.07 (m, 5H).

$^{13}$C-NMR (CD$_2$Cl$_2$): δ (ppm) 25.8; 40.1; 55.8; 56.4; 58.6; 68.3; 69.2; 70.3; 70.4; 70.5; 70.8; 71.9; 98.1-98.7 (m); 100.1; 105.5; 105.6 (t, J=20.5 Hz); 112.9; 115.7 (d, J=23.0 Hz); 124.0; 129.3 (d, J=8.9 Hz); 131.1 (d, J=3.3 Hz); 138.0; 139.8; 142.8; 143.3; 149.8; 159.7 (t, J=14.5 Hz); 161.6 (dd, J=247.1 Hz, J=11.3 Hz); 162.3 (d, J=248.3 Hz).

Synthesis of Intermediate 5

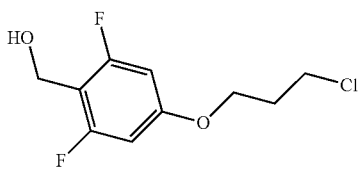 [SMILES: OCc1c(F)cc(OCCCCl)cc1F]

[4-(3-chloropropoxy)-2,6-difluoro-phenyl]methanol 1-bromo-3-chloro-propane (1.30 mL, 13.2 mmol), 3,5-Difluoro-4-hydroxymethyl-phenol (2.64 mmol, 423 mg) and potassium carbonate (365 mg, 2.64 mmol) are added in acetonitrile (9 mL) and the reaction mixture is stirred at reflux for 3 hours. The solvent is removed under reduced pressure. The crude was dissolved in EtOAc and washed with water. The aqueous phase was extracted by EtOAc, washed with brine, and dried over Na$_2$SO$_4$. The solvents were removed under reduced pressure, to give a colorless oil corresponding to the titled product (602 mg, 96%).

MS [M+H—H$_2$O]$^+$ m/z=218.9

$^1$H-NMR (CDCl$_3$): δ (ppm) 2.24 (quin, 2H, J=6.05 Hz); 3.73 (t, 2H, J=6.26 Hz); 4.10 (t, 2H, J=5.82 Hz); 4.71 (s, 2H); 6.41-6.52 (m, 2H).

Synthesis of Intermediate 6

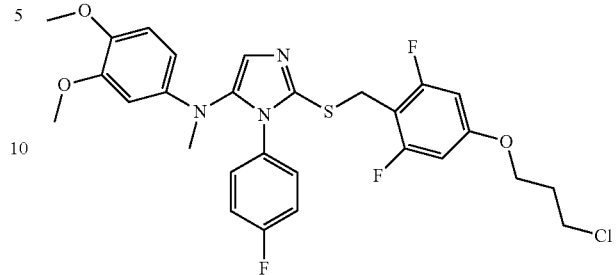

Step 5

2-[2-[2,6-Difluoro-4-(3-chloropropoxy)-benzyl]-3-(4-fluoro-phenyl)-isothioureido]-N-(3,4-dimethoxy-phenyl)-N-methyl-acetamide

[4-(3-chloropropoxy)-2,6-difluoro-phenyl]methanol (intermediate 5) (602 mg, 2.54 mmol) and TEA (428 µL, 3.17 mmol) are dissolved in 5 mL dry DCM at 0° C. Mesylchloride (197 µL, 2.54 mmol) is then added dropwise, and the mixture is stirred at room temperature overnight. Reaction mixture is then evaporated to dryness. Water is then added to quench the reaction. The organic phase is then washed with water and brine, and dried over Na$_2$SO$_4$, and then evaporated. The residue is added to a 50 mL flask loaded with N-(3,4-dimethoxy-phenyl)-2-[3-(4-fluoro-phenyl)-isothioureido]-N-methyl-acetamide (800 mg, 2.12 mmol), Potassium Carbonate (322 mg, 2.33 mmol), and 10 mL of acetonitrile. The suspension is stirred at room temperature overnight. Potassium carbonate (146 mg, 1.51 mmol) is then added, and mixture is stirred at room temperature overnight. The medium is then evaporated, residue is dissolved in EtOAc, washed with water and brine, organic phase is dried over Na$_2$SO$_4$ and evaporated. Residue is then purified by Flash Chromatography (pure cHex to cHex/EtOAc 7/3) to give a yellowish solid, corresponding to the titled product (915 mg, 73%).

MS [M+H]$^+$ m/z=595.9

$^1$H-NMR (CDCl$_3$): δ (ppm) 2.15 (quin, 2H, J=5.93 Hz); 3.27 (s, 3H); 3.66 (t, 2H, J=6.19 Hz); 3.76-3.93 (m, 8H); 3.95-4.14 (m, 4H); 6.32-6.46 (m, 2H); 6.60-6.94 (m, 7H).

Step 6

[2-(2,6-Difluoro-4-(3-chloropropoxy)-benzylsulfanyl)-3-(4-fluoro-phenyl)-3H-imidazol-4-yl]-(3,4-dimethoxy-phenyl)-methyl-amine The titled product is obtained as a brown solid (895 mg, 96%), following Procedure B (without Flash Chromatography purification), using 2-[2-[2,6-Difluoro-4-(3-chloropropoxy)-benzyl]-3-(4-fluoro-phenyl)-isothioureido]-N-(3,4-dimethoxy-phenyl)-N-methyl-acetamide (915 mg, 1.56 mmol).

MS [M+H]$^+$ m/z=577.9

$^1$H-NMR (CDCl$_3$): δ (ppm) 2.21 (quin, 2H, J=6.01 Hz); 2.91 (s, 3H); 3.72 (t, 2H, J=6.19 Hz); 3.77-3.86 (m, 6H); 4.00-4.14 (m, 4H); 6.16 (dd, 1H, J=8.69 Hz, J=2.78 Hz); 6.30 (d, 1H, J=2.73 Hz); 6.32-6.42 (m, 2H); 6.72 (d, 1H, J=8.73 Hz); 6.91-7.05 (m, 5H).

$^{13}$C-NMR (CDCl$_3$): δ (ppm) 25.8; 31.8; 40.1; 41.1; 55.9; 56.4; 64.8; 98.0-98.6 (m); 100.0; 105.5; 105.6 (t, J=20.2 Hz); 112.4; 115.9 (d, J=22.9 Hz); 124.3; 129.2 (d, J=8.7 Hz); 130.9 (d, J=3.1 Hz); 138.5; 139.5; 142.7; 143.2; 149.6; 159.5 (t, J=14.1 Hz); 161.7 (dd, J=248.1 Hz, J=11.0 Hz); 162.3 (d, J=249.2 Hz).

EXAMPLE 25

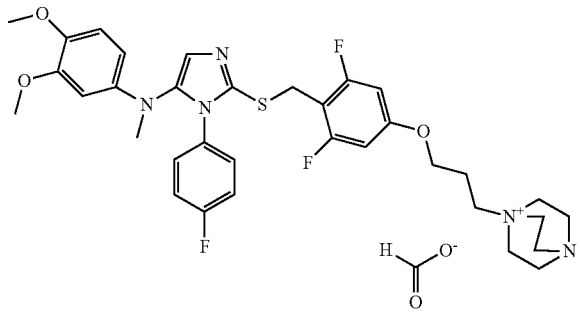

2-[[4-[3-(1-aza-4-azoniabicyclo[2.2.2]octan-4-yl)propoxy]-2,6-difluoro-phenyl]methylsulfanyl]-N-(3,4-dimethoxyphenyl)-3-(4-fluorophenyl)-N-methyl-imidazol-4-amine; formate Intermediate 6 (225 mg, 370 µmol) and DABCO (112 mg, 1.0 mmol) are dissolved in dry acetonitrile (3.7 mL). Reaction mixture is then heated under microwave irradiation at 100° C. for 30 min. It is then evaporated to dryness and purified by preparative HPLC (ammonium formate buffer, pH=9.2) to give 60 mg of a pale orange powder corresponding to the expected product (23%).

MS [M+H]$^+$ m/z=654.2

$^1$H-NMR (CDCl$_3$): δ (ppm) 2.31 (brs, 2H); 2.94 (s, 3H); 3.32 (brs, 6H); 3.48-3.82 (m, 14H); 3.94 (s, 2H); 4.06 (brs, 2H); 6.16 (dd, J=8.7 Hz, J=2.7 Hz, 1H); 6.27 (d, J=2.7 Hz, 1H); 6.35-6.47 (m, 2H); 6.71 (d, J=8.8 Hz, 1H); 6.93-7.11 (m, 5H); 8.60 (s, 1H).

$^{13}$C-NMR (CDCl$_3$): δ (ppm) 22.1; 25.7; 40.3; 45.3; 52.6; 55.9; 56.5; 61.8; 65.2; 98.2-98.8 (m); 100.1; 105.9; 106.0 (t, J=20.1 Hz); 112.5; 116.0 (d, J=22.9 Hz); 123.9; 129.3 (d, J=8.8 Hz); 130.9 (d, J=3.2 Hz); 137.8; 140.1; 142.8; 143.1; 149.6; 159.0 (t, J=14.1 Hz); 161.6 (dd, J=248.2 Hz, J=11.0 Hz); 162.3 (d, J=249.3 Hz).

EXAMPLE 26

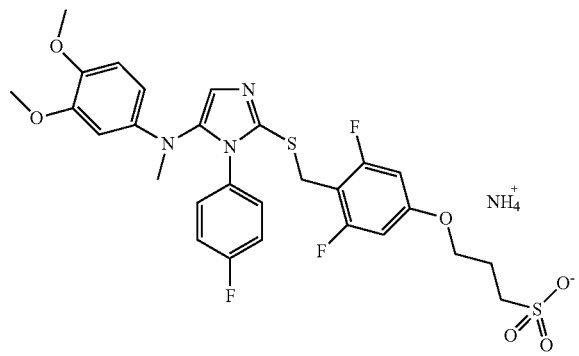

ammonium;3-[4-[[5-(3,4-dimethoxy-N-methyl-anilino)-1-(4-fluorophenyl)imidazol-2-yl]sulfanylmethyl]-3,5-difluoro-phenoxy]propane-1-sulfonate In a 2-5 mL microwave tube, Intermediate 6 (540 mg, 0.89 mmol) was dissolved in 6 mL of a mixture of Dioxane and water (1/1, V/V). Sodium sulfite (559 mg, 4.44 mmol) and sodium iodide (133 mg, 0.89 mmol) were then added. Reaction mixture was the successively heated under microwave irradiation according to the following settings:

[MWx: temperature, time, sensitivity]

MW1: 130° C., 30 min, Very high.

MW2: 130° C., 40 min, Very high.

Then Sodium sulfite (223 mg, 1.8 mmol) and sodium iodide (53 mg, 0.36 mmol) were added again, before MW3.

MW3: 130° C., 30 min, Very high.

Reaction mixture was evaporated to dryness and purified by preparative HPLC (ammonium formate buffer pH=3.8) to give a yellowish powder corresponding to the pure expected product (207 mg, 36%).

MS [M+H]$^-$ m/z=622.1

$^1$H-NMR (MeOD-d4): δ (ppm) 2.18-2.30 (m, 2H); 2.92-3.02 (m, 5H); 3.73 (s, 3H); 3.75 (s, 3H); 3.93 (s, 2H); 4.11 (t, 2H, J=6.3 Hz); 6.16 (dd, 1H, J=8.7 Hz, J=2.8 Hz); 6.30 (d, 1H, J=2.7 Hz); 6.48-6.58 (m, 2H); 6.78 (d, 1H, J=8.7 Hz); 6.89-6.98 (m, 2H); 6.99-7.11 (m, 3H).

$^{13}$C-NMR (MeOD-d4): δ (ppm) 24.6; 26.6; 39.8; 47.7; 55.2; 55.8; 67.2; 98.0-98.3 (m); 101.7; 105.3 (t, J=20.0 Hz); 107.6; 113.1; 115.3; (d, J=23.4 Hz); 121.4; 129.7 (d, J=9.0 Hz); 130.6 (d, J=3.1 Hz); 137.3; 141.1; 142.9; 143.5; 149.8; 160.2 (t, J=14.3 Hz); 161.5 (dd, J=246.6 Hz, J=11.2 Hz); 162.6 (d, J=248.3 Hz).

BIOLOGY EXAMPLES

TGR5/CRE Luciferase Assay

In the following tables TGR5 activation by compounds and subsequent increase in intracellular cAMP were evaluated using a luciferase reporter gene assay. Human embryonic kidney (HEK) 293 cells were transiently co-transfected with pCMV tag4b-TGR5 h (to follow hTGR5 activation) or pCMV AC6-TGR5m (to follow mTGR5 activation) expression plasmids and the pCRE TA-Luciferase reporter plasmid using the JET PEI reagent (Polyplus transfection). Transfected cells were seeded in 96-well plates and incubated overnight with the test compounds at increasing concentrations tested in duplicate. Lithocolic acid (LCA) at 10 µM was used as a positive reference compound. The cAMP-dependent luciferase expression was followed using the BrightGlo reagent according to the manufacturer (Promega) instructions. Luminescence was read with a Mithras plate reader (Berthold). Data were expressed as percentage of the 10 µM LCA value and EC$_{50}$ values were calculated using XL fit 5 software or GraphPad Prism 5. Concentration-response curves were fitted by a nonlinear regression analysis to a 4 parameter logistic equation.

The results of the TGR5/CRE Luciferase assay are presented in Table 2 heraftier.

TABLE 2
| | | TGR5 assay results | | | |
|---|---|---|---|---|---|
| Example | Structure | hTGR5 EC$_{50}$ (μM) | % trans | mTGR5 EC$_{50}$ (μM) | % trans |
| 1 | 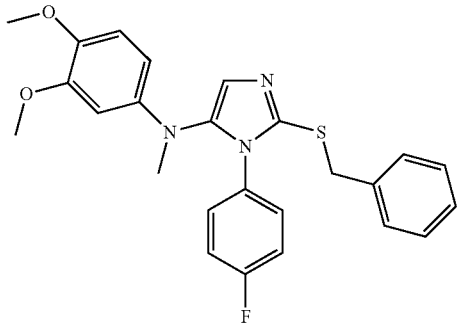 [SMILES: COc1ccc(N(C)c2cnc(SCc3ccccc3)n2-c2ccc(F)cc2)cc1OC] | 0.156 | 82 | 0.068 | 96 |
| 2 | 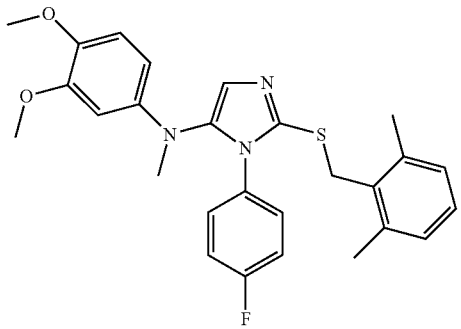 [SMILES: COc1ccc(N(C)c2cnc(SCc3c(C)cccc3C)n2-c2ccc(F)cc2)cc1OC] | 0.299 | 93 | 0.044 | 97 |
| 3 | 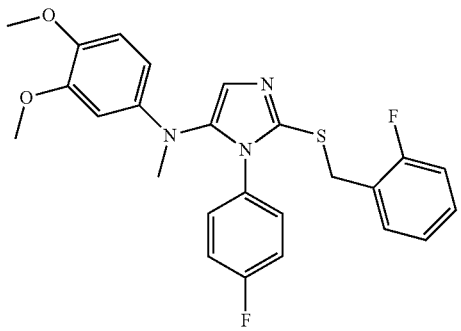 [SMILES: COc1ccc(N(C)c2cnc(SCc3ccccc3F)n2-c2ccc(F)cc2)cc1OC] | 0.128 | 106 | 0.012 | 100 |
| 4 | 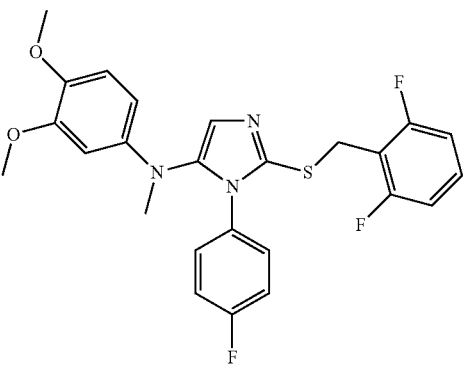 [SMILES: COc1ccc(N(C)c2cnc(SCc3c(F)cccc3F)n2-c2ccc(F)cc2)cc1OC] | 0.039 | 95 | 0.001 | 107 |

TABLE 2-continued

TGR5 assay results

| Example | Structure | hTGR5 EC$_{50}$ (μM) | % trans | mTGR5 EC$_{50}$ (μM) | % trans |
|---|---|---|---|---|---|
| 5 | 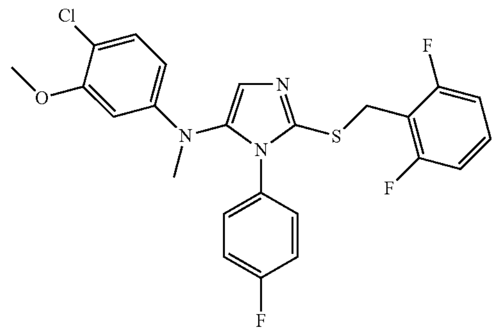 [SMILES: COc1cc(N(C)c2cnc(SCc3c(F)cccc3F)n2-c2ccc(F)cc2)ccc1Cl] | 0.88 | 57 | 0.044 | 82 |
| 6 | 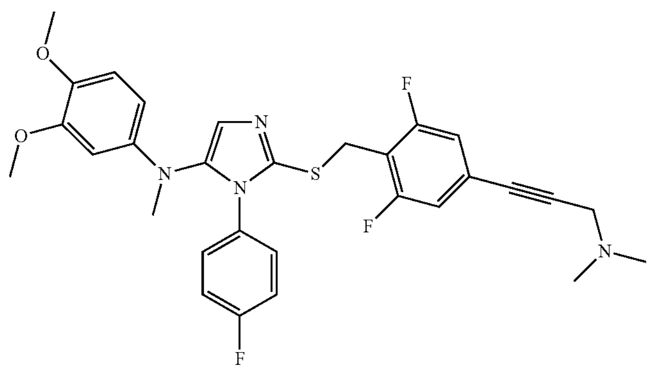 | 0.071 | 89 | 0.004 | 91 |
| 7 | 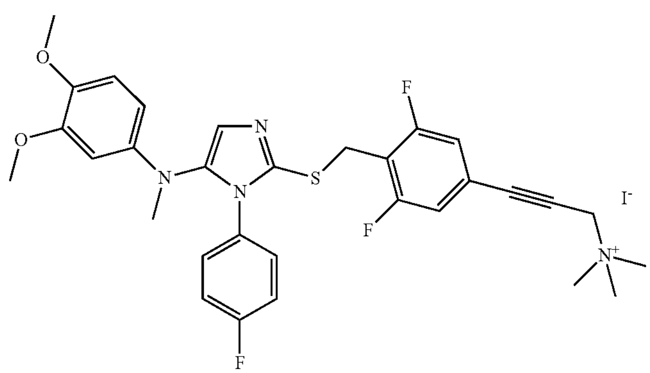 | 0.177 | 104 | 0.007 | 112 |
| 8 | 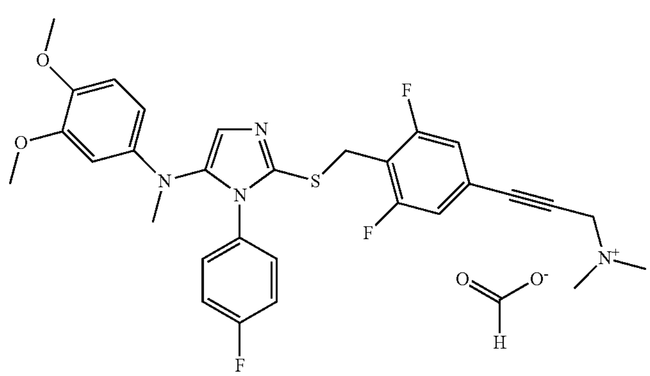 | 0.260 | 95 | 0.017 | 96 |

TABLE 2-continued

TGR5 assay results

| Example | Structure | hTGR5 EC$_{50}$ (μM) | % trans | mTGR5 EC$_{50}$ (μM) | % trans |
| --- | --- | --- | --- | --- | --- |
| 9 | 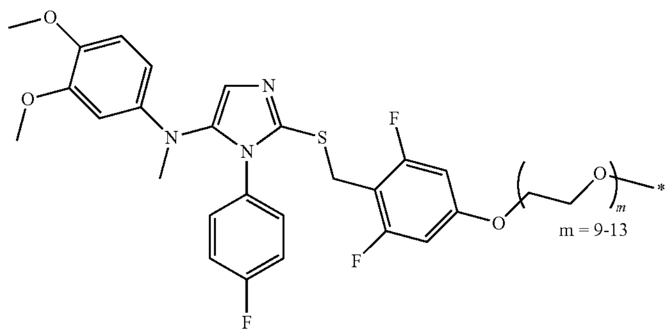 | 0.160 | 85 | 0.018 | 98 |
| 12 | 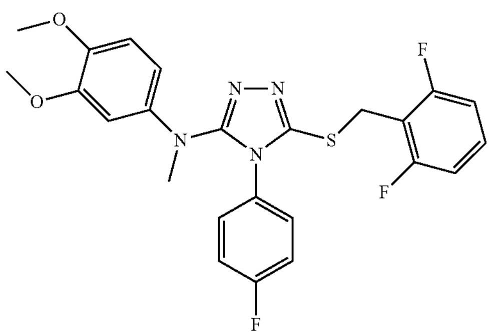 [SMILES: COc1ccc(N(C)c2nnc(SCc3c(F)cccc3F)n2-c2ccc(F)cc2)cc1OC] | 4.3 | 56 | 0.18 | 89 |
| 13 | 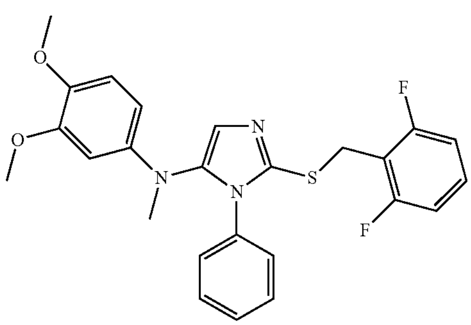 [SMILES: COc1ccc(N(C)c2cnc(SCc3c(F)cccc3F)n2-c2ccccc2)cc1OC] | 0.25 | 93 | 0.005 | 110 |
| 14 | 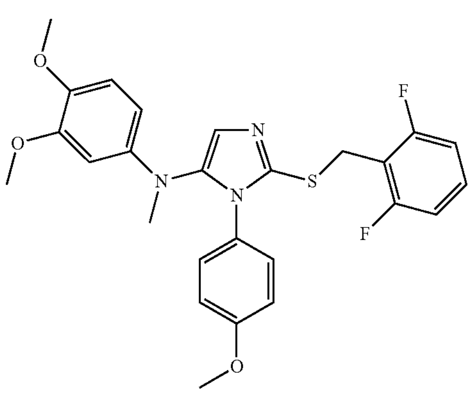 [SMILES: COc1ccc(-n2c(N(C)c3ccc(OC)c(OC)c3)cnc2SCc2c(F)cccc2F)cc1] | 7.7 | 55 | 0.94 | 107 |

TABLE 2-continued

TGR5 assay results

| Example | Structure | hTGR5 EC$_{50}$ (μM) | % trans | mTGR5 EC$_{50}$ (μM) | % trans |
|---------|-----------|----------------------|---------|----------------------|---------|
| 15 | 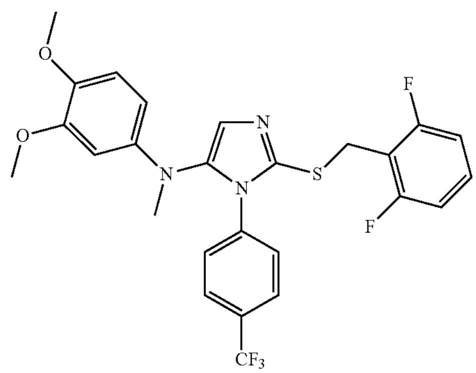 [SMILES: COc1ccc(N(C)c2cnc(SCc3c(F)cccc3F)n2-c2ccc(C(F)(F)F)cc2)cc1OC] | 0.9 | 65 | 0.37 | 107 |
| 16 | 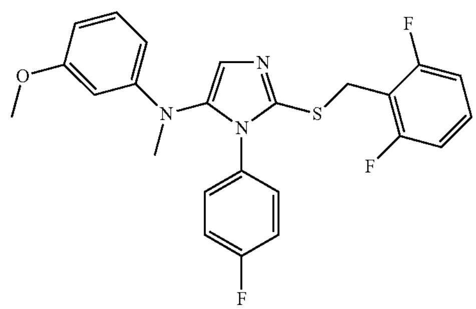 [SMILES: COc1cccc(N(C)c2cnc(SCc3c(F)cccc3F)n2-c2ccc(F)cc2)c1] | 0.99 | 59 | 0.09 | 118 |
| 17 | 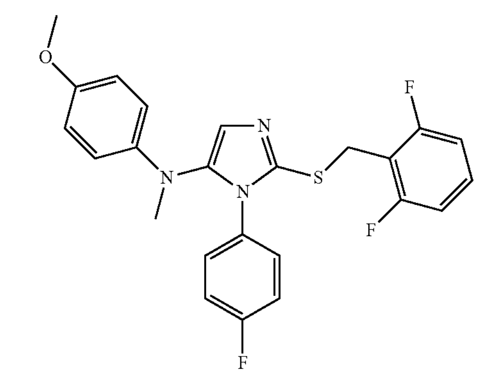 [SMILES: COc1ccc(N(C)c2cnc(SCc3c(F)cccc3F)n2-c2ccc(F)cc2)cc1] | 1.1 | 59 | 0.14 | 116 |
| 18 | 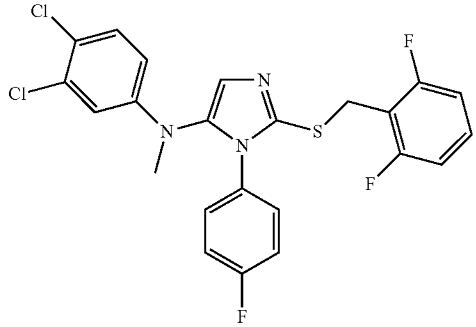 [SMILES: CN(c1ccc(Cl)c(Cl)c1)c1cnc(SCc2c(F)cccc2F)n1-c1ccc(F)cc1] | 0.75 | 33 | 0.51 | 116 |

TABLE 2-continued
TGR5 assay results
| Example | Structure | hTGR5 EC$_{50}$ (μM) | % trans | mTGR5 EC$_{50}$ (μM) | % trans |
|---|---|---|---|---|---|
| 19 | 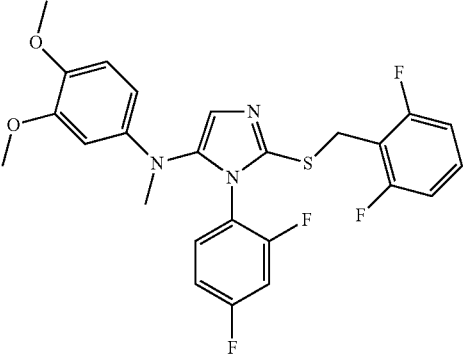 [SMILES: COc1ccc(N(C)c2cnc(SCc3c(F)cccc3F)n2-c2ccc(F)cc2F)cc1OC] | 0.047 | 108 | 0.0048 | 90 |
| 20 | 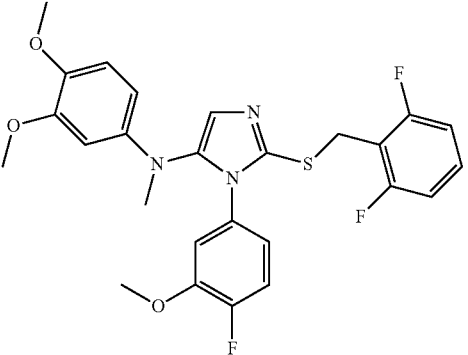 [SMILES: COc1cc(-n2c(N(C)c3ccc(OC)c(OC)c3)cnc2SCc2c(F)cccc2F)ccc1F] | 0.015 | 111 | 0.001 | 108 |
| 21 | 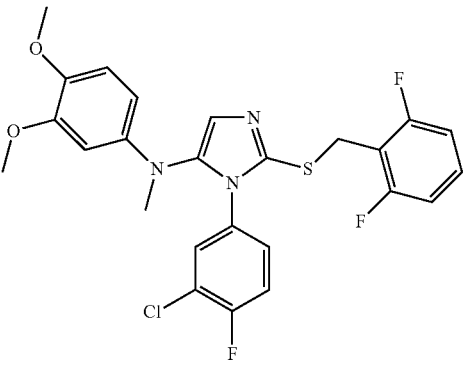 [SMILES: COc1ccc(N(C)c2cnc(SCc3c(F)cccc3F)n2-c2ccc(F)c(Cl)c2)cc1OC] | 0.035 | 112 | 0.002 | 99 |
| 22 | 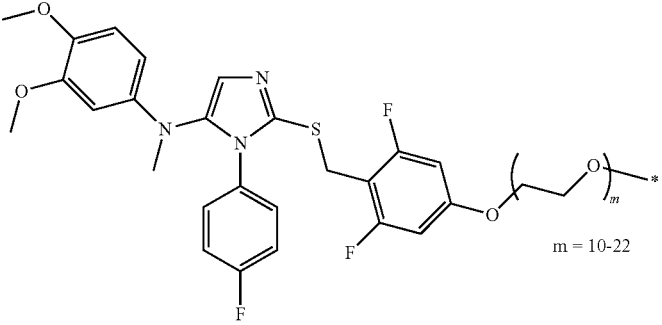 m = 10-22 | 0.58 | 60 | 0.029 | 85 |

TABLE 2-continued

TGR5 assay results

| Example | Structure | hTGR5 EC$_{50}$ (μM) | % trans | mTGR5 EC$_{50}$ (μM) | % trans |
|---|---|---|---|---|---|
| 23 | (structure; m = 15-22) | 0.33 | 103 | 0.026 | 108 |
| 24 | (structure; m = 36-47) | 1.2 | 71 | 0.068 | 126 |
| 25 | (structure) | 0.24 | 90 | 0.010 | 97 |
| 26 | (structure) | 0.04 | 117 | 0.0005 | 105 |

The invention claimed is:
1. A compound of Formula I:

(I)

or a pharmaceutically acceptable salt or solvate thereof, wherein:
X is CH or N;
Y is $CR^1$ or N;
Z is $CR^2$ or N; with the proviso that Y and Z are not both N;
$R^1$ and $R^2$ are, independently of each other, C1-C2-alkoxy or halo;
$R^3$ is H or methyl;
$R^4$ is phenyl or pyridinyl, said phenyl or pyridinyl being unsubstituted or substituted by one or more groups selected from the group consisting of halo, C1-C2-alkoxy, and haloalkyl;
$R^5$ and $R^6$ are, independently of each other, H, halo or C1-C2-alkyl;
$L^2$ is O, —C≡C—, $CH_2$, NH, NH(CO), (CO)NH, $NH(SO_2)$, or $(SO_2)NH$
n is an integer from 0 to 4;
A is selected from the group consisting of $N(R^7)_2$, wherein $R^7$ is H or linear C1-C4-alkyl, $SO_3H$, wherein m is 3 to 500, wherein $R^8$ is linear C1-C4-alkyl and $Q^-$ is a counter anion, and
a cyclic moiety selected from the group consisting of wherein $R^A$ is H, OH, C0-C4-alkyl-COOH or C1-C6-alkyl, $R^B$ is C1-C6-alkyl optionally substituted with —COOH, $R^C$ is C1-C6-alkyl, and $Q^-$ is a counter anion; or
$L^2$-$(CH_2)_n$-A is H.

2. The compound according to claim 1, or a pharmaceutically acceptable salt or solvate thereof, wherein
$L^2$ is O, —C≡C—, $CH_2$, NH, NH(CO), (CO)NH, $NH(SO_2)$, or $(SO_2)NH$
n is an integer from 0 to 4;
A is selected from the group consisting of $N(R^7)_2$, wherein $R^7$ is H or linear C1-C4-alkyl, $SO_3H$, wherein m is 3 to 500, wherein $R^8$ is linear C1-C4-alkyl and $Q^-$ is a counter anion.

3. The compound according to claim 1, or a pharmaceutically acceptable salt or solvate thereof, wherein $L_2$-$(CH_2)_n$-A is H.

4. The compound according to claim 1, or a pharmaceutically acceptable salt or solvate thereof, wherein X is CH.

5. The compound according to claim 1, or a pharmaceutically acceptable salt or solvate thereof, wherein X is N.

6. The compound according to claim 1, or a pharmaceutically acceptable salt or solvate thereof, wherein $R^1$ and $R^2$ are both methoxy.

7. The compound according to claim 1, or a pharmaceutically acceptable salt or solvate thereof, wherein $R^5$ and $R^6$ are, independently of each other, H, fluoro or methyl.

8. The compound according to claim 1, or a pharmaceutically acceptable salt or solvate thereof, having Formula II

II or a pharmaceutically acceptable salt or solvate thereof.
9. The compound according to claim 8, or a pharmaceutically acceptable salt or solvate thereof, having Formula III

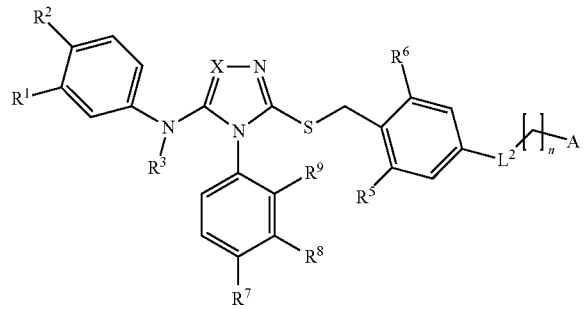

III or a pharmaceutically acceptable salt or solvate thereof, wherein $R^7$, $R^8$, and $R^9$ are, independently of each other, selected from the group consisting of fluoro, chloro, halomethyl, and C1-C2-alkoxy, with the proviso that at least one of $R^7$, $R^8$, and $R^9$ is not H.

10. The compound according to claim 9, or a pharmaceutically acceptable salt or solvate thereof, wherein $R^7$ is fluoro and $R^8$ and $R^9$ are H.

11. The compound according to claim 1, selected from the group consisting of:

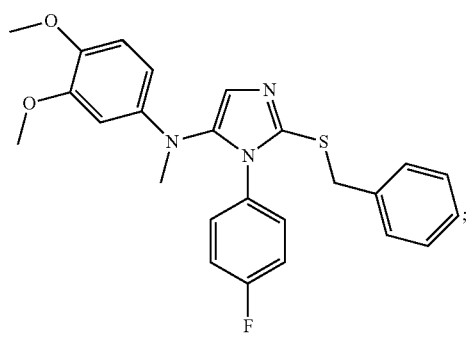

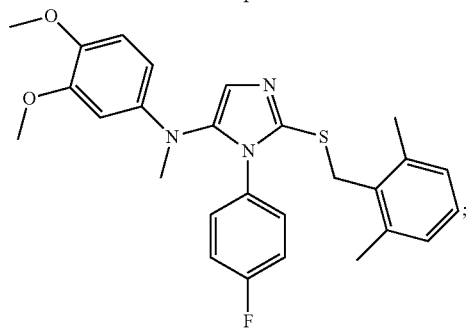

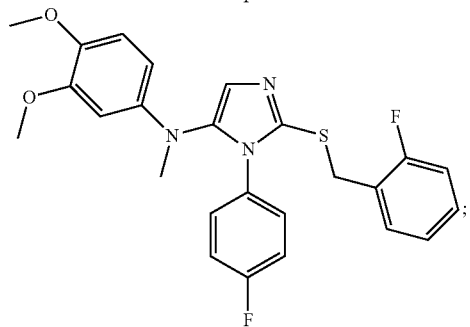

-continued

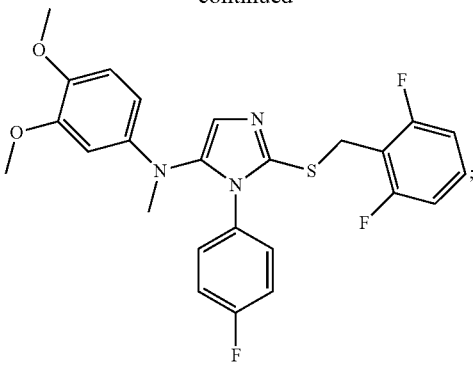

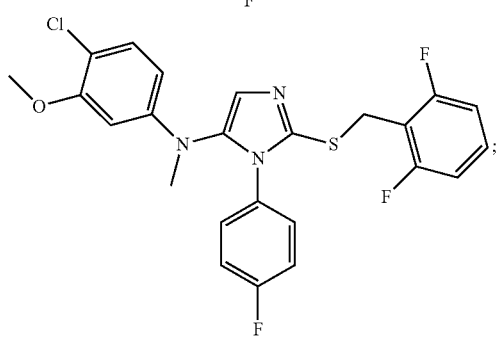

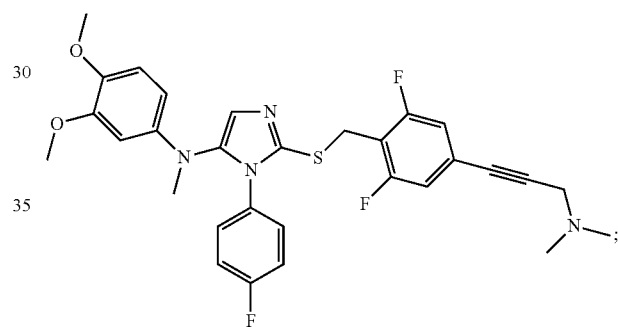

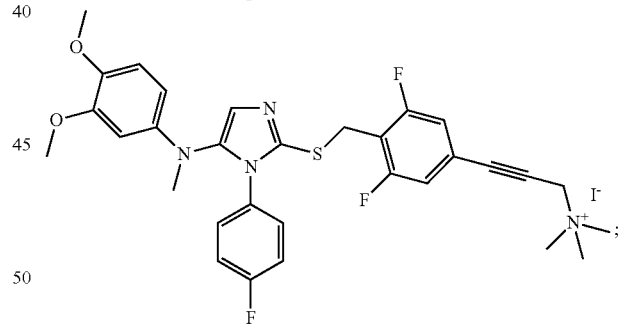

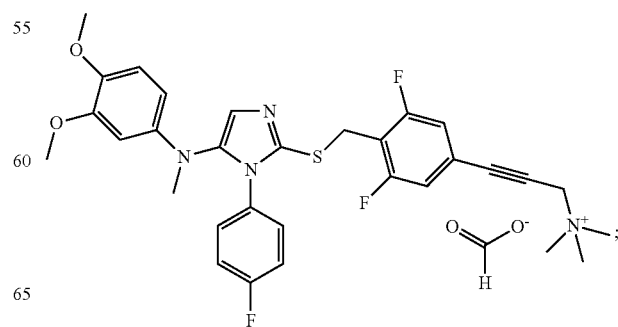

91
-continued
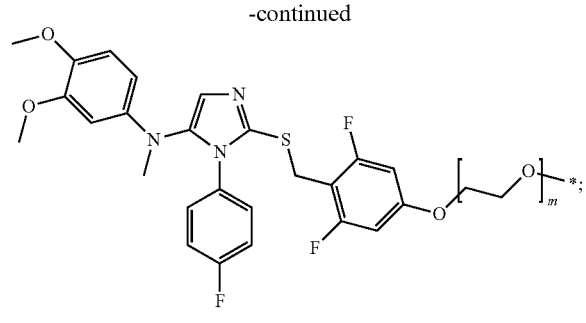
m = 9-13
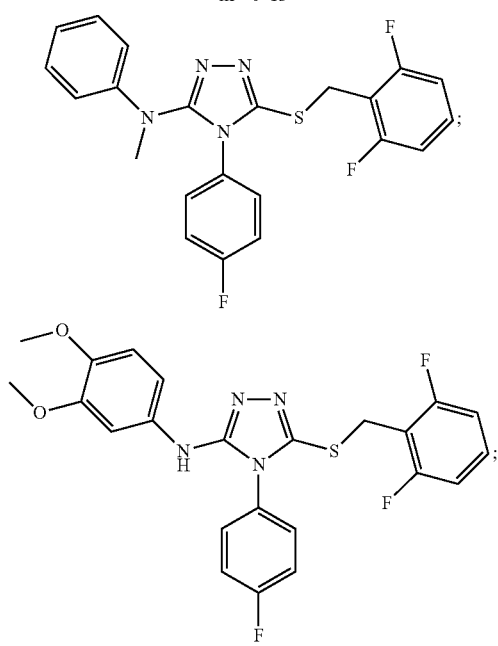
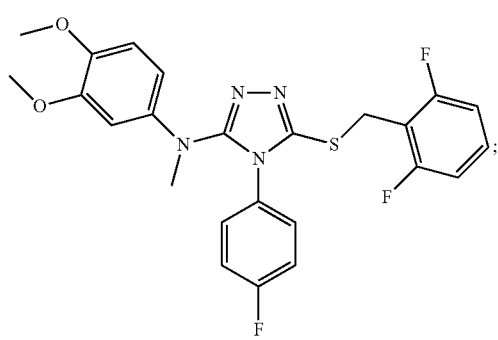
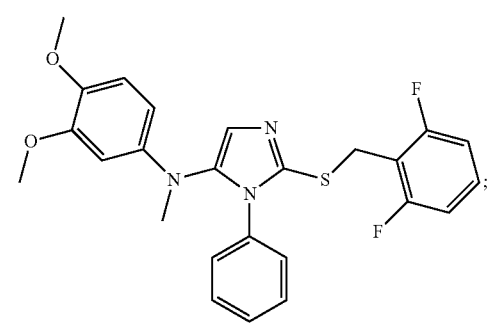
92
-continued
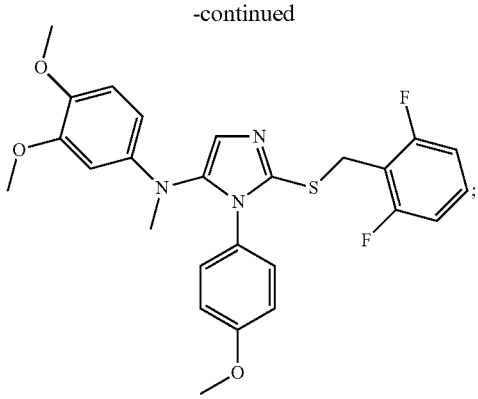
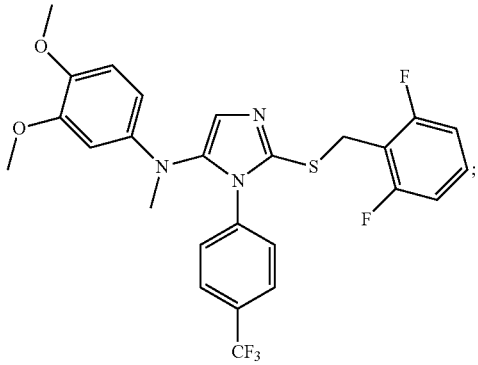
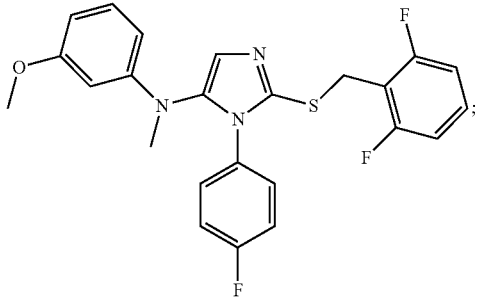
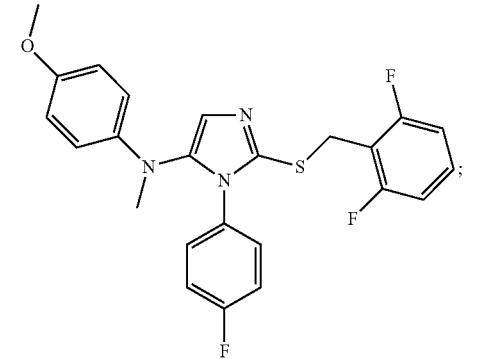
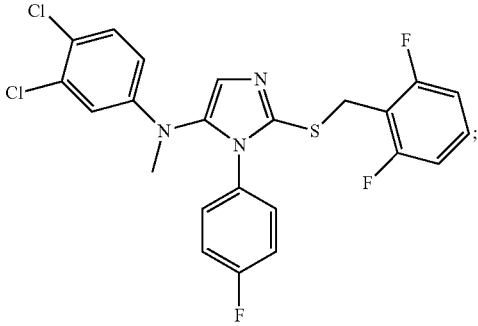

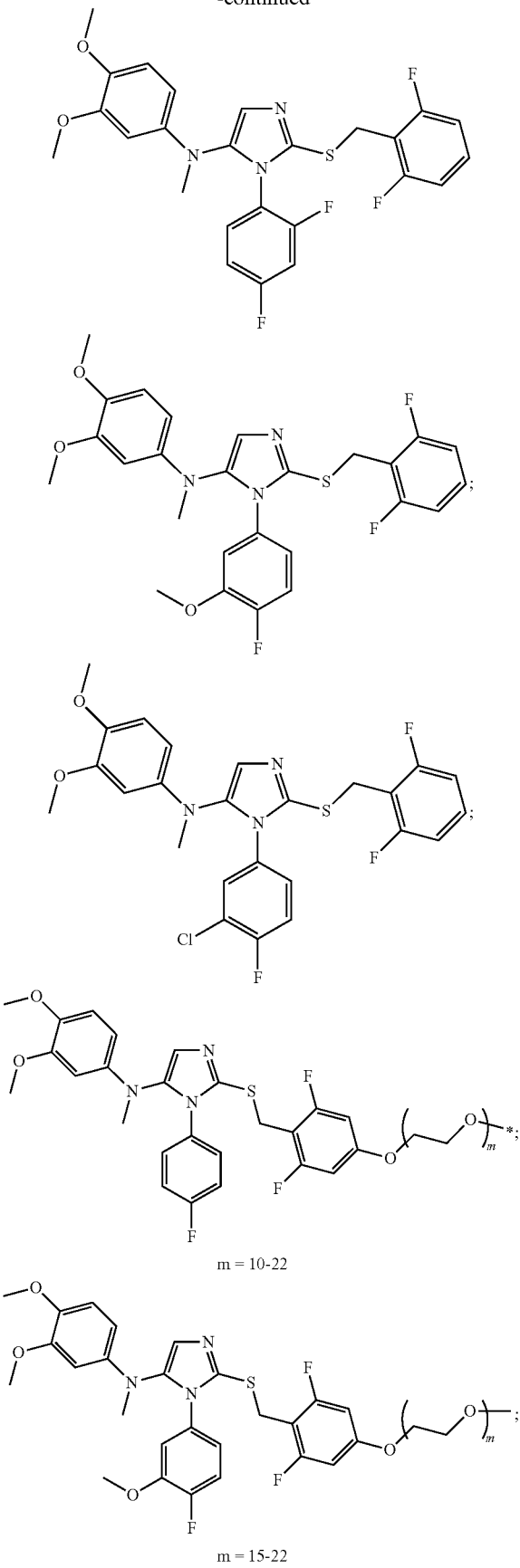

m = 10-22 m = 15-22

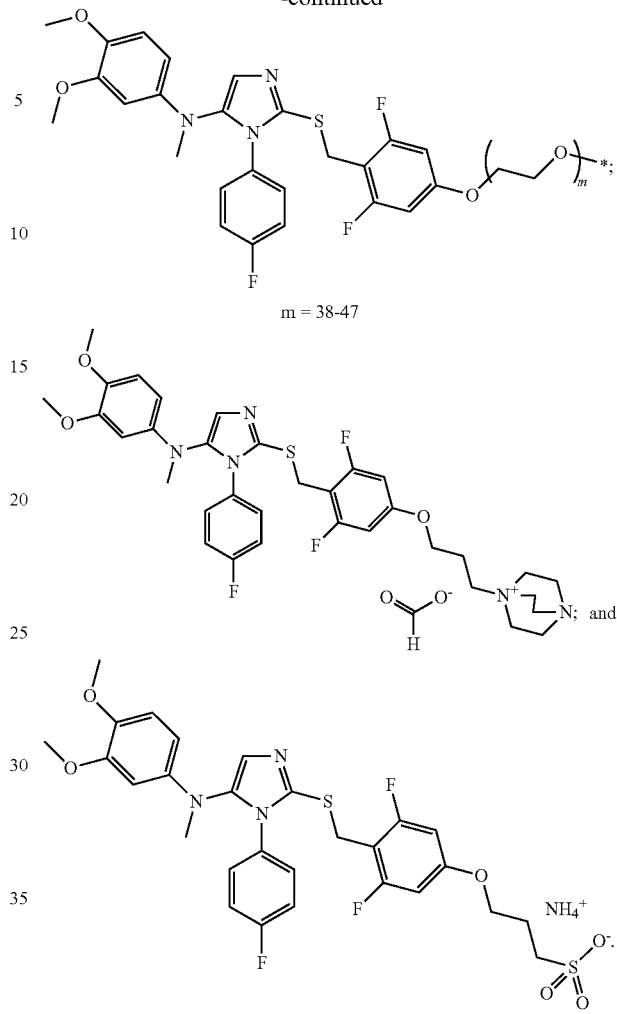

m = 38-47

12. A pharmaceutical composition, comprising a compound according to claim 1, or a pharmaceutically acceptable salt or solvate thereof, and at least one pharmaceutically acceptable carrier, diluent, excipient and/or adjuvant.

13. A method for treating a TGR5 related metabolic and/or a gastrointestinal disease, comprising the step of administering a therapeutically effective amount of a compound according to claim 1, or a pharmaceutically acceptable salt or solvate thereof, to a patient in need thereof, wherein said disease is selected from type II diabetes, obesity, dyslipidemia, atherosclerosis, Irritable Bowel Syndrome (IBS), Crohn's disease, ulcerative colitis, and colitis.

14. The method according to claim 13, wherein the disease is a metabolic disease selected from the group consisting of type II diabetes, obesity, dyslipidemia, and atherosclerosis.

15. The method according to claim 13, wherein the disease is a gastrointestinal disease selected from the group consisting of Irritable Bowel Syndrome (IBS), Crohn's disease, ulcerative colitis, and colitis.

16. A method of activating TGR5 receptor in a patient in need of such treatment, comprising the step of administering to said patient an effective amount of a compound according to claim 1, or a pharmaceutically acceptable salt or solvate thereof.

17. The method according to claim 16, wherein the compound is an agonist of TGR5 receptor.

* * * * *

UNITED STATES PATENT AND TRADEMARK OFFICE
CERTIFICATE OF CORRECTION

PATENT NO. : 10,323,016 B2
APPLICATION NO. : 15/315270
DATED : June 18, 2019
INVENTOR(S) : Julie Charton et al.

Page 1 of 1

It is certified that error appears in the above-identified patent and that said Letters Patent is hereby corrected as shown below:

In the Claims

Column 89, Line 20, "from the group consisting of fluoro" should be printed as "from the group consisting of H, fluoro."

Column 94, Line 14, "m=38-47" should be printed as "m=36-47."

Signed and Sealed this
Thirty-first Day of March, 2020

Andrei Iancu
*Director of the United States Patent and Trademark Office*